United States Patent
Yuan

(10) Patent No.: US 9,643,977 B2
(45) Date of Patent: May 9, 2017

(54) NECROPTOSIS INHIBITORS AND METHODS OF USE THEREFOR

(75) Inventor: Junying Yuan, Newton, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 57 days.

(21) Appl. No.: 14/004,474

(22) PCT Filed: Mar. 12, 2012

(86) PCT No.: PCT/US2012/028747
§ 371 (c)(1),
(2), (4) Date: Nov. 21, 2013

(87) PCT Pub. No.: WO2012/125544
PCT Pub. Date: Sep. 20, 2012

(65) Prior Publication Data
US 2014/0066466 A1 Mar. 6, 2014

Related U.S. Application Data

(60) Provisional application No. 61/451,772, filed on Mar. 11, 2011.

(51) Int. Cl.
| | |
|---|---|
| C07D 403/06 | (2006.01) |
| C07D 495/04 | (2006.01) |
| C07D 417/12 | (2006.01) |
| C07D 487/04 | (2006.01) |
| C07D 209/82 | (2006.01) |
| C07D 231/14 | (2006.01) |
| C07D 231/40 | (2006.01) |
| C07D 233/56 | (2006.01) |
| C07D 235/30 | (2006.01) |
| C07D 237/18 | (2006.01) |
| C07D 409/06 | (2006.01) |
| C07D 261/14 | (2006.01) |
| C07D 263/58 | (2006.01) |
| C07D 277/46 | (2006.01) |
| C07D 277/54 | (2006.01) |
| C07C 211/52 | (2006.01) |
| C07C 235/38 | (2006.01) |
| C07D 215/08 | (2006.01) |
| C07D 261/20 | (2006.01) |
| C07D 403/12 | (2006.01) |
| C07D 405/06 | (2006.01) |

(52) U.S. Cl.
CPC .......... C07D 495/04 (2013.01); C07C 211/52 (2013.01); C07C 235/38 (2013.01); C07D 209/82 (2013.01); C07D 215/08 (2013.01); C07D 231/14 (2013.01); C07D 231/40 (2013.01); C07D 233/56 (2013.01); C07D 235/30 (2013.01); C07D 237/18 (2013.01); C07D 261/14 (2013.01); C07D 261/20 (2013.01); C07D 263/58 (2013.01); C07D 277/46 (2013.01); C07D 277/54 (2013.01); C07D 403/06 (2013.01); C07D 403/12 (2013.01); C07D 405/06 (2013.01); C07D 409/06 (2013.01); C07D 417/12 (2013.01); C07D 487/04 (2013.01)

(58) Field of Classification Search
CPC ... C07D 495/04; C07D 487/04; C07D 261/14
See application file for complete search history.

(56) References Cited

U.S. PATENT DOCUMENTS

| | | |
|---|---|---|
| 6,756,394 B1 | 6/2004 | Yuan et al. |
| 7,253,201 B2 | 8/2007 | Yuan et al. |
| 7,491,743 B2 | 2/2009 | Cuny et al. |
| 8,143,300 B2 | 3/2012 | Cuny et al. |
| 8,278,344 B2 | 10/2012 | Cuny et al. |
| 8,324,262 B2 | 12/2012 | Yuan et al. |
| 8,658,689 B2 | 2/2014 | Cuny et al. |
| 8,741,942 B2 | 6/2014 | Cuny et al. |
| 9,108,955 B2 | 8/2015 | Cuny et al. |
| 2002/0155172 A1 | 10/2002 | Yuan et al. |
| 2005/0119260 A1 | 6/2005 | Cuny et al. |
| 2005/0131044 A1 | 6/2005 | Yuan et al. |
| 2007/0254877 A1 | 11/2007 | Nishikimi et al. |
| 2009/0099242 A1 | 4/2009 | Cuny et al. |
| 2010/0087453 A1 | 4/2010 | Yuan et al. |
| 2010/0190836 A1 | 7/2010 | Yuan et al. |
| 2010/0317701 A1 | 12/2010 | Cuny et al. |
| 2011/0144169 A1 | 6/2011 | Cuny et al. |
| 2012/0122889 A1 | 5/2012 | Yuan et al. |

(Continued)

FOREIGN PATENT DOCUMENTS

| | | |
|---|---|---|
| WO | WO-97/12613 | 4/1997 |
| WO | WO-00/06088 | 2/2000 |

(Continued)

OTHER PUBLICATIONS

Collins et al J'nal of ACS (1957) 79, 1103.*
Bottin et al., "Genotoxic effects of bitumen fumes in Big Blue® transgenic rat lung," Mutation Research, 596:91-105 (2006).
Knox et al., "The death domain kinase RIP1 links the immunoregulatory CD40 receptor to Apoptotic signaling in carcinomas," J. Cell Biol., 192(3):391-399 (2011).
International Search Report dated Jan. 2, 2013, from PCT/US2012/028747.
International Search Report for PCT/US2012/028747, 4 pages (Jan. 2, 2013).
Written Opinion for PCT/US2012/028747, 7 pages (Jan. 2, 2013).

*Primary Examiner* — Paul V Ward
(74) *Attorney, Agent, or Firm* — Choate, Hall & Stewart LLP; Brenda H. Jarrell; Nishat A. Shaikh

(57) ABSTRACT

Described herein are compositions that inhibit the production of TNFα downstream of CD40 activation. As such, also described are various methods of using compositions exhibiting this activity for the treatment or prevention of inflammatory diseases associated with TNFα production or CD40 activation.

35 Claims, 25 Drawing Sheets

(56) References Cited

U.S. PATENT DOCUMENTS

| | | |
|---|---|---|
| 2012/0149702 A1 | 6/2012 | Cuny et al. |
| 2012/0309795 A1 | 12/2012 | Cuny et al. |
| 2013/0158024 A1 | 6/2013 | Yuan et al. |
| 2014/0024657 A1 | 1/2014 | Yuan et al. |
| 2014/0024662 A1 | 1/2014 | Yuan et al. |
| 2014/0128437 A1 | 5/2014 | Cuny et al. |
| 2014/0323489 A1 | 10/2014 | Yuan et al. |
| 2016/0024098 A1 | 1/2016 | Yuan et al. |
| 2016/0102053 A1 | 4/2016 | Cuny et al. |
| 2016/0168128 A1 | 6/2016 | Yuan et al. |

FOREIGN PATENT DOCUMENTS

| | | |
|---|---|---|
| WO | WO-2004/071507 | 8/2004 |
| WO | WO-2005/077344 | 8/2005 |
| WO | WO-2007/075772 | 7/2007 |
| WO | WO-2008/045406 | 4/2008 |
| WO | WO-2009/023272 | 2/2009 |
| WO | WO-2010/075290 | 7/2010 |
| WO | WO-2010/075561 | 7/2010 |
| WO | WO-2014/152182 A1 | 9/2014 |
| WO | WO-2016/094846 A1 | 6/2016 |

* cited by examiner

Figure 7

| Compounds | Structures | L929+zVAD | | Jurkat FADD-/- +TNFa | | MDA-MB-231+SMAC | Jurkat+TNFa+CHX | 293T-TNFa induced NFkB | In Vitro RIP1 kinase domain auto-phosphorylation |
|---|---|---|---|---|---|---|---|---|---|
| | | IC50 | 10uM-Inhibition | IC50 | 10uM-Inhibition | 10uM-Inhibition | 10uM-Inhibition | 10uM-Inhibition | 10uM-Inhibition |
| Nec-21 | 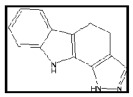 | 7.36E-08 | 97% | 2.74E-07 | 105% | 39% | 17% | 12% | + |
| Nec-21i | 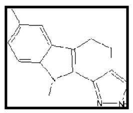 | | 21% | | 2% | 18% | 3% | 3% | - |
| Nec-22 | 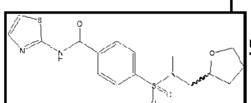 | 5.37E-07 | 101% | 3.54E-05 | 74% | 4% | 1% | 2% | + |
| Nec-22i | 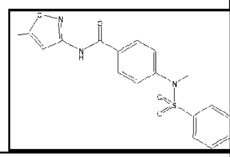 | | 2% | | -4% | -5% | -1% | 2% | - |
| Nec-23 | 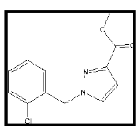 | 1.40E-06 | 96% | 4.90E-07 | 112% | 17% | 7% | 6% | + |

| | | | | | | | | |
|---|---|---|---|---|---|---|---|---|
| Nec-24 |  | 4.99E-06 | 88% | 5.53E-07 | 119% | -20% | 2% | -1% | + |
| Nec-25 |  | 1.02E-06 | 93% | 1.07E-05 | 38% | -23% | 3% | 21% | + |
| Nec-26 |  | | 30% | 1.05E-06 | 73% | 20% | 6% | 19% | + |
| Nec-27 |  | 7.51E-06 | 52% | 3.93E-06 | 92% | 2% | 0% | 4% | partial |
| Nec-28 |  | 1.10E-06 | 90% | 2.02E-06 | 92% | 19% | 3% | 9% | partial |

Figure 7 (continued)

| | | | | | | | | |
|---|---|---|---|---|---|---|---|---|
| Nec-29 | [structure] | 8.15E-07 | 89% | 1.05E-06 | 44% | 24% | 10% | 14% | partial |
| Nec-29i | [structure] | | 6% | | 38% | 6% | 5% | -12% | partial |
| Nec-30 | [structure] | 8.68E-06 | 50% | 1.16E-06 | 99% | -4% | 6% | 0% | - |
| Nec-31 | [structure] | 1.00E-07 | 106% | 2.02E-06 | 101% | 29% | 5% | 23% | partial |
| Nec-32 | [structure] | | 50% | 7.87E-06 | 85% | 13% | 3% | 0% | - |
| Nec-33 | [structure] | 4.15E-07 | 91% | 1.50E-06 | 64% | 4% | 0% | 0% | partial |

| | | | | | | | | |
|---|---|---|---|---|---|---|---|---|
| Nec-33i |  | 5.24E-08 | 9% | | 1% | 6% | 5% | -15% | - |
| Nec-34 |  | | 102% | 5.67E-06 | 112% | 21% | 6% | 10% | - |

| Compounds | Structures | L929+zVAD IC50 | L929+zVAD 10uM-Inhibition | Jurkat FADD-/- +TNFa IC50 | Jurkat FADD-/- +TNFa 10uM-Inhibition | MDA-MB-231+SM AC 10uM-Inhibition | Jurkat+TNFa +CHX 10uM-Inhibition | 293T-TNFa induced NFkB 10uM-Inhibition | In Vitro RIP1 kinase domain auto-phosphorylation 10uM-Inhibition |
|---|---|---|---|---|---|---|---|---|---|
| Nec-1 | 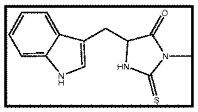 | 1.50 E-07 | 98% | 1.48E-07 | 90% | 10% | 11% | 3% | + |
| Nec-8 | 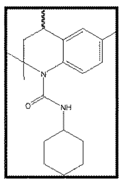 | 9.41 E-07 | 98% | | 53% | -5% | 8% | 3% | - |
| Nec-8i | 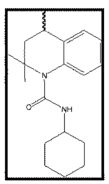 | | 51% | | 18% | -4% | 0% | 8% | - |
| Nec-18-Ying | 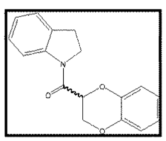 | 4.25 E-07 | 42% | 6.28E-06 | 101% | 10% | 2% | -1% | partial |

Figure 8 (continued)

| | | | | | | | |
|---|---|---|---|---|---|---|---|
| Helenalin | [structure] | Cyto toxic | 42% (75% at 200 nM) | | -29% | 62% at 1uM | 11% | 92% | - |
| Helenalin-i | [structure] | | -5% | | -20% | 24% | -29% | 36% | + |
| 3P | [structure] | 4.79 E-08 | 105% | 8.24E-07 | 69% | 22% | 6% | 2% | + |
| 3N | [structure] | | 17% | | 61% | 11% | 3% | 10% | - |
| 14P | [structure] | 2.29 E-07 | 90% | | 20% | -24% | -2% | 24% | partial |

| | | | | | | | | |
|---|---|---|---|---|---|---|---|---|
| 19P |  | | 30% | 1.05E-06 | 73% | 20% | 6% | 19% | + |
| Nec-10 |  | 1.97 E-07 | | 4.77E-07 | | | | | - |
| Nec-11 |  | 8.90 E-07 | | 5.38E-06 | | | | | inhibit RIP/293 |
| Nec-12 |  | 6.59 E-07 | | 3.23E-06 | | | | | inhibit RIP/293 |
| Nec-13 |  | 8.66 E-06 | | 2.16E-07 | | | | | + |

| | | | | | | |
|---|---|---|---|---|---|---|
| Nec-14 |  | 4.20 E-06 | | 4.10E-07 | | ? |
| Nec-15 |  | 1.11 E-06 | | 8.96E-06 | | - |
| Nec-16 |  | 7.46 E-06 | | 3.43E-07 | | ? |
| Nec-17 |  | 4.02 E-06 | | 3.69E-07 | | ? |

| | | | | | | | | |
|---|---|---|---|---|---|---|---|---|
| Nec-18 |  | 2.30 E-05 | | 6.29E-07 | | | | ? |
| Nec-19 |  | 7.30 E-05 | | 6.29E-07 | | | | ? |
| Nec-20 |  | 1.01 E-05 | | 6.68E-07 | | | | ? |

Figure 9

| Compounds | Structures | Well loc | Inhibit RIP1? | EC50 FADD -/- Jurkat | EC50 L929 | LD50 FADD -/- Jurkat | comments |
|---|---|---|---|---|---|---|---|
| Nec-1 | 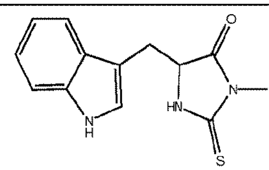 | | | 1.9263 | 2.456 | 374 | |
| Nec-2 | 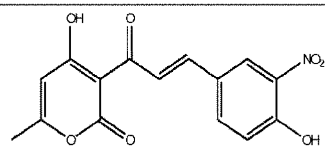 | | | | | | |
| Nec-3 | 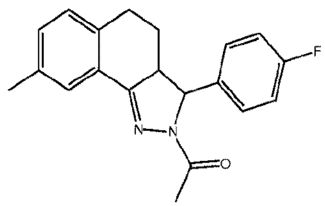 | | | | | | |
| Nec-4 | 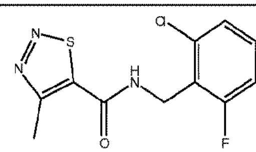 | | | | | | |
| Nec-5 | 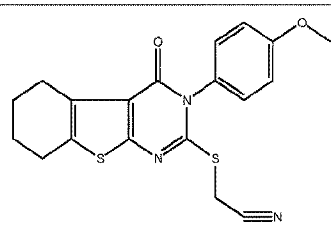 | | | | | | |

| | | Strongest on L929 cells |
|---|---|---|
| | | >2000 |
| | | 0.197 |
| | | 0.4769 |
| | | No |
| | | 1613-F17 |
|  |  |  |
| Nec-8 | Nec-9 | Nec-10 |

| | | | | | |
|---|---|---|---|---|---|
| Nec-11 |  | 1625-E18 | inhibit RIP/293 | 5.379 | 0.89 | 539.4 | |
| Nec-12 |  | 1617-G15 | inhibit RIP/293 | 3.227 | 0.659 | 541.3 | |
| Nec-13 |  | 1744-A7 | yes | 0.2161 | 8.66 | 188.9 | Strongest in Fadd-/- Jurkat cells |
| Nec-14 |  | 1550-G4 | ? | 0.4101 | 4.202 | 396.9 | Only partial solubility in DMSO at 30mM |
| Nec-15 |  | 1769-C11 | No | 8.958 | 1.11 | >2000 | Only partial solubility in DMSO at 30mM |

| | | | | | |
|---|---|---|---|---|---|
| Nec-16 |  | 1724-B13 | ? | 0.3431 | 7.458 | 115.7 | |
| Nec-17 |  | 1526-D17 | ? | 0.3688 | 4.02 | 799.5 | Only partial solubility in DMSO at 30mM |
| Nec-18 |  | 1735-J13 | ? | 0.6289 | 23.04 | 356.5 | |
| Nec-19 |  | 1593-C10 | ? | 0.6289 | 72.97 | 247.7 | Only partial solubility in DMSO at 20mM |

| Nec-20 |  | 1613-C12 | ? | 0.6683 | 10.09 | 754 |
|---|---|---|---|---|---|---|

NECROPTOSIS INHIBITORS AND METHODS OF USE THEREFOR

RELATED APPLICATIONS

This application is a national stage application, filed under 35 U.S.C. §371, of international patent application number PCT/US12/028747, which was filed on Mar. 12, 2012, and claims the benefit of priority under 35 U.S.C. §119(e) to Provisional Application Ser. No. 61/451,772 filed Mar. 11, 2011, the contents of both which are incorporated by reference in their entireties.

GOVERNMENT SUPPORT

The invention was made with support provided by the National Institutes of Health (Grant Nos. DP1 OD000580 and RO1 CA13896); therefore, the government has certain rights in this invention.

BACKGROUND

TNFα is an inflammatory cytokine produced by cells in response to infection or disease. TNFα induces a wide range of effects in different cell types, including induction of the inflammation, inhibition of viral replication and cell death via either apoptosis or necrosis. TNFα-induced inflammation is implicated in the etiology of many diseases including, but not limited to, rheumatoid arthritis, Crohn's disease, psoriasis and Alzheimer's disease.

CD40 is a member of the tumor necrosis factor receptor (TNFR) superfamily which is constitutively or inducibly expressed on the surface of a variety of immune and non-immune cell types, including B cells, macrophages, dendritic cells, microglia, endothelial cells, epithelial cells, and keratinocytes. The CD40 ligand, CD154, is transiently expressed on the surface of activated helper CD4+ T cells. The binding of CD154 to CD40 on the surface of antigen presenting cells contributes to the activation of such immune cells and induces a number of downstream effects, including the production of TNFα.

Macrophages are major producers of TNFα under inflammatory conditions.

Macrophages originate from bone marrow-derived mature monocytes. In response to cytokines, myeloid progenitor cells in the bone marrow differentiate into monocytes, which then enter into the blood stream. In response to chemokine signaling or tissue insult, monocytes rapidly migrate into different tissues where they differentiate into tissue macrophages under the influence of growth factors such as G-MCSF or MCSF.

As described above, monocytes and macrophages are activated through contact with activated T cells. The interaction of CD40 on monocytes and macrophages with CD154 on activated CD4+ T cells is essential for T cell-mediated macrophage activation and the resultant production of TNFα. Activated T cells therefore activate resting monocytes and macrophages via CD40 ligation in a contact-dependent manner at sites of inflammation. The consequence of this interaction is the maintenance and augmentation of the inflammatory process that includes the activation of macrophages, increased production of inflammatory cytokines and enhanced monocyte viability.

There is therefore great need for novel compositions and methods that inhibit the production of TNFα downstream of CD40 activation. Such compositions and methods are useful, for example, in the treatment of inflammatory diseases associated with TNFα production and/or CD40 activation.

SUMMARY

In certain embodiments, the present invention relates to a compound selected from the group consisting of a compound of any one of formulas I-XIV:

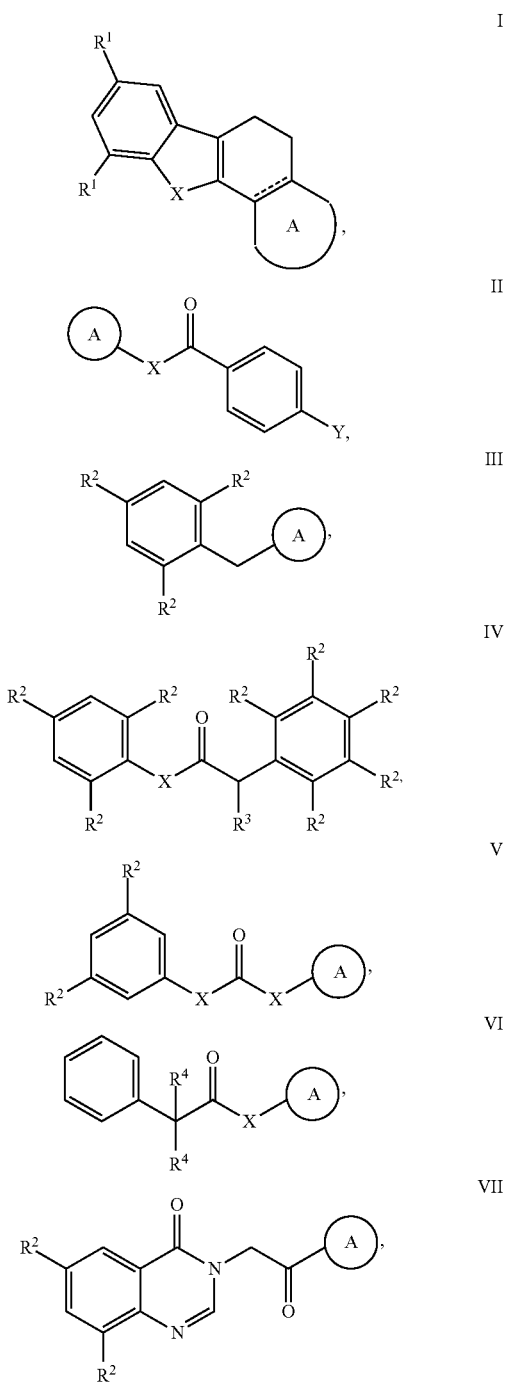

-continued

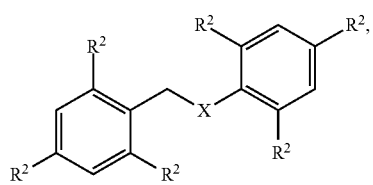

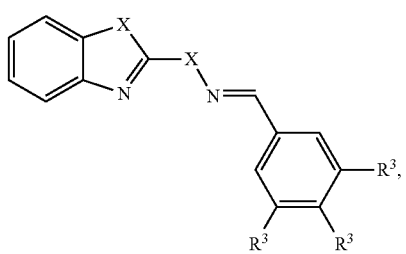

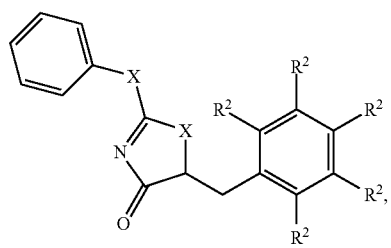

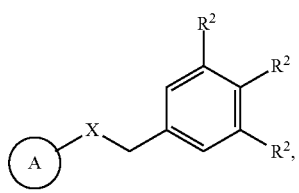

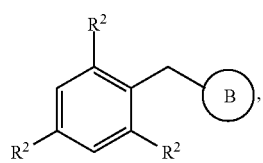

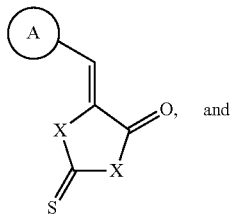

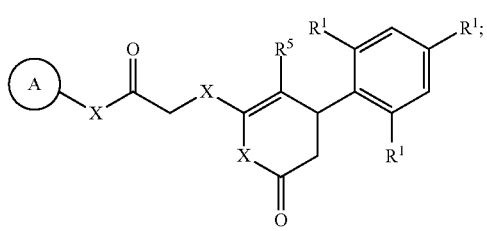

or a pharmaceutically acceptable salt thereof, wherein, independently for each occurrence, Y represents

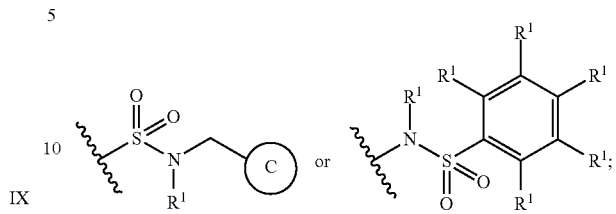

Ⓐ represents a substituted or unsubstituted 5-membered heteroaryl;

Ⓑ represents a substituted 6-membered heteroaryl;

Ⓒ represents an unsubstituted 5-membered heterocyclyl;

⁓ represents a double bond or a single bond;

$R^1$ is —H or alkyl;

$R^2$ is —H, alkyl, halo, or hydroxy;

$R^3$ is —H, alkyloxy, hydroxy, or —$SR^1$;

$R^4$ is —H or alkyl, or any two instances of $R^4$, taken together, form a ring;

$R^5$ is cyano, —C(=O)$R^6$; or —$NO_2$;

$R^6$ is —H, —N($R^1$)$_2$, hydroxy, alkyloxy, or alkyl; and

X represents —O—, —N$R^1$—, or —S—;

wherein Ⓑ or Ⓒ may be substituted with any of alkyl, halo, hydroxy, alkyloxy, —$SR^1$, cyano, —C(=O)$R^6$, —$NO_2$, or —N($R^1$)$_2$.

In certain embodiments, the present invention relates to a compound, or a pharmaceutically acceptable salt thereof, selected from the group consisting of:

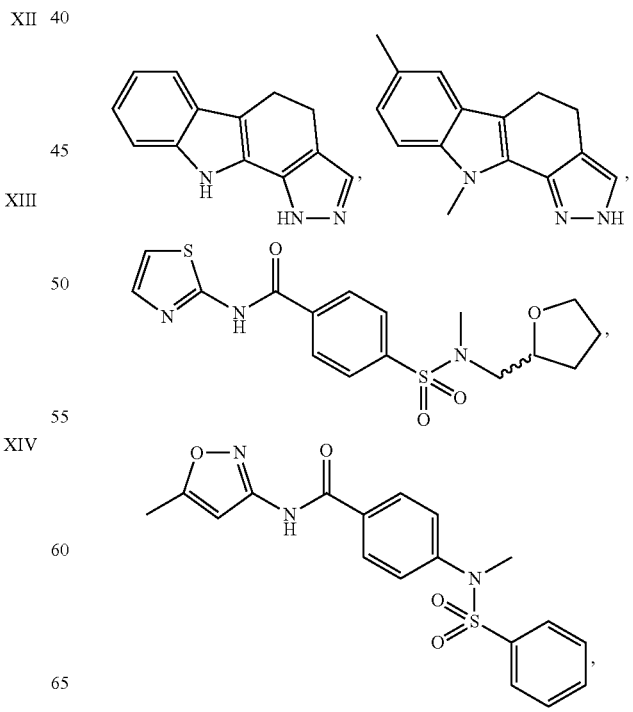

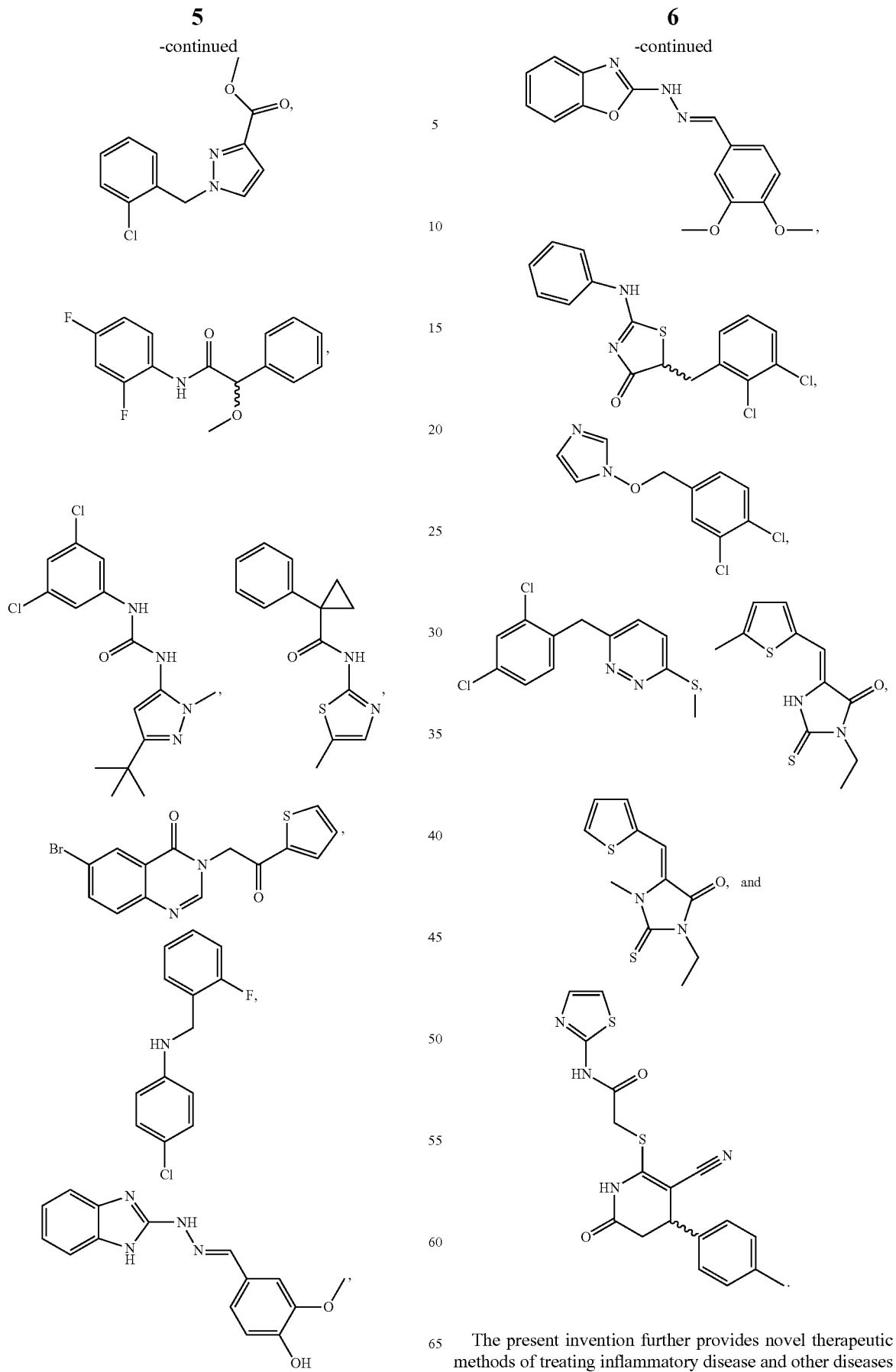
The present invention further provides novel therapeutic methods of treating inflammatory disease and other diseases for inhibition of CD40 mediated TNFα production, comprising administering to a subject, (e.g., a subject in need thereof), an effective amount of a compound of any one of formulas I-XIV.

The present invention further provides novel therapeutic methods of treating inflammatory disease and other diseases for inhibition of CD40 mediated TNFα production, comprising administering to a subject, (e.g., a subject in need thereof), an effective amount of a compound selected from the group consisting of

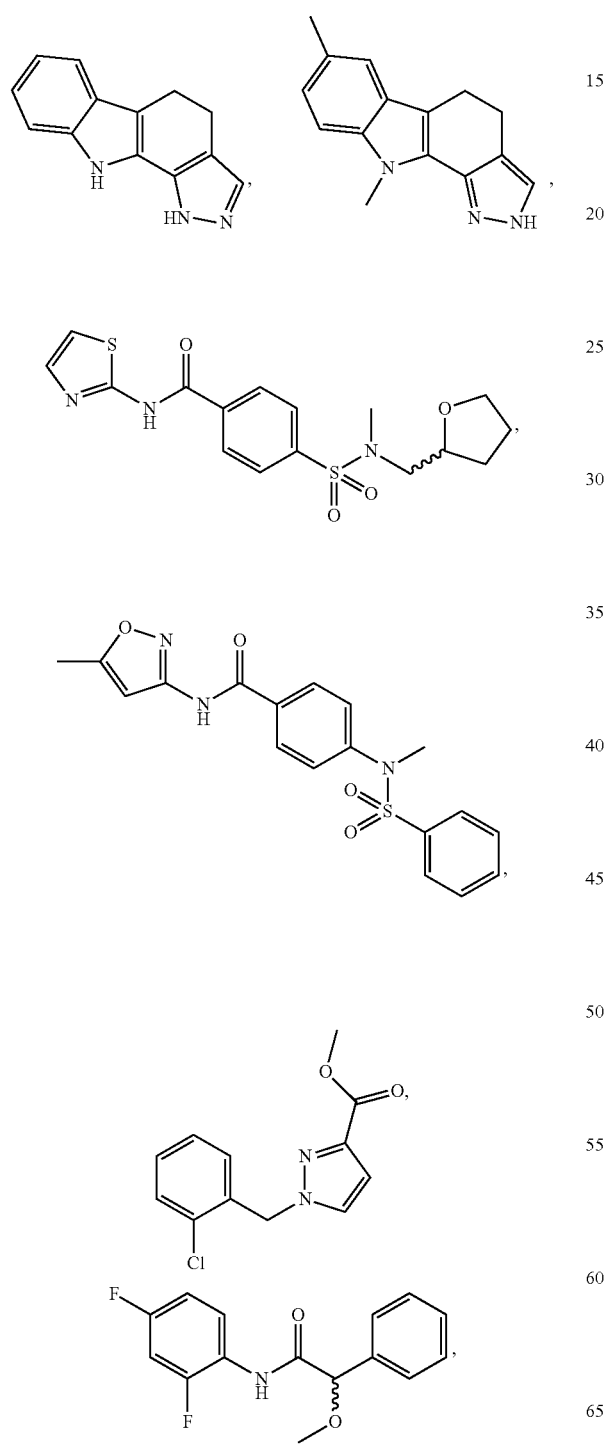

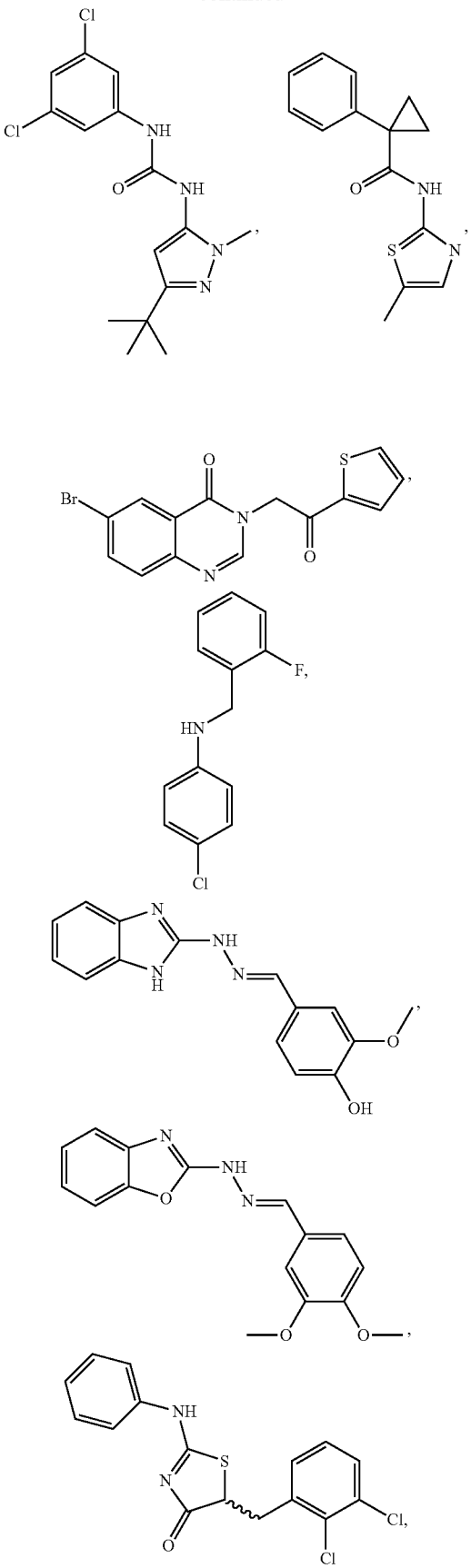

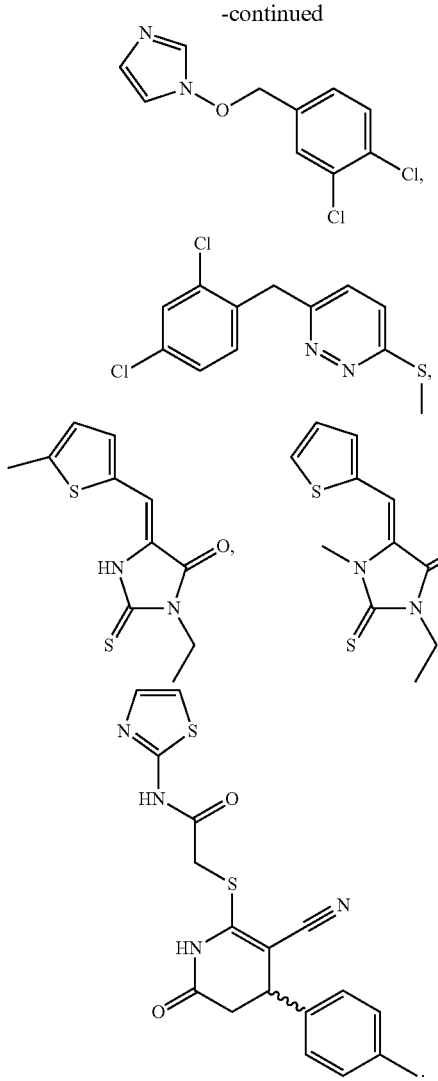
The present invention further provides novel therapeutic methods of treating inflammatory disease and other diseases for inhibition of CD40 mediated TNFα production, comprising administering to a subject, (e.g., a subject in need thereof), an effective amount of a compound selected from the group consisting of:
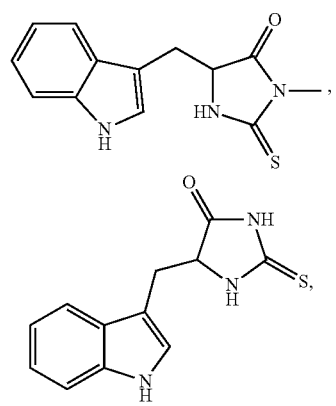
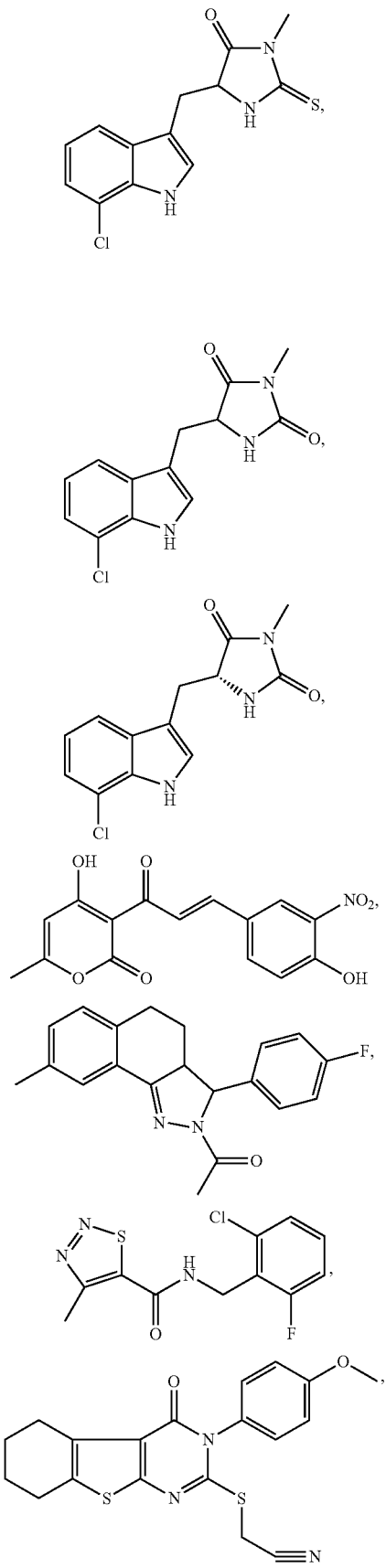

-continued
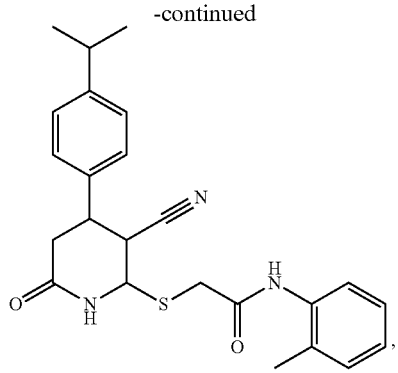
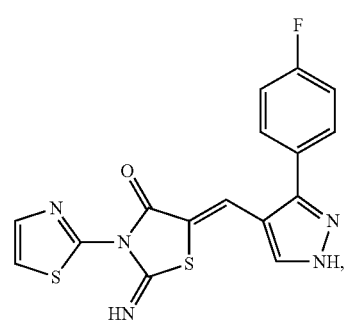
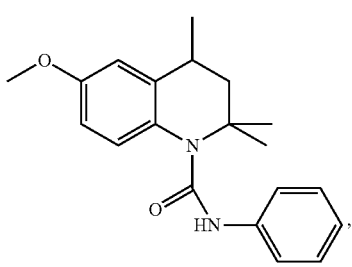
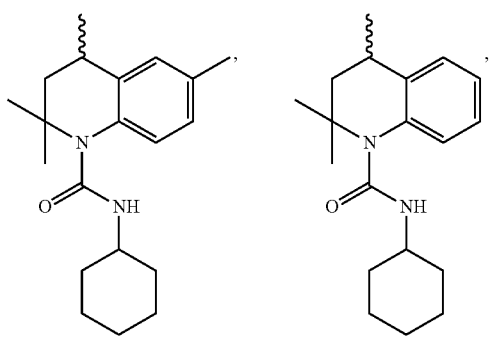
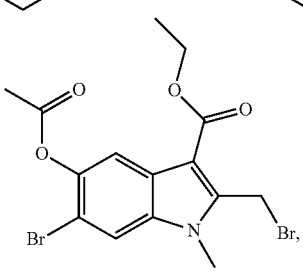
-continued
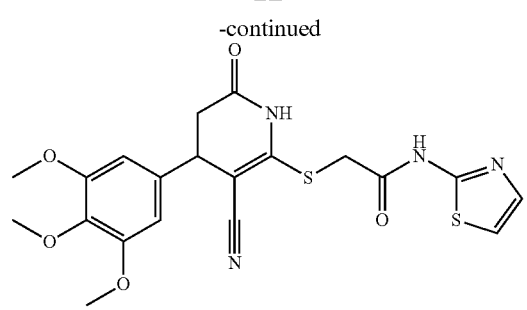
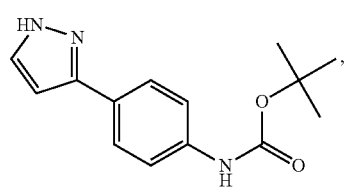
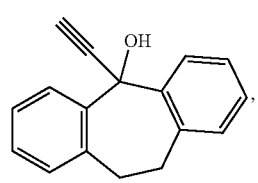
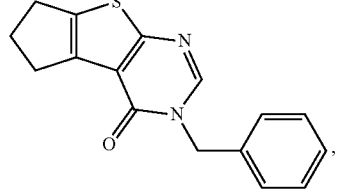
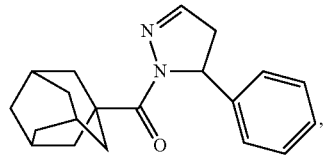
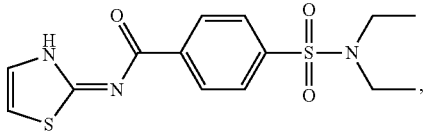
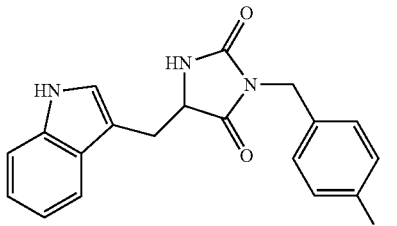
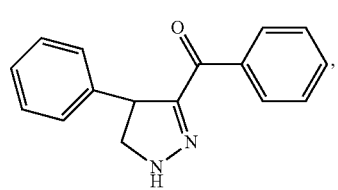

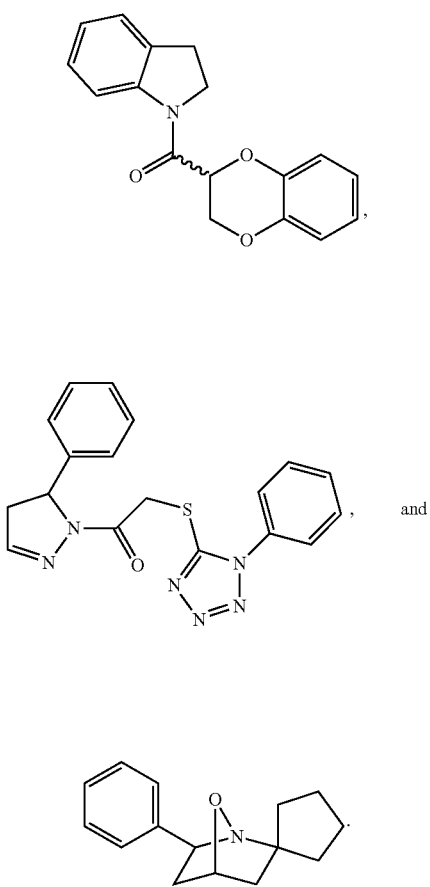

The present invention further provides novel therapeutic methods of treating inflammatory disease and other diseases for inhibition of CD40 mediated TNFα production, comprising administering to a subject, (e.g., a subject in need thereof), an effective amount of a compound selected from the group consisting of:

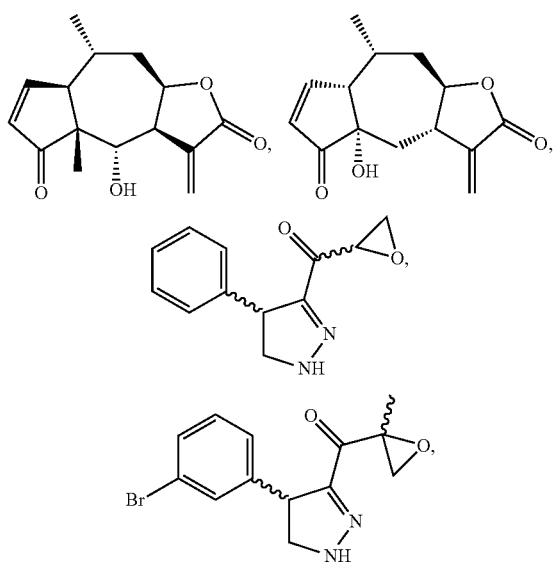

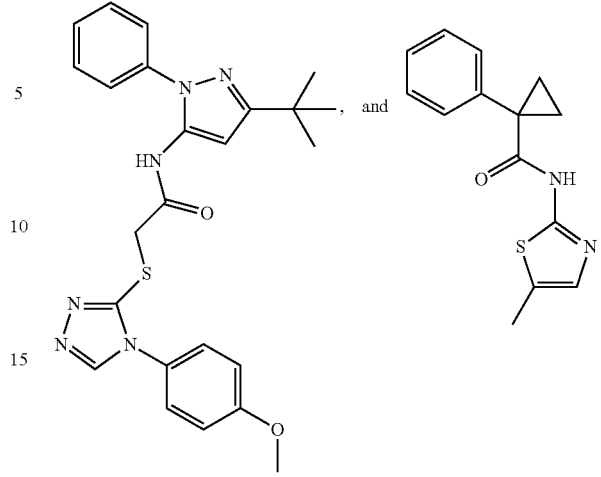

DETAILED DESCRIPTION

Overview

Figure 1:
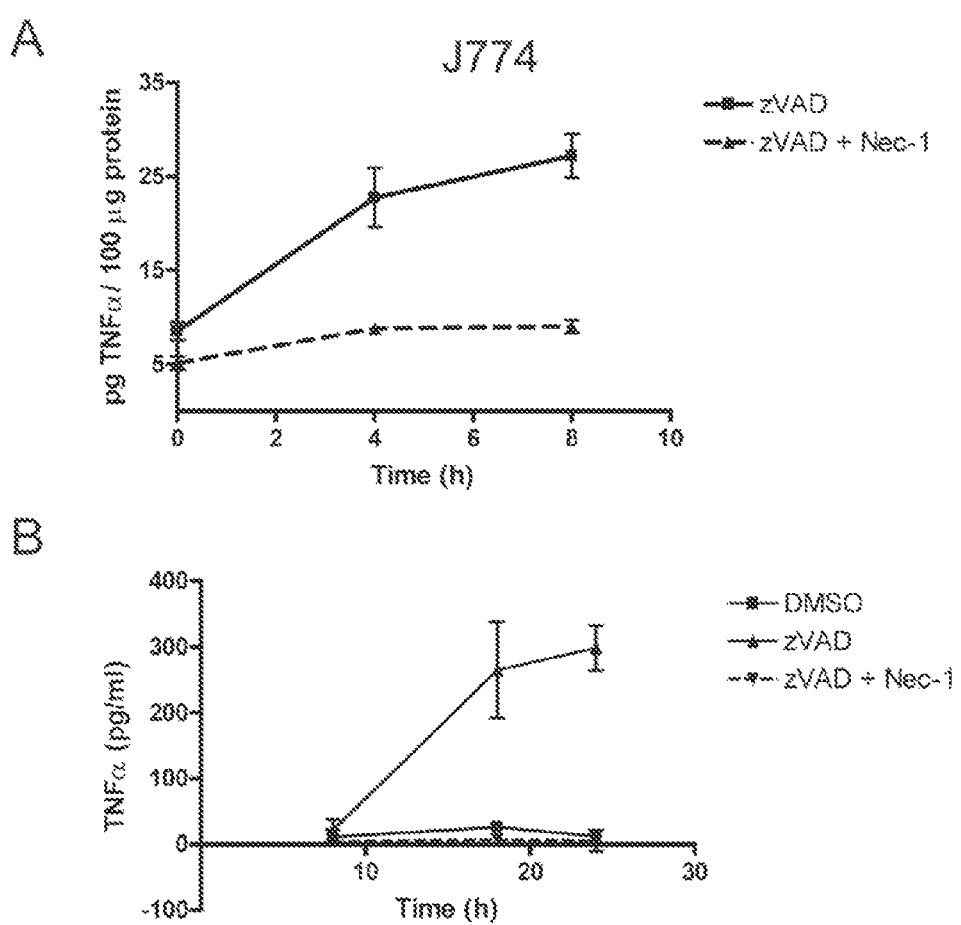
FIG. 1 shows the results of TNFα ELISA assays performed using either the cell lysate (A) or the supernatant (B) of J774 cells treated with 20 μM zVAD.fmk and/or 10 μM Nec-1 for the indicated period of time.

Described herein are novel compositions and methods for the inhibition of necroptosis and the treatment of inflammatory disease. Necroptosis is a programmed necrotic cell pathway that is mediated by RIP1 kinase. Necroptosis is induced in certain cell types by TNFα. As described herein, RIP1 kinase, one of the critical mediators of necroptosis, also mediates TNFα production following antigen presenting cell stimulation with CD154 (CD40 ligand). As is also described herein, various necrostatins (inhibitors of necroptosis) are able to inhibit CD40 mediated TNFα production by antigen presenting cells. Factors involved in the necroptosis pathway, including, for example, RIP1, are therefore also critical for the induction of the inflammatory response. Thus, the necrostatins described herein are useful, for example, in the inhibition of CD40 mediated inflammation and the treatment of inflammatory disease.

Definitions

For convenience, certain terms employed in the specification, examples, and appended claims are collected here. All definitions, as defined and used herein, supersede dictionary definitions, definitions in documents incorporated by reference, and/or ordinary meanings of the defined terms.

The articles "a" and "an" are used herein to refer to one or to more than one (i.e., to at least one) of the grammatical object of the article. By way of example, "an element" means one element or more than one element.

As used herein, the term "administering" means providing a pharmaceutical agent or composition to a subject, and includes, but is not limited to, administering by a medical professional and self-administering.

As used herein, an "effective amount" is an amount effective for treating or preventing a disease such as inflammatory bowel disease (e.g. Crohn's disease, ulcerative colitis), rheumatoid arthritis, psoriatic arthritis, psoriasis, diabetes mellitus, Alzheimer's disease, refractory asthma and vasculitis.

As used herein, the phrase "pharmaceutically acceptable" refers to those agents, compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the phrase "pharmaceutically-acceptable carrier" means a pharmaceutically-acceptable material, composition or vehicle, such as a liquid or solid filler, diluent, excipient, or solvent encapsulating material, involved in carrying or transporting an agent from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

As used herein, the phrase "pharmaceutically-acceptable salts" refers to the relatively non-toxic, inorganic and organic salts of compounds.

As used herein, the term "subject" means a human or non-human animal selected for treatment or therapy.

As used herein, the phrase "subject suspected of having" means a subject exhibiting one or more clinical indicators of a disease or condition.

As used herein, the phrase "subject in need thereof" means a subject identified as in need of a therapy or treatment of the invention.

As used herein, the phrase "therapeutic effect" refers to a local or systemic effect in animals, particularly mammals, and more particularly humans, caused by an agent. The phrases "therapeutically-effective amount" and "effective amount" mean the amount of an agent that produces some desired effect in at least a sub-population of cells. A therapeutically effective amount includes an amount of an agent that produces some desired local or systemic effect at a reasonable benefit/risk ratio applicable to any treatment. For example, certain agents used in the methods of the present invention may be administered in a sufficient amount to produce a reasonable benefit/risk ratio applicable to such treatment.

As used herein, the term "treating" a disease in a subject or "treating" a subject having or suspected of having a disease refers to subjecting the subject to a pharmaceutical treatment, e.g., the administration of one or more agents, such that at least one symptom of the disease is decreased or prevented from worsening.

The definition of each expression, e.g., alkyl, m, n, and the like, when it occurs more than once in any structure, is intended to be independent of its definition elsewhere in the same structure.

It will be understood that "substitution" or "substituted with" includes the implicit proviso that such substitution is in accordance with permitted valence of the substituted atom and the substituent, and that the substitution results in a stable compound, e.g., a compound which does not spontaneously undergo transformation such as by rearrangement, cyclization, elimination, or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein below. The permissible substituents may be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

The term "lower" when appended to any of the groups listed below indicates that the group contains less than seven carbons (i.e. six carbons or less). For example "lower alkyl" refers to an alkyl group containing 1-6 carbons, and "lower alkenyl" refers to an alkyenyl group containing 2-6 carbons.

The term "saturated," as used herein, pertains to compounds and/or groups which do not have any carbon-carbon double bonds or carbon-carbon triple bonds.

The term "unsaturated," as used herein, pertains to compounds and/or groups which have at least one carbon-carbon double bond or carbon-carbon triple bond. The term "aliphatic," as used herein, pertains to compounds and/or groups which are linear or branched, but not cyclic (also known as "acyclic" or "open-chain" groups).

The term "cyclic," as used herein, pertains to compounds and/or groups which have one ring, or two or more rings (e.g., spiro, fused, bridged).

The term "aromatic" refers to a planar or polycyclic structure characterized by a cyclically conjugated molecular moiety containing $4n+2$ electrons, wherein n is the absolute value of an integer. Aromatic molecules containing fused, or joined, rings also are referred to as bicylic aromatic rings. For example, bicyclic aromatic rings containing heteroatoms in a hydrocarbon ring structure are referred to as bicyclic heteroaryl rings.

The term "hydrocarbon" as used herein refers to an organic compound consisting entirely of hydrogen and carbon.

For purposes of this invention, the chemical elements are identified in accordance with the Periodic Table of the Elements, CAS version, Handbook of Chemistry and Physics, 67th Ed., 1986-87, inside cover.

The term "heteroatom" as used herein is art-recognized and refers to an atom of any element other than carbon or hydrogen. Illustrative heteroatoms include boron, nitrogen, oxygen, phosphorus, sulfur and selenium.

The term "alkyl" means an aliphatic or cyclic hydrocarbon radical containing from 1 to 12 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 2-methylcyclopentyl, and 1-cyclohexylethyl.

The term "substituted alkyl" means an aliphatic or cyclic hydrocarbon radical containing from 1 to 12 carbon atoms, substituted with 1, 2, 3, 4, or 5 substituents independently selected from the group consisting of alkyl, alkenyl, alkynyl, halo, haloalkyl, fluoroalkyl, hydroxy, alkoxy, alkyenyloxy, alkynyloxy, carbocyclyloxy, heterocyclyloxy, haloalkoxy, fluoroalkyloxy, sulfhydryl, alkylthio, haloalkylthio, fluoroalkylthio, alkyenylthio, alkynylthio, sulfonic acid, alkylsulfonyl, haloalkylsulfonyl, fluororalkylsulfonyl, alkenylsulfonyl, alkynylsulfonyl, alkoxysulfonyl, haloalkoxysulfonyl, fluororalkoxysulfonyl, alkenyloxysulfonyl, alkynyloxysulfony, aminosulfonyl, sulfinic acid, alkylsulfinyl, haloalkylsulfinyl, fluororalkylsulfinyl, alkenylsulfinyl, alkynylsulfinyl, alkoxysulfinyl, haloalkoxysulfinyl, fluororalkoxysulfinyl, alkenyloxysulfinyl, alkynyloxysulfiny, aminosulfinyl, formyl, alkylcarbonyl, haloalkylcarbonyl, fluoroalkylcarbonyl, alkenylcarbonyl, alkynylcarbonyl, carboxy, alkoxycarbonyl, halo alkoxycarbonyl, fluoroalkoxycarbonyl, alkenyloxycarbonyl, alkynyloxycarbonyl, alkylcarbonyloxy, haloalkylcarbonyloxy, fluoroalkylcarbonyloxy, alkenylcarbonyloxy, alkynylcarbonyloxy, alkylsulfonyloxy, haloalkylsulfonyloxy, fluororalkylsulfonyloxy, alkenylsulfonyloxy, alkynylsulfonyloxy, haloalkoxysulfonyloxy, fluororalkoxysulfonyloxy, alkenyloxysulfonyloxy, alkynyloxysulfonyloxy, alkylsulfinyloxy, halo alkylsulfinyloxy, fluororalkylsulfinyloxy, alkenylsulfinyloxy, alkynylsulfinyloxy, alkoxysulfinyloxy, halo alkoxysulfinyloxy, fluororalkoxysulfinyloxy, alkenyloxysulfinyloxy, alkynyloxysulfinyloxy, aminosulfinyloxy, amino, amido, aminosulfonyl, aminosulfinyl, cyano, nitro, azido, phosphinyl, phosphoryl, silyl and silyloxy.

The term "alkylene" is art-recognized, and as used herein pertains to a bidentate moiety obtained by removing two hydrogen atoms of an alkyl group, as defined above.

The term "alkenyl" as used herein means a straight or branched chain hydrocarbon containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkynyl" as used herein means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "carbocyclyl" as used herein means monocyclic or multicyclic (e.g., bicyclic, tricyclic, etc.) hydrocarbons containing from 3 to 12 carbon atoms that is completely saturated or has one or more unsaturated bonds, and for the avoidance of doubt, the degree of unsaturation does not result in an aromatic ring system (e.g. phenyl). Examples of carbocyclyl groups include 1-cyclopropyl, 1-cyclobutyl, 2-cyclopentyl, 1-cyclopentenyl, 3-cyclohexyl, 1-cyclohexenyl and 2-cyclopentenylmethyl.

The term "heterocyclyl", as used herein include non-aromatic, ring systems, including, but not limited to, monocyclic, bicyclic (e.g. fused and spirocyclic) and tricyclic rings, which can be completely saturated or which can contain one or more units of unsaturation, for the avoidance of doubt, the degree of unsaturation does not result in an aromatic ring system, and have 3 to 12 atoms including at least one heteroatom, such as nitrogen, oxygen, or sulfur. For purposes of exemplification, which should not be construed as limiting the scope of this invention, the following are examples of heterocyclic rings: azepines, azetidinyl, morpholinyl, oxopiperidinyl, oxopyrrolidinyl, piperazinyl, piperidinyl, pyrrolidinyl, quinicludinyl, thiomorpholinyl, tetrahydropyranyl and tetrahydrofuranyl. The heterocyclyl groups of the invention are substituted with 0, 1, 2, 3, 4 or 5 substituents independently selected from the group consisting of alkyl, alkenyl, alkynyl, halo, haloalkyl, fluoroalkyl, hydroxy, alkoxy, alkyenyloxy, alkynyloxy, carbocyclyloxy, heterocyclyloxy, haloalkoxy, fluoroalkyloxy, sulfhydryl, alkylthio, haloalkylthio, fluoroalkylthio, alkyenylthio, alkynylthio, sulfonic acid, alkylsulfonyl, haloalkylsulfonyl, fluororalkylsulfonyl, alkenylsulfonyl, alkynylsulfonyl, alkoxysulfonyl, halo alkoxysulfonyl, fluororalkoxysulfonyl, alkenyloxysulfonyl, alkynyloxysulfony, aminosulfonyl, sulfinic acid, alkylsulfinyl, haloalkylsulfinyl, fluororalkylsulfinyl, alkenylsulfinyl, alkynylsulfinyl, alkoxysulfinyl, haloalkoxysulfinyl, fluororalkoxysulfinyl, alkenyloxysulfinyl, alkynyloxysulfiny, aminosulfinyl, formyl, alkylcarbonyl, haloalkylcarbonyl, fluoroalkylcarbonyl, alkenylcarbonyl, alkynylcarbonyl, carboxy, alkoxycarbonyl, halo alkoxycarbonyl, fluoroalkoxycarbonyl, alkenyloxycarbonyl, alkynyloxycarbonyl, alkylcarbonyloxy, haloalkylcarbonyloxy, fluoroalkylcarbonyloxy, alkenylcarbonyloxy, alkynylcarbonyloxy, alkylsulfonyloxy, halo alkylsulfonyloxy, fluororalkylsulfonyloxy, alkenylsulfonyloxy, alkynylsulfonyloxy, haloalkoxysulfonyloxy, fluororalkoxysulfonyloxy, alkenyloxysulfonyloxy, alkynyloxysulfonyloxy, alkylsulfinyloxy, halo alkylsulfinyloxy, fluororalkylsulfinyloxy, alkenylsulfinyloxy, alkynylsulfinyloxy, alkoxysulfinyloxy, haloalkoxysulfinyloxy, fluororalkoxysulfinyloxy, alkenyloxysulfinyloxy, alkynyloxysulfinyloxy, aminosulfinyloxy, amino, amido, aminosulfonyl, aminosulfinyl, cyano, nitro, azido, phosphinyl, phosphoryl, silyl, silyloxy, and any of said substituents bound to the heterocyclyl group through an alkylene moiety (e.g. methylene).

The term "N-heterocyclyl" as used herein is a subset of heterocyclyl, as defined herein, which have at least one nitrogen atom through which the N-heterocyclyl moiety is bound to the parent moiety. Representative examples include pyrrolidin-1-yl, piperidin-1-yl, piperazin-1-yl, hexahydropyrimidin-1-yl, morpholin-1-yl, 1,3-oxazinan-3-yl and 6-azaspiro[2.5]oct-6-yl. As with the heterocyclyl groups, the N-heterocyclyl groups of the invention are substituted with 0, 1, 2, 3, 4 or 5 substituents independently selected from the group consisting of alkyl, alkenyl, alkynyl, halo, haloalkyl, fluoroalkyl, hydroxy, alkoxy, alkyenyloxy, alkynyloxy, carbocyclyloxy, heterocyclyloxy, haloalkoxy, fluoroalkyloxy, sulfhydryl, alkylthio, haloalkylthio, fluoroalkylthio, alkylthio, alkyenylthio, alkynylthio, sulfonic acid, alkylsulfonyl, haloalkylsulfonyl, fluororalkylsulfonyl, alkenylsulfonyl, alkynylsulfonyl, alkoxysulfonyl, halo alkoxysulfonyl, fluororalkoxysulfonyl, alkenyloxysulfonyl, alkynyloxysulfony, aminosulfonyl, sulfinic acid, alkylsulfinyl, haloalkylsulfinyl, fluororalkylsulfinyl, alkenylsulfinyl, alkynylsulfinyl, alkoxysulfinyl, haloalkoxysulfinyl, fluororalkoxysulfinyl, alkenyloxysulfinyl, alkynyloxysulfiny, aminosulfinyl, formyl, alkylcarbonyl, haloalkylcarbonyl, fluoroalkylcarbonyl, alkenylcarbonyl, alkynylcarbonyl, carboxy, alkoxycarbonyl, haloalkoxycarbonyl, fluoroalkoxycarbonyl, alkenyloxycarbonyl, alkynyloxycarbonyl, alkylcarbonyloxy, halo alkylcarbonyloxy, fluoroalkylcarbonyloxy, alkenylcarbonyloxy, alkynylcarbonyloxy, alkylsulfonyloxy, halo alkylsulfonyloxy, fluororalkylsulfonyloxy, alkenylsulfonyloxy, alkynylsulfonyloxy, haloalkoxysulfonyloxy, fluororalkoxysulfonyloxy, alkenyloxysulfonyloxy, alkynyloxysulfonyloxy, alkylsulfinyloxy, halo alkylsulfinyloxy, fluororalkylsulfinyloxy, alkenylsulfinyloxy, alkynylsulfinyloxy, alkoxysulfinyloxy, haloalkoxysulfinyloxy, fluororalkoxysulfinyloxy, alkenyloxysulfinyloxy, alkynyloxysulfinyloxy, aminosulfinyloxy, amino, amido, aminosulfonyl, aminosulfinyl, cyano, nitro, azido, phosphinyl, phosphoryl, silyl, silyloxy, and any of said substituents bound to the N-heterocyclyl group through an alkylene moiety (e.g. methylene).

The term "aryl," as used herein means a phenyl group, naphthyl or anthracenyl group. The aryl groups of the present invention can be optionally substituted with 1, 2, 3, 4 or 5 substituents independently selected from the group consisting of alkyl, alkenyl, alkynyl, halo, haloalkyl, fluoroalkyl, hydroxy, alkoxy, alkyenyloxy, alkynyloxy, carbocyclyloxy, heterocyclyloxy, haloalkoxy, fluoroalkyloxy, sulfhydryl, alkylthio, haloalkylthio, fluoroalkylthio, alkyenylthio, alkynylthio, sulfonic acid, alkylsulfonyl, haloalkylsulfonyl, fluororalkylsulfonyl, alkenylsulfonyl, alkynylsulfonyl, alkoxysulfonyl, haloalkoxysulfonyl, fluororalkoxysulfonyl, alkenyloxysulfonyl, alkynyloxysulfony, aminosulfonyl, sulfinic acid, alkylsulfinyl, haloalkylsulfinyl, fluororalkylsulfinyl, alkenylsulfinyl, alkynylsulfinyl, alkoxysulfinyl, haloalkoxysulfinyl, fluororalkoxysulfinyl, alkenyloxysulfinyl, alkynyloxysulfiny, aminosulfinyl, formyl, alkylcarbonyl, haloalkylcarbonyl, fluoroalkylcarbonyl, alkenylcarbonyl, alkynylcarbonyl, carboxy, alkoxycarbonyl, haloalkoxycarbonyl, fluoroalkoxycarbonyl, alkenyloxycarbonyl, alkynyloxycarbonyl, alkylcarbonyloxy, halo alkylcarbonyloxy, fluoroalkylcarbonyloxy, alkenylcarbonyloxy, alkynylcarbonyloxy, alkylsulfonyloxy, halo alkylsulfonyloxy, fluororalkylsulfonyloxy, alkenylsulfonyloxy, alkynylsulfonyloxy, haloalkoxysulfonyloxy, fluororalkoxysulfonyloxy, alkenyloxysulfonyloxy, alkynyloxysulfonyloxy, alkylsulfinyloxy, halo alkylsulfinyloxy, fluororalkylsulfinyloxy, alkenylsulfinyloxy, alkynylsulfinyloxy, alkoxysulfinyloxy, haloalkoxysulfinyloxy, fluororalkoxysulfinyloxy, alkenyloxysulfinyloxy, alkynyloxysulfinyloxy, aminosulfinyloxy, amino, amido, aminosulfonyl, aminosulfinyl, cyano, nitro, azido, phosphinyl, phosphoryl, silyl, silyloxy, and any of said substituents bound to the heterocyclyl group through an alkylene moiety (e.g. methylene).

The term "arylene," is art-recognized, and as used herein pertains to a bidentate moiety obtained by removing two hydrogen atoms of an aryl ring, as defined above.

The term "arylalkyl" or "aralkyl" as used herein means an aryl group, as defined herein, appended to the parent molecular moiety through an alkyl group, as defined herein.

Representative examples of aralkyl include, but are not limited to, benzyl, 2-phenylethyl, 3-phenylpropyl, and 2-naphth-2-ylethyl.

The term "biaryl," as used herein means an aryl-substituted aryl, an aryl-substituted heteroaryl, a heteroaryl-substituted aryl or a heteroaryl-substituted heteroaryl, wherein aryl and heteroaryl are as defined herein. Representative examples include 4-(phenyl)phenyl and 4-(4-fluorophenyl)pyridinyl.

The term "heteroaryl" as used herein include aromatic ring systems, including, but not limited to, monocyclic, bicyclic and tricyclic rings, and have 3 to 12 atoms including at least one heteroatom, such as nitrogen, oxygen, or sulfur. For purposes of exemplification, which should not be construed as limiting the scope of this invention: azaindolyl, benzo(b)thienyl, benzimidazolyl, benzofuranyl, benzoxazolyl, benzothiazolyl, benzothiadiazolyl, benzotriazolyl, benzoxadiazolyl, furanyl, imidazolyl, imidazopyridinyl, indolyl, indolinyl, indazolyl, isoindolinyl, isoxazolyl, isothiazolyl, isoquinolinyl, oxadiazolyl, oxazolyl, purinyl, pyranyl, pyrazinyl, pyrazolyl, pyridinyl, pyrimidinyl, pyrrolyl, pyrrolo[2,3-d]pyrimidinyl, pyrazolo[3,4-d]pyrimidinyl, quinolinyl, quinazolinyl, triazolyl, thiazolyl, thiophenyl, tetrahydroindolyl, tetrazolyl, thiadiazolyl, thienyl, thiomorpholinyl, triazolyl or tropanyl. The heteroaryl groups of the invention are substituted with 0, 1, 2, 3, 4 or 5 substituents independently selected from the group consisting of alkyl, alkenyl, alkynyl, halo, haloalkyl, fluoroalkyl, hydroxy, alkoxy, alkyenyloxy, alkynyloxy, carbocyclyloxy, heterocyclyloxy, haloalkoxy, fluoroalkyloxy, sulfhydryl, alkylthio, haloalkylthio, fluoroalkylthio, alkyenylthio, alkynylthio, sulfonic acid, alkylsulfonyl, haloalkylsulfonyl, fluororalkylsulfonyl, alkenylsulfonyl, alkynylsulfonyl, alkoxysulfonyl, halo alkoxysulfonyl, fluororalkoxysulfonyl, alkenyloxysulfonyl, alkynyloxysulfony, aminosulfonyl, sulfinic acid, alkylsulfinyl, haloalkylsulfinyl, fluororalkylsulfinyl, alkenylsulfinyl, alkynylsulfinyl, alkoxysulfinyl, haloalkoxysulfinyl, fluororalkoxysulfinyl, alkenyloxysulfinyl, alkynyloxysulfiny, aminosulfinyl, formyl, alkylcarbonyl, haloalkylcarbonyl, fluoroalkylcarbonyl, alkenylcarbonyl, alkynylcarbonyl, carboxy, alkoxycarbonyl, haloalkoxycarbonyl, fluoroalkoxycarbonyl, alkenyloxycarbonyl, alkynyloxycarbonyl, alkylcarbonyloxy, halo alkylcarbonyloxy, fluoroalkylcarbonyloxy, alkenylcarbonyloxy, alkynylcarbonyloxy, alkylsulfonyloxy, haloalkylsulfonyloxy, fluororalkylsulfonyloxy, alkenylsulfonyloxy, alkynylsulfonyloxy, haloalkoxysulfonyloxy, fluororalkoxysulfonyloxy, alkenyloxysulfonyloxy, alkynyloxysulfonyloxy, alkylsulfinyloxy, halo alkylsulfinyloxy, fluororalkylsulfinyloxy, alkenylsulfinyloxy, alkynylsulfinyloxy, alkoxysulfinyloxy, haloalkoxysulfinyloxy, fluororalkoxysulfinyloxy, alkenyloxysulfinyloxy, alkynyloxysulfinyloxy, aminosulfinyloxy, amino, amido, aminosulfonyl, aminosulfinyl, cyano, nitro, azido, phosphinyl, phosphoryl, silyl, silyloxy, and any of said substituents bound to the heteroaryl group through an alkylene moiety (e.g. methylene).

The term "heteroarylene," is art-recognized, and as used herein pertains to a bidentate moiety obtained by removing two hydrogen atoms of a heteroaryl ring, as defined above.

The term "heteroarylalkyl" or "heteroaralkyl" as used herein means a heteroaryl, as defined herein, appended to the parent molecular moiety through an alkyl group, as defined herein. Representative examples of heteroarylalkyl include, but are not limited to, pyridin-3-ylmethyl and 2-(thien-2-yl)ethyl.

The term "halo" or "halogen" means —Cl, —Br, —I or —F.

The term "haloalkyl" means an alkyl group, as defined herein, wherein at least one hydrogen is replaced with a halogen, as defined herein. Representative examples of haloalkyl include, but are not limited to, chloromethyl, 2-fluoroethyl, trifluoromethyl, pentafluoroethyl, and 2-chloro-3-fluoropentyl.

The term "fluoroalkyl" means an alkyl group, as defined herein, wherein all the hydrogens are replaced with fluorines.

The term "hydroxy" as used herein means an —OH group.

The term "alkoxy" or "alkyloxy" as used herein means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy. The terms "alkyenyloxy", "alkynyloxy", "carbocyclyloxy", and "heterocyclyloxy" are likewise defined.

The term "haloalkoxy" as used herein means an alkoxy group, as defined herein, wherein at least one hydrogen is replaced with a halogen, as defined herein. Representative examples of haloalkoxy include, but are not limited to, chloromethoxy, 2-fluoroethoxy, trifluoromethoxy, and pentafluoroethoxy. The term "fluoroalkyloxy" is likewise defined.

The term "aryloxy" as used herein means an aryl group, as defined herein, appended to the parent molecular moiety through an oxygen. The term "heteroaryloxy" as used herein means a heteroaryl group, as defined herein, appended to the parent molecular moiety through an oxygen. The terms "heteroaryloxy" is likewise defined.

The term "arylalkoxy" or "arylalkyloxy" as used herein means an arylalkyl group, as defined herein, appended to the parent molecular moiety through an oxygen. The term "heteroarylalkoxy" is likewise defined. Representative examples of aryloxy and heteroarylalkoxy include, but are not limited to, 2-chlorophenylmethoxy, 3-trifluoromethylphenylethoxy, and 2,3-dimethylpyridinylmethoxy.

The term "sulfhydryl" or "thio" as used herein means a —SH group.

The term "alkylthio" as used herein means an alkyl group, as defined herein, appended to the parent molecular moiety through a sulfur. Representative examples of alkylthio include, but are not limited, methylthio, ethylthio, tert-butylthio, and hexylthio. The terms "haloalkylthio", "fluoroalkylthio", "alkyenylthio", "alkynylthio", "carbocyclylthio", and "heterocyclylthio" are likewise defined.

The term "arylthio" as used herein means an aryl group, as defined herein, appended to the parent molecular moiety through an sulfur. The term "heteroarylthio" is likewise defined.

The term "arylalkylthio" or "aralkylthio" as used herein means an arylalkyl group, as defined herein, appended to the parent molecular moiety through an sulfur. The term "heteroarylalkylthio" is likewise defined.

The term "sulfonyl" as used herein refers to —S(=O)$_2$— group.

The term "sulfonic acid" as used herein refers to —S(=O)$_2$OH.

The term "alkylsulfonyl" as used herein means an alkyl group, as defined herein, appended to the parent molecular moiety through a sulfonyl group, as defined herein. Representative examples of alkylsulfonyl include, but are not limited to, methylsulfonyl and ethylsulfonyl. The terms "haloalkylsulfonyl", "fluororalkylsulfonyl", "alkenylsulfonyl", "alkynylsulfonyl", "carbocyclylsulfonyl", "heterocyclylsulfonyl", "arylsulfonyl", "aralkylsulfonyl", "heteroarylsulfonyl" and "heteroaralkylsulfonyl" are likewise defined.

The term "alkoxysulfonyl" as used herein means an alkoxy group, as defined herein, appended to the parent molecular moiety through a sulfonyl group, as defined herein. Representative examples of alkoxysulfonyl include, but are not limited to, methoxysulfonyl, ethoxysulfonyl and propoxysulfonyl. The terms "haloalkoxysulfonyl", "fluoroalkoxysulfonyl", "alkenyloxysulfonyl", "alkynyloxysulfonyl", "carbocyclyloxysulfonyl", "heterocyclyloxysulfonyl", "aryloxysulfonyl", "aralkyloxysulfonyl", "heteroaryloxysulfonyl" and "heteroaralkyloxysulfonyl" are likewise defined.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The term "aminosulfonyl" as used herein means an amino group, as defined herein, appended to the parent molecular moiety through a sulfonyl group.

The term "sulfinyl" as used herein refers to —S(=O)— group. Sulfinyl groups are as defined above for sulfonyl groups. The term "sulfinic acid" as used herein refers to —S(=O)OH.

The term "oxy" refers to a —O— group.

The term "carbonyl" as used herein means a —C(=O)— group.

The term "thiocarbonyl" as used herein means a —C(=S)— group.

The term "formyl" as used herein means a —C(=O)H group.

The term "alkylcarbonyl" as used herein means an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl. The terms "haloalkylcarbonyl", "fluoroalkylcarbonyl", "alkenylcarbonyl", "alkynylcarbonyl", "carbocyclylcarbonyl", "heterocyclylcarbonyl", "arylcarbonyl", "aralkylcarbonyl", "heteroarylcarbonyl", and "heteroaralkylcarbonyl" are likewise defined.

The term "carboxy" as used herein means a —CO$_2$H group.

The term "alkoxycarbonyl" as used herein means an alkoxy group, as defined herein, appended to the parent molecular moiety through a carbonyl group, as defined herein. Representative examples of alkoxycarbonyl include, but are not limited to, methoxycarbonyl, ethoxycarbonyl, and tert-butoxycarbonyl. The terms "haloalkoxycarbonyl", "fluoroalkoxycarbonyl", "alkenyloxycarbonyl", "alkynyloxycarbonyl", "carbocyclyloxycarbonyl", "heterocyclyloxycarbonyl", "aryloxycarbonyl", "aralkyloxycarbonyl", "heteroaryloxycarbonyl", and "heteroaralkyloxycarbonyl" are likewise defined.

The term "alkylcarbonyloxy" as used herein means an alkylcarbonyl group, as defined herein, appended to the parent molecular moiety through an oxygen atom. Representative examples of alkylcarbonyloxy include, but are not limited to, acetyloxy, ethylcarbonyloxy, and tert-butylcarbonyloxy. The terms "haloalkylcarbonyloxy", "fluoroalkylcarbonyloxy", "alkenylcarbonyloxy", "alkynylcarbonyloxy", "carbocyclylcarbonyloxy", "heterocyclylcarbonyloxy", "arylcarbonyloxy", "aralkylcarbonyloxy", "heteroarylcarbonyloxy", and "heteroaralkylcarbonyloxy" are likewise defined.

The term "alkylsulfonyloxy" as used herein means an alkylsulfonyl group, as defined herein, appended to the parent molecular moiety through an oxygen atom. The terms "haloalkylsulfonyloxy", "fluororalkylsulfonyloxy", "alkenylsulfonyloxy", "alkynylsulfonyloxy", "carbocyclylsulfonyloxy", "heterocyclylsulfonyloxy", "arylsulfonyloxy", "aralkylsulfonyloxy", "heteroarylsulfonyloxy", "heteroaralkylsulfonyloxy", "haloalkoxysulfonyloxy", "fluororalkoxysulfonyloxy", "alkenyloxysulfonyloxy", "alkynyloxysulfonyloxy", "carbocyclyloxysulfonyloxy", "heterocyclyloxysulfonyloxy", "aryloxysulfonyloxy", "aralkyloxysulfonyloxy", "heteroaryloxysulfonyloxy" and "heteroaralkyloxysulfonyloxy"

The term "amino" as used herein refers to —NH$_2$ and substituted derivatives thereof wherein one or both of the hydrogens are independently replaced with substituents selected from the group consisting of alkyl, haloalkyl, fluoroalkyl, alkenyl, alkynyl, carbocyclyl, heterocyclyl, aryl, aralkyl, heteroaryl, heteroaralkyl, alkylcarbonyl, haloalkylcarbonyl, fluoroalkylcarbonyl, alkenylcarbonyl, alkynylcarbonyl, carbocyclylcarbonyl, heterocyclylcarbonyl, arylcarbonyl, aralkylcarbonyl, heteroarylcarnbonyl, heteroaralkylcarbonyl and the sulfonyl and sulfinyl groups defined above; or when both hydrogens together are replaced with an alkylene group (to form a ring which contains the nitrogen). Representative examples include, but are not limited to methylamino, acetylamino, and dimethylamino.

The term "amido" as used herein means an amino group, as defined herein, appended to the parent molecular moiety through a carbonyl.

The term "cyano" as used herein means a —C≡N group.

The term "nitro" as used herein means a —NO$_2$ group.

The term "azido" as used herein means a —N$_3$ group.

The term "phosphinyl" as used herein includes —PH$_3$ and substituted derivatives thereof wherein one, two or three of the hydrogens are independently replaced with substituents selected from the group consisting of alkyl, haloalkyl, fluoroalkyl, alkenyl, alkynyl, carbocyclyl, heterocyclyl, aryl, aralkyl, heteroaryl, heteroaralkyl, alkoxy, haloalkoxy, fluoroalkyloxy, alkenyloxy, alkynyloxy, carbocyclyloxy, heterocyclyloxy, aryloxy, aralkyloxy, heteroaryloxy, heteroaralkyloxy, and amino.

The term "phosphoryl" as used herein refers to —P(=O)OH$_2$ and substituted derivatives thereof wherein one or both of the hydroxyls are independently replaced with substituents selected from the group consisting of alkyl, haloalkyl, fluoroalkyl, alkenyl, alkynyl, carbocyclyl, heterocyclyl, aryl, aralkyl, heteroaryl, heteroaralkyl, alkoxy, haloalkoxy, fluoroalkyloxy, alkenyloxy, alkynyloxy, carbocyclyloxy, heterocyclyloxy, aryloxy, aralkyloxy, heteroaryloxy, heteroaralkyloxy, and amino.

The term "silyl" as used herein includes H$_3$Si— and substituted derivatives thereof wherein one, two or three of the hydrogens are independently replaced with substituents selected from alkyl, haloalkyl, fluoroalkyl, alkenyl, alkynyl, carbocyclyl, heterocyclyl, aryl, aralkyl, heteroaryl, and heteroaralkyl. Representative examples include trimethylsilyl (TMS), tert-butyldiphenylsilyl (TBDPS), tert-butyldimethylsilyl (TBS/TBDMS), triisopropylsilyl (TIPS), and [2-(trimethylsilyl)ethoxy]methyl (SEM).

The term "silyloxy" as used herein means a silyl group, as defined herein, is appended to the parent molecule through an oxygen atom.

The abbreviations Me, Et, Ph, Tf, Nf, Ts, and Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled Standard List of Abbreviations.

Selected Necrostatin Compounds

In certain embodiments, the present invention relates to a compound selected from the group consisting of a compound of any one of formulas I-XIV:

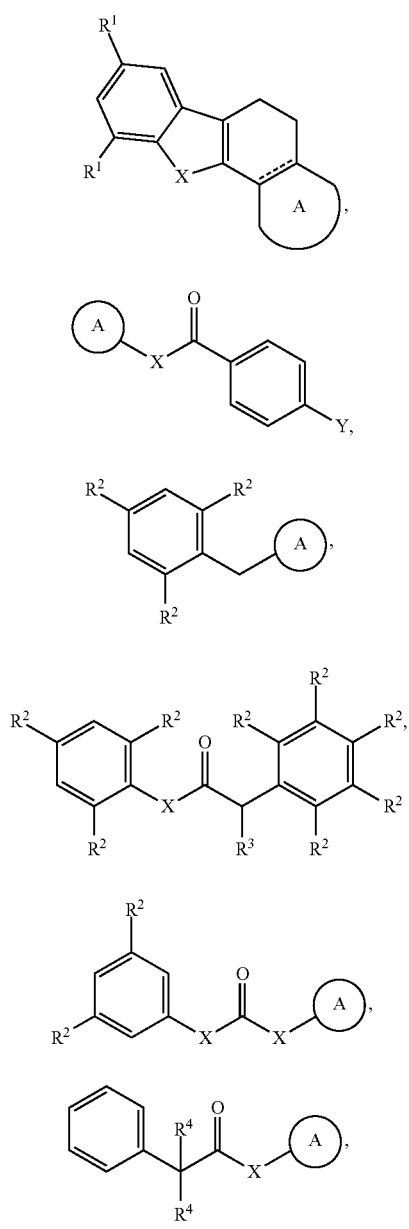

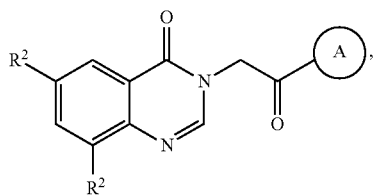

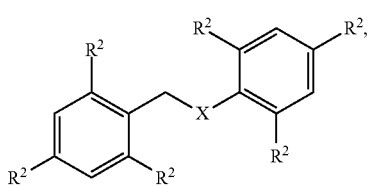

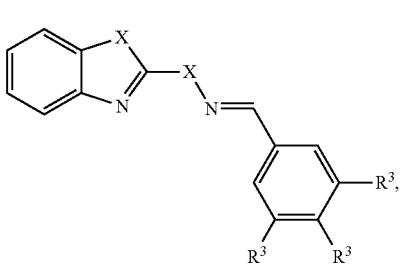

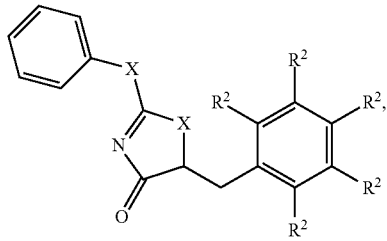

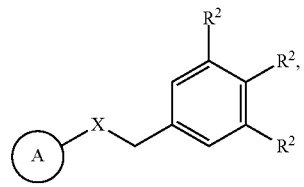

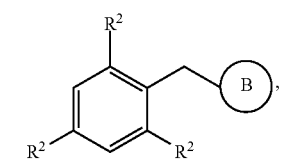

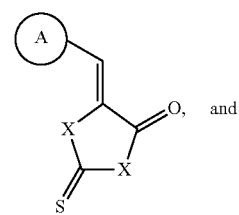

-continued

XIV or a pharmaceutically acceptable salt thereof,
wherein, independently for each occurrence,
Y represents Ⓐ represents a substituted or unsubstituted 5-membered heteroaryl;
Ⓑ represents a substituted 6-membered heteroaryl;
Ⓒ represents an unsubstituted 5-membered heterocyclyl;
⇝ represents a double bond or a single bond;
$R^1$ is —H or alkyl;
$R^2$ is —H, alkyl, halo, or hydroxy;
$R^3$ is —H, alkyloxy, hydroxy, or —$SR^1$;
$R^4$ is —H or alkyl, or any two instances of $R^4$, taken together, form a ring;
$R^5$ is cyano, —C(=O)$R^6$; or —$NO_2$;
$R^6$ is —H, —N($R^1$)$_2$, hydroxy, alkyloxy, or alkyl; and
X represents —O—, —$NR^1$—, or —S—;
wherein Ⓑ or Ⓒ may be substituted with any of alkyl, halo, hydroxy, alkyloxy, —$SR^1$, cyano, —C(=O)$R^6$, —$NO_2$, or —N($R^1$)$_2$.

In certain embodiments, the present invention relates to a compound of formula I

I or a pharmaceutically acceptable salt thereof,
wherein, independently for each occurrence,
Ⓐ represents a substituted or unsubstituted 5-membered heteroaryl;
⇝ represents a double bond or a single bond;
$R^1$ is —H or alkyl; and
X represents —O—, —$NR^1$—, or —S—.

In certain embodiments, the present invention relates to any one of the aforementioned compounds, wherein Ⓐ represents an unsubstituted 5-membered heteroaryl. In certain embodiments, the present invention relates to any one of the aforementioned compounds, wherein Ⓐ represents In certain embodiments, the present invention relates to any one of the aforementioned compounds, wherein Ⓐ represents In certain embodiments, the present invention relates to any one of the aforementioned compounds, wherein X represents —$NR^1$—. In certain embodiments, the present invention relates to any one of the aforementioned compounds, wherein X represents —NH—. In certain embodiments, the present invention relates to any one of the aforementioned compounds, wherein X represents —N(CH$_3$)—.

In certain embodiments, the present invention relates to any one of the aforementioned compounds, wherein at least one instance of $R^1$ is alkyl. In certain embodiments, the present invention relates to any one of the aforementioned compounds, wherein $R^1$ is methyl, ethyl, n-propyl, or isopropyl. In certain embodiments, the present invention relates to any one of the aforementioned compounds, wherein one instance of $R^1$ is methyl, ethyl, n-propyl, or isopropyl. In certain embodiments, the present invention relates to any one of the aforementioned compounds, wherein at least one instance of $R^1$ is methyl.

In certain embodiments, the present invention relates to a compound of formula II

II or a pharmaceutically acceptable salt thereof, wherein, independently for each occurrence,
Y represents

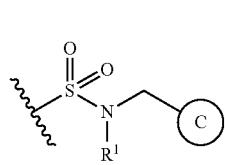 or 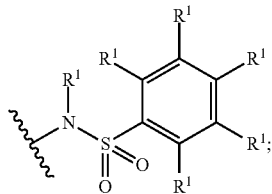;

Ⓐ represents a substituted or unsubstituted 5-membered heteroaryl;
Ⓒ represents an unsubstituted 5-membered heterocyclyl;
$R^1$ is —H or alkyl;
$R^6$ is —H, —N($R^1$)$_2$, hydroxy, alkyloxy, or alkyl; and
X represents —O—, —N$R^1$—, or —S—;
wherein Ⓒ may be substituted with any of alkyl, halo, hydroxy, alkyloxy, —S$R^1$, cyano, —C(=O)$R^6$, —NO$_2$, or —N($R^1$)$_2$.

In certain embodiments, the present invention relates to any one of the aforementioned compounds, wherein Y represents

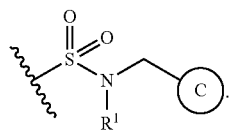

In certain embodiments, the present invention relates to any one of the aforementioned compounds, wherein Y represents

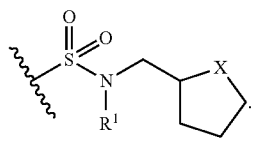

In certain embodiments, the present invention relates to any one of the aforementioned compounds, wherein Y represents

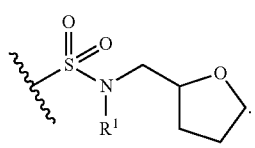

In certain embodiments, the present invention relates to any one of the aforementioned compounds, wherein Y represents

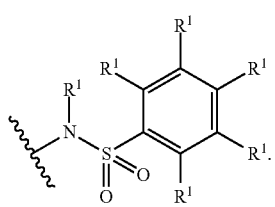

In certain embodiments, the present invention relates to any one of the aforementioned compounds, wherein Y represents

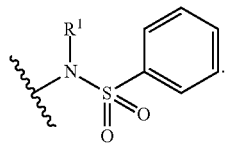

In certain embodiments, the present invention relates to any one of the aforementioned compounds, wherein Ⓐ represents a substituted 5-membered heteroaryl.

In certain embodiments, the present invention relates to any one of the aforementioned compounds, wherein Ⓐ represents

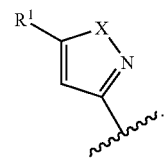

In certain embodiments, the present invention relates to any one of the aforementioned compounds, wherein Ⓐ represents

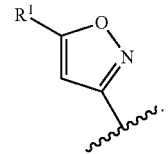

In certain embodiments, the present invention relates to any one of the aforementioned compounds, wherein Ⓐ represents an unsubstituted 5-membered heteroaryl. In certain embodiments, the present invention relates to any one of the aforementioned compounds, wherein Ⓐ represents

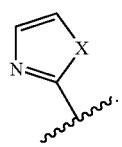

In certain embodiments, the present invention relates to any one of the aforementioned compounds, wherein Ⓐ represents

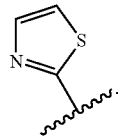

In certain embodiments, the present invention relates to any one of the aforementioned compounds, wherein X represents —N$R^1$—. In certain embodiments, the present invention relates to any one of the aforementioned compounds, wherein X represents —NH—. In certain embodiments, the present invention relates to any one of the aforementioned compounds, wherein X represents —N(CH₃)—.

In certain embodiments, the present invention relates to any one of the aforementioned compounds, wherein R¹ is alkyl. In certain embodiments, the present invention relates to any one of the aforementioned compounds, wherein R¹ is methyl, ethyl, n-propyl, or isopropyl. In certain embodiments, the present invention relates to any one of the aforementioned compounds, wherein R¹ is methyl.

In certain embodiments, the present invention relates to a compound of formula III

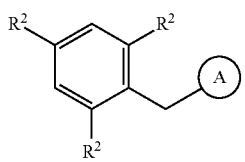

III or a pharmaceutically acceptable salt thereof,
wherein, independently for each occurrence,
Ⓐ represents a substituted or unsubstituted 5-membered heteroaryl;
R² is —H, alkyl, halo, or hydroxy;
R⁵ is cyano, —C(=O)R⁶; or —NO₂; and
R⁶ is —H, —N(R¹)₂, hydroxy, alkyloxy, or alkyl.

In certain embodiments, the present invention relates to any one of the aforementioned compounds, wherein Ⓐ represents a substituted 5-membered heteroaryl. In certain embodiments, the present invention relates to any one of the aforementioned compounds, wherein Ⓐ represents

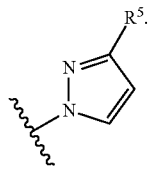

In certain embodiments, the present invention relates to any one of the aforementioned compounds, wherein Ⓐ represents

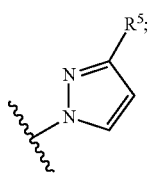

R⁵ is —C(=O)R⁶; and R⁶ is alkyloxy.

In certain embodiments, the present invention relates to any one of the aforementioned compounds, wherein R² is —H or halo. In certain embodiments, the present invention relates to any one of the aforementioned compounds, wherein at least one of R² is halo. In certain embodiments, the present invention relates to any one of the aforementioned compounds, wherein one of R² is halo and two of R² are —H. In certain embodiments, the present invention relates to any one of the aforementioned compounds, wherein R² is fluoro, chloro, bromo, or iodo. In certain embodiments, the present invention relates to any one of the aforementioned compounds, wherein R² is chloro.

In certain embodiments, the present invention relates to a compound of formula IV

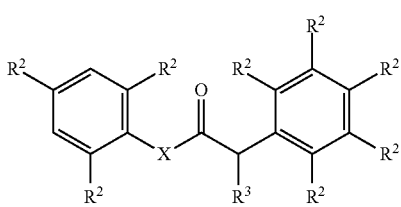

IV or a pharmaceutically acceptable salt thereof,
wherein, independently for each occurrence,
R¹ is —H or alkyl;
R² is —H, alkyl, halo, or hydroxy;
R³ is —H, alkyloxy, hydroxy, or —SR¹; and
X represents —O—, —NR¹—, or —S—.

In certain embodiments, the present invention relates to any one of the aforementioned compounds, wherein R² is —H or halo. In certain embodiments, the present invention relates to any one of the aforementioned compounds, wherein at least one of R² is halo. In certain embodiments, the present invention relates to any one of the aforementioned compounds, wherein one of R² is halo. In certain embodiments, the present invention relates to any one of the aforementioned compounds, wherein at least two of R² are halo. In certain embodiments, the present invention relates to any one of the aforementioned compounds, wherein two of R² are halo. In certain embodiments, the present invention relates to any one of the aforementioned compounds, wherein R² is fluoro, chloro, bromo, or iodo. In certain embodiments, the present invention relates to any one of the aforementioned compounds, wherein R² is fluoro.

In certain embodiments, the present invention relates to any one of the aforementioned compounds, wherein R³ is —H, alkyloxy, or hydroxy. In certain embodiments, the present invention relates to any one of the aforementioned compounds, wherein R³ is alkyloxy. In certain embodiments, the present invention relates to any one of the aforementioned compounds, wherein R³ is methoxy.

In certain embodiments, the present invention relates to any one of the aforementioned compounds, wherein X represents —NR¹—. In certain embodiments, the present invention relates to any one of the aforementioned compounds, wherein X represents —NH—. In certain embodiments, the present invention relates to any one of the aforementioned compounds, wherein X represents —N(CH₃)—.

In certain embodiments, the present invention relates to a compound of formula V

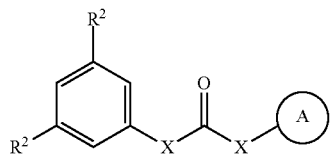

V or a pharmaceutically acceptable salt thereof, wherein, independently for each occurrence, Ⓐ represents a substituted or unsubstituted 5-membered heteroaryl;

$R^1$ is —H or alkyl;

$R^2$ is —H, alkyl, halo, or hydroxy; and

X represents —O—, —$NR^1$—, or —S—.

In certain embodiments, the present invention relates to any one of the aforementioned compounds, wherein Ⓐ represents a substituted 5-membered heteroaryl. In certain embodiments, the present invention relates to any one of the aforementioned compounds, wherein Ⓐ represents

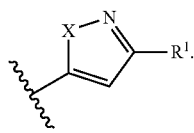

In certain embodiments, the present invention relates to any one of the aforementioned compounds, wherein Ⓐ represents

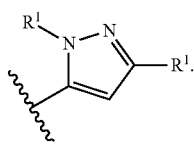

In certain embodiments, the present invention relates to any one of the aforementioned compounds, wherein Ⓐ represents

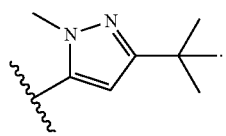

In certain embodiments, the present invention relates to any one of the aforementioned compounds, wherein $R^2$ is —H or halo. In certain embodiments, the present invention relates to any one of the aforementioned compounds, wherein at least one of $R^2$ is halo. In certain embodiments, the present invention relates to any one of the aforementioned compounds, wherein one of $R^2$ is halo. In certain embodiments, the present invention relates to any one of the aforementioned compounds, wherein two of $R^2$ are halo. In certain embodiments, the present invention relates to any one of the aforementioned compounds, wherein $R^2$ is fluoro, chloro, bromo, or iodo. In certain embodiments, the present invention relates to any one of the aforementioned compounds, wherein $R^2$ is chloro.

In certain embodiments, the present invention relates to any one of the aforementioned compounds, wherein X represents —$NR^1$—. In certain embodiments, the present invention relates to any one of the aforementioned compounds, wherein X represents —NH—. In certain embodiments, the present invention relates to any one of the aforementioned compounds, wherein X represents —$N(CH_3)$—.

In certain embodiments, the present invention relates to a compound of formula VI

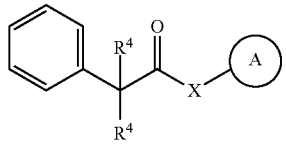

or a pharmaceutically acceptable salt thereof, wherein, independently for each occurrence, Ⓐ represents a substituted or unsubstituted 5-membered heteroaryl;

$R^1$ is —H or alkyl;

$R^4$ is —H or alkyl, or any two instances of $R^4$, taken together, form a ring; and X represents —O—, —$NR^1$—, or —S—.

In certain embodiments, the present invention relates to any one of the aforementioned compounds, wherein Ⓐ represents a substituted 5-membered heteroaryl. In certain embodiments, the present invention relates to any one of the aforementioned compounds, wherein Ⓐ represents

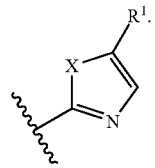

In certain embodiments, the present invention relates to any one of the aforementioned compounds, wherein Ⓐ represents

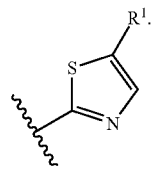

In certain embodiments, the present invention relates to any one of the aforementioned compounds, wherein Ⓐ represents

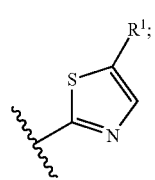

and $R^1$ is methyl, ethyl, n-propyl, or iso-propyl. In certain embodiments, the present invention relates to any one of the aforementioned compounds, wherein Ⓐ represents

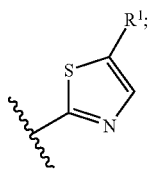

and $R^1$ is methyl.

In certain embodiments, the present invention relates to any one of the aforementioned compounds, wherein X represents —$NR^1$—. In certain embodiments, the present invention relates to any one of the aforementioned compounds, wherein X represents —NH—. In certain embodiments, the present invention relates to any one of the aforementioned compounds, wherein X represents —N(CH$_3$)—.

In certain embodiments, the present invention relates to any one of the aforementioned compounds, wherein $R^4$ is alkyl. In certain embodiments, the present invention relates to any one of the aforementioned compounds, wherein the two instances of $R^4$, taken together, form a ring. In certain embodiments, the present invention relates to any one of the aforementioned compounds, wherein the two instances of $R^4$, taken together, form a cyclopropyl ring.

In certain embodiments, the present invention relates to a compound of formula VII

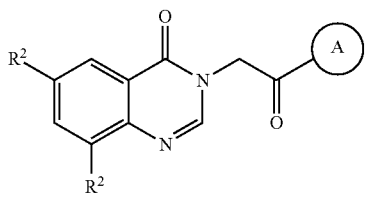

VII or a pharmaceutically acceptable salt thereof,
wherein, independently for each occurrence,
Ⓐ represents a substituted or unsubstituted 5-membered heteroaryl;
$R^1$ is —H or alkyl;
$R^2$ is —H, alkyl, halo, or hydroxy; and
X represents —O—, —$NR^1$—, or —S—.

In certain embodiments, the present invention relates to any one of the aforementioned compounds, wherein Ⓐ represents an unsubstituted 5-membered heteroaryl. In certain embodiments, the present invention relates to any one of the aforementioned compounds, wherein Ⓐ represents

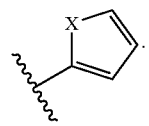

In certain embodiments, the present invention relates to any one of the aforementioned compounds, wherein Ⓐ represent

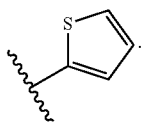

In certain embodiments, the present invention relates to any one of the aforementioned compounds, wherein $R^2$ is —H or halo. In certain embodiments, the present invention relates to any one of the aforementioned compounds, wherein at least one of $R^2$ is halo. In certain embodiments, the present invention relates to any one of the aforementioned compounds, wherein one of $R^2$ is halo. In certain embodiments, the present invention relates to any one of the aforementioned compounds, wherein $R^2$ is fluoro, chloro, bromo, or iodo. In certain embodiments, the present invention relates to any one of the aforementioned compounds, wherein $R^2$ is bromo.

In certain embodiments, the present invention relates to a compound of formula VIII

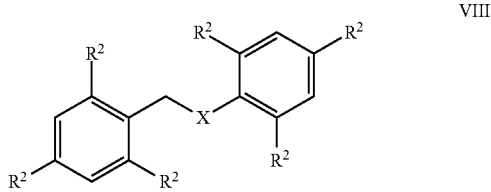

VIII or a pharmaceutically acceptable salt thereof,
wherein, independently for each occurrence,
$R^1$ is —H or alkyl;
$R^2$ is —H, alkyl, halo, or hydroxy; and
X represents —O—, —$NR^1$—, or —S—.

In certain embodiments, the present invention relates to any one of the aforementioned compounds, wherein X represents —$NR^1$—. In certain embodiments, the present invention relates to any one of the aforementioned compounds, wherein X represents —NH—. In certain embodiments, the present invention relates to any one of the aforementioned compounds, wherein X represents —N(CH$_3$)—.

In certain embodiments, the present invention relates to any one of the aforementioned compounds, wherein $R^2$ is —H or halo. In certain embodiments, the present invention relates to any one of the aforementioned compounds, wherein at least one of $R^2$ is halo. In certain embodiments, the present invention relates to any one of the aforementioned compounds, wherein one of $R^2$ is halo. In certain embodiments, the present invention relates to any one of the aforementioned compounds, wherein at least two of $R^2$ are halo. In certain embodiments, the present invention relates to any one of the aforementioned compounds, wherein two of $R^2$ are halo. In certain embodiments, the present invention relates to any one of the aforementioned compounds, wherein $R^2$ is fluoro, chloro, bromo, or iodo. In certain embodiments, the present invention relates to any one of the aforementioned compounds, wherein one instance of $R^2$ is chloro; one instance of $R^2$ is fluoro; and four instances of $R^2$ are —H.

In certain embodiments, the present invention relates to a compound of formula IX

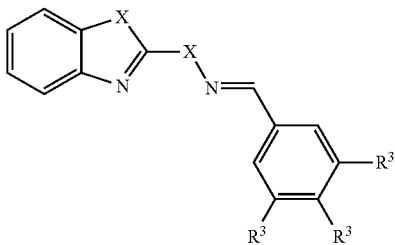

IX or a pharmaceutically acceptable salt thereof,
wherein, independently for each occurrence,
  $R^1$ is —H or alkyl;
  $R^3$ is —H, alkyloxy, hydroxy, or —$SR^1$; and
  X represents —O—, —$NR^1$—, or —S—.

In certain embodiments, the present invention relates to any one of the aforementioned compounds, wherein X represents —$NR^1$—. In certain embodiments, the present invention relates to any one of the aforementioned compounds, wherein X represents —NH—. In certain embodiments, the present invention relates to any one of the aforementioned compounds, wherein X represents —N(CH$_3$)—.

In certain embodiments, the present invention relates to any one of the aforementioned compounds, wherein $R^3$ is —H, alkyloxy, or hydroxy. In certain embodiments, the present invention relates to any one of the aforementioned compounds, wherein at least one of $R^3$ is alkyloxy. In certain embodiments, the present invention relates to any one of the aforementioned compounds, wherein at least one of $R^3$ is hydroxy. In certain embodiments, the present invention relates to any one of the aforementioned compounds, wherein at least two of $R^3$ are alkyloxy. In certain embodiments, the present invention relates to any one of the aforementioned compounds, wherein two of $R^3$ are alkyloxy. In certain embodiments, the present invention relates to any one of the aforementioned compounds, wherein at least one of $R^3$ is methoxy, ethoxy, or propoxy. In certain embodiments, the present invention relates to any one of the aforementioned compounds, wherein one instance of $R^3$ is hydroxy; one instance of $R^3$ is alkyloxy; and one instance of $R^3$ is —H. In certain embodiments, the present invention relates to any one of the aforementioned compounds, wherein two of $R^3$ are alkyloxy; and one instance of $R^3$ is —H.

In certain embodiments, the present invention relates to a compound of formula X

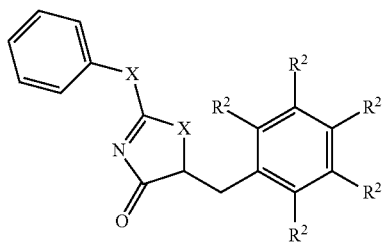

X or a pharmaceutically acceptable salt thereof,
wherein, independently for each occurrence,
  $R^1$ is —H or alkyl;
  $R^2$ is —H, alkyl, halo, or hydroxy; and
  X represents —O—, —$NR^1$—, or —S—.

In certain embodiments, the present invention relates to any one of the aforementioned compounds, wherein X represents —$NR^1$—. In certain embodiments, the present invention relates to any one of the aforementioned compounds, wherein X represents —NH—. In certain embodiments, the present invention relates to any one of the aforementioned compounds, wherein X represents —N(CH$_3$)—. In certain embodiments, the present invention relates to any one of the aforementioned compounds, wherein X represents —S—. In certain embodiments, the present invention relates to any one of the aforementioned compounds, wherein one instance of X is —$NR^1$— and one instance of X is —S—.

In certain embodiments, the present invention relates to any one of the aforementioned compounds, wherein $R^2$ is —H or halo. In certain embodiments, the present invention relates to any one of the aforementioned compounds, wherein at least one of $R^2$ is halo. In certain embodiments, the present invention relates to any one of the aforementioned compounds, wherein one of $R^2$ is halo. In certain embodiments, the present invention relates to any one of the aforementioned compounds, wherein at least two of $R^2$ are halo. In certain embodiments, the present invention relates to any one of the aforementioned compounds, wherein two of $R^2$ are halo. In certain embodiments, the present invention relates to any one of the aforementioned compounds, wherein $R^2$ is fluoro, chloro, bromo, or iodo. In certain embodiments, the present invention relates to any one of the aforementioned compounds, wherein two instances of $R^2$ are chloro; and one instance of $R^2$—H.

In certain embodiments, the present invention relates to a compound of formula XI

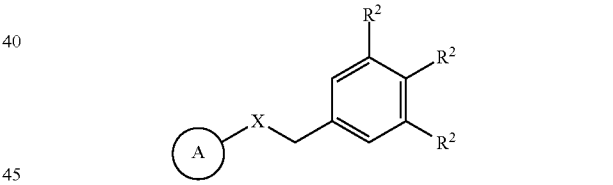

XI or a pharmaceutically acceptable salt thereof,
wherein, independently for each occurrence,
  Ⓐ represents a substituted or unsubstituted 5-membered heteroaryl;
  $R^1$ is —H or alkyl;
  $R^2$ is —H, alkyl, halo, or hydroxy; and
  X represents —O—, —$NR^1$—, or —S—.

In certain embodiments, the present invention relates to any one of the aforementioned compounds, wherein Ⓐ represents an unsubstituted 5-membered heteroaryl. In certain embodiments, the present invention relates to any one of the aforementioned compounds, wherein Ⓐ represents

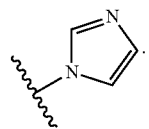

In certain embodiments, the present invention relates to any one of the aforementioned compounds, wherein X represents —O—.

In certain embodiments, the present invention relates to any one of the aforementioned compounds, wherein $R^2$ is —H or halo. In certain embodiments, the present invention relates to any one of the aforementioned compounds, wherein at least one of $R^2$ is halo. In certain embodiments, the present invention relates to any one of the aforementioned compounds, wherein one of $R^2$ is halo. In certain embodiments, the present invention relates to any one of the aforementioned compounds, wherein at least two of $R^2$ are halo. In certain embodiments, the present invention relates to any one of the aforementioned compounds, wherein two of $R^2$ are halo. In certain embodiments, the present invention relates to any one of the aforementioned compounds, wherein $R^2$ is fluoro, chloro, bromo, or iodo. In certain embodiments, the present invention relates to any one of the aforementioned compounds, wherein two instances of $R^2$ are chloro; and one instance of $R^2$—H.

In certain embodiments, the present invention relates to a compound of formula XII

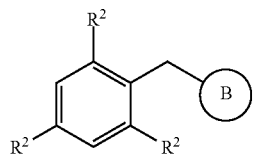

XII or a pharmaceutically acceptable salt thereof,
wherein, independently for each occurrence,
  Ⓑ represents a substituted 6-membered heteroaryl;
  $R^1$ is —H or alkyl;
  $R^2$ is —H, alkyl, halo, or hydroxy; and
  $R^6$ is —H, —N$(R^1)_2$, hydroxy, alkyloxy, or alkyl;
  wherein Ⓑ is substituted with any of alkyl, halo, hydroxy, alkyloxy, —SR$^1$, cyano, —C(=O)R$^6$, —NO$_2$, or —N$(R^1)_2$.

In certain embodiments, the present invention relates to any one of the aforementioned compounds, wherein Ⓑ represents

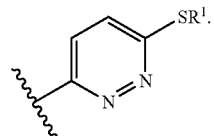

In certain embodiments, the present invention relates to any one of the aforementioned compounds, wherein $R^2$ is —H or halo. In certain embodiments, the present invention relates to any one of the aforementioned compounds, wherein at least one of $R^2$ is halo. In certain embodiments, the present invention relates to any one of the aforementioned compounds, wherein one of $R^2$ is halo. In certain embodiments, the present invention relates to any one of the aforementioned compounds, wherein at least two of $R^2$ are halo. In certain embodiments, the present invention relates to any one of the aforementioned compounds, wherein two of $R^2$ are halo. In certain embodiments, the present invention relates to any one of the aforementioned compounds, wherein $R^2$ is fluoro, chloro, bromo, or iodo. In certain embodiments, the present invention relates to any one of the aforementioned compounds, wherein two instances of $R^2$ are chloro; and one instance of $R^2$—H.

In certain embodiments, the present invention relates to a compound of formula XIII

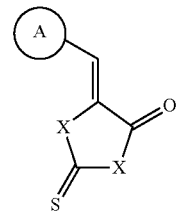

XIII or a pharmaceutically acceptable salt thereof,
wherein, independently for each occurrence,
  Ⓐ represents a substituted or unsubstituted 5-membered heteroaryl;
  $R^1$ is —H or alkyl; and
  X represents —O—, —NR$^1$—, or —S—.

In certain embodiments, the present invention relates to any one of the aforementioned compounds, wherein Ⓐ represents an unsubstituted 5-membered heteroaryl. In certain embodiments, the present invention relates to any one of the aforementioned compounds, wherein Ⓐ represents

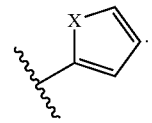

In certain embodiments, the present invention relates to any one of the aforementioned compounds, wherein Ⓐ represents

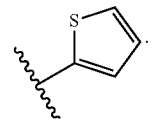

In certain embodiments, the present invention relates to any one of the aforementioned compounds, wherein Ⓐ represents a substituted 5-membered heteroaryl. In certain embodiments, the present invention relates to any one of the aforementioned compounds, wherein Ⓐ represents

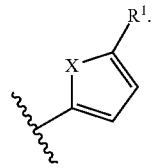

In certain embodiments, the present invention relates to any one of the aforementioned compounds, wherein Ⓐ represents

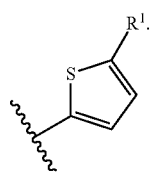

In certain embodiments, the present invention relates to any one of the aforementioned compounds, wherein (A) represents

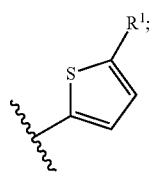

and R1 is methyl, ethyl, n-propyl, or iso-propyl.

In certain embodiments, the present invention relates to any one of the aforementioned compounds, wherein X represents —NR$^1$—. In certain embodiments, the present invention relates to any one of the aforementioned compounds, wherein one instance of X represents —NH—. In certain embodiments, the present invention relates to any one of the aforementioned compounds, wherein one instance of X represents —N(CH$_3$)—. In certain embodiments, the present invention relates to any one of the aforementioned compounds, wherein one instance of X represents —N(CH$_2$CH$_3$)—. In certain embodiments, the present invention relates to any one of the aforementioned compounds, wherein one instance of X represents —N(CH$_3$)—; and one instance of X represents —N(CH$_2$CH$_3$)—. In certain embodiments, the present invention relates to any one of the aforementioned compounds, wherein one instance of X represents —NH—; and one instance of X represents —N(CH$_2$CH$_3$)—.

In certain embodiments, the present invention relates to a compound of formula XIV

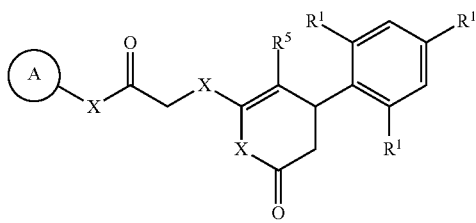

or a pharmaceutically acceptable salt thereof,
wherein, independently for each occurrence,
(A) represents a substituted or unsubstituted 5-membered heteroaryl;
R$^1$ is —H or alkyl;
R$^5$ is cyano, —C(=O)R$^6$; or —NO$_2$;
R$^6$ is —H, —N(R$^1$)$_2$, hydroxy, alkyloxy, or alkyl; and
X represents —O—, —NR$^1$—, or —S—.

In certain embodiments, the present invention relates to any one of the aforementioned compounds, wherein (A) represents an unsubstituted 5-membered heteroaryl. In certain embodiments, the present invention relates to any one of the aforementioned compounds, wherein (A) represents

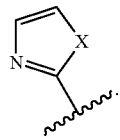

In certain embodiments, the present invention relates to any one of the aforementioned compounds, wherein (A) represents

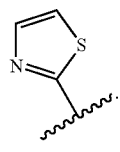

In certain embodiments, the present invention relates to any one of the aforementioned compounds, wherein one instance of R$^1$ is alkyl. In certain embodiments, the present invention relates to any one of the aforementioned compounds, wherein one instance of R$^1$ is methyl, ethyl, n-propyl, or isopropyl. In certain embodiments, the present invention relates to any one of the aforementioned compounds, wherein one instance of R$^1$ is methyl.

In certain embodiments, the present invention relates to any one of the aforementioned compounds, wherein R$^5$ is cyano.

In certain embodiments, the present invention relates to any one of the aforementioned compounds, wherein X represents —NR$^1$—. In certain embodiments, the present invention relates to any one of the aforementioned compounds, wherein one instance of X represents —NH—. In certain embodiments, the present invention relates to any one of the aforementioned compounds, wherein two instances of X represent —NH—. In certain embodiments, the present invention relates to any one of the aforementioned compounds, wherein one instance of X represents —S—. In certain embodiments, the present invention relates to any one of the aforementioned compounds, wherein one instance of X represents —S—; and two instances of X represent —NH—.

In certain embodiments, the present invention relates to a compound, or a pharmaceutically acceptable salt thereof, selected from the group consisting of:

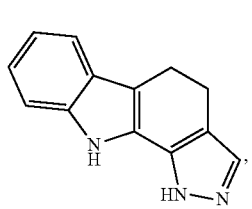, 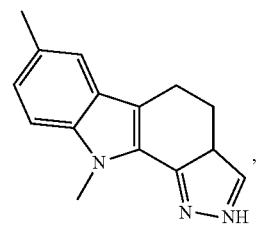,

43
-continued
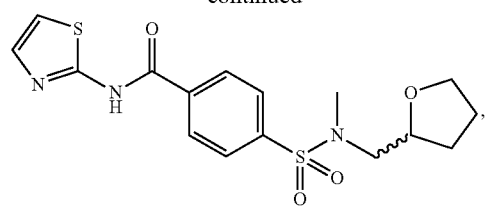
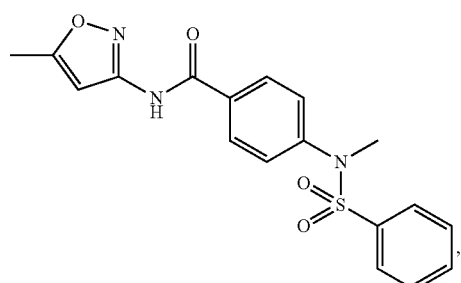
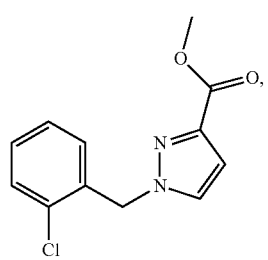
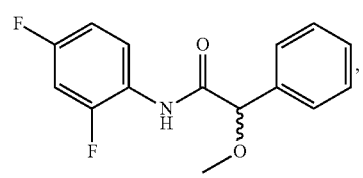
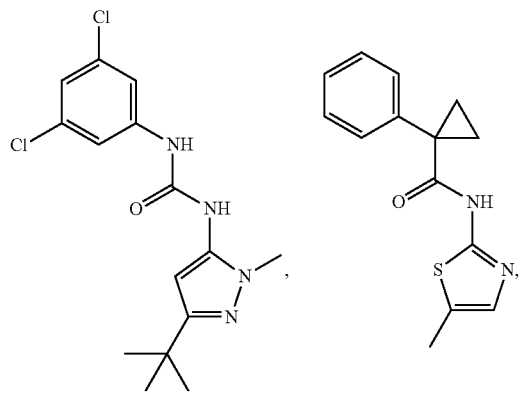
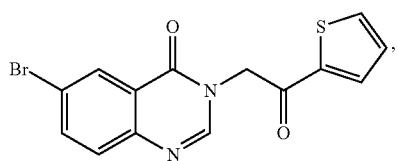
44
-continued
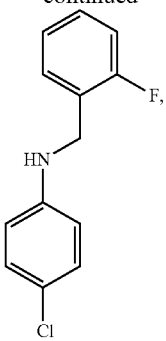
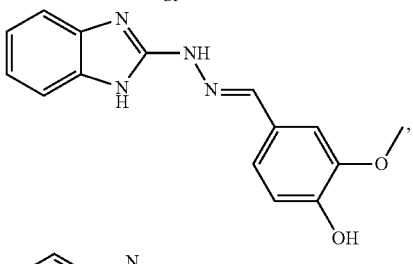
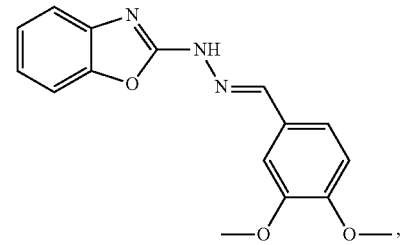
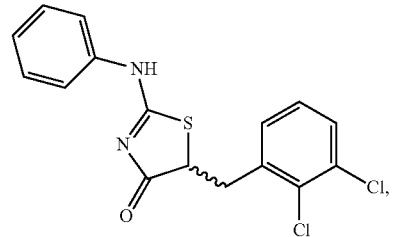
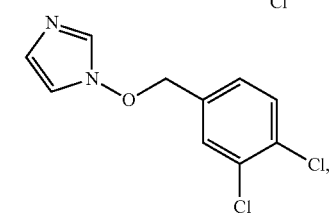
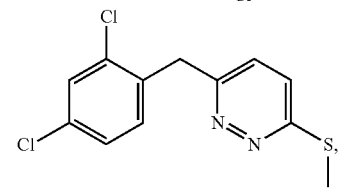
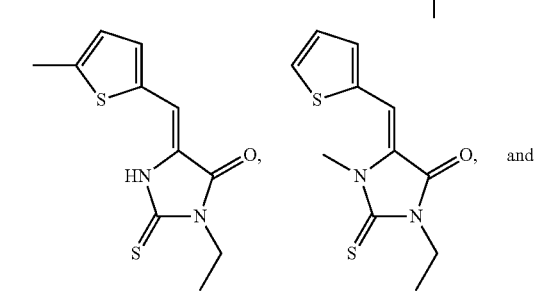
and

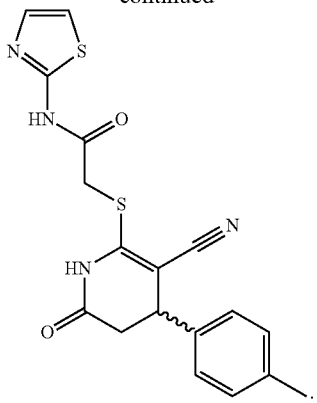

Many of the compounds of the invention may be provided as salts with pharmaceutically compatible counterions (i.e., pharmaceutically acceptable salts). A "pharmaceutically acceptable salt" means any non-toxic salt that, upon administration to a recipient, is capable of providing, either directly or indirectly, a compound or a prodrug of a compound of this invention. A "pharmaceutically acceptable counterion" is an ionic portion of a salt that is not toxic when released from the salt upon administration to a recipient. Pharmaceutically compatible salts may be formed with many acids, including but not limited to hydrochloric, sulfuric, acetic, lactic, tartaric, malic, succinic, etc. Salts tend to be more soluble in aqueous or other protonic solvents than are the corresponding free base forms.

Acids commonly employed to form pharmaceutically acceptable salts include inorganic acids such as hydrogen bisulfide, hydrochloric, hydrobromic, hydroiodic, sulfuric and phosphoric acid, as well as organic acids such as para-toluenesulfonic, salicylic, tartaric, bitartaric, ascorbic, maleic, besylic, fumaric, gluconic, glucuronic, formic, glutamic, methanesulfonic, ethanesulfonic, benzenesulfonic, lactic, oxalic, para-bromophenylsulfonic, carbonic, succinic, citric, benzoic and acetic acid, and related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylenesulfonate, phenylacetate, phenylpropionate, phenylbutyrate, citrate, lactate, .beta.-hydroxybutyrate, glycolate, maleate, tartrate, methanesulfonate, propanesulfonate, naphthalene-1-sulfonate, naphthalene-2-sulfonate, mandelate and the like salts. Pharmaceutically acceptable acid addition salts include those formed with mineral acids such as hydrochloric acid and hydrobromic acid, and those formed with organic acids such as maleic acid.

Suitable bases for forming pharmaceutically acceptable salts with acidic functional groups include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl-N-ethylamine; diethylamine; triethylamine; mono-, bis-, or tris-(2-hydroxy-lower alkyl amines), such as mono-, bis-, or tris-(2-hydroxyethyl)amine, 2-hydroxy-tert-butylamine, or tris-(hydroxymethyl)methylamine, N,N-di-lower alkyl-N-(hydroxy lower alkyl)-amines, such as N,N-dimethyl-N-(2-hydroxyethyl)amine, or tri-(2-hydroxyethyl)amine; N-methyl-D-glucamine; and amino acids such as arginine, lysine, and the like.

Certain compounds of the invention and their salts may exist in more than one crystal form and the present invention includes each crystal form and mixtures thereof.

Certain compounds of the invention and their salts may also exist in the form of solvates, for example hydrates, and the present invention includes each solvate and mixtures thereof.

Certain compounds of the invention may contain one or more chiral centers, and exist in different optically active forms. When compounds of the invention contain one chiral center, the compounds exist in two enantiomeric forms and the present invention includes both enantiomers and mixtures of enantiomers, such as racemic mixtures. The enantiomers may be resolved by methods known to those skilled in the art, for example by formation of diastereoisomeric salts which may be separated, for example, by crystallization; formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step may be used to liberate the desired enantiomeric form. Alternatively, specific enantiomers may be synthesized by asymmetric synthesis using optically active reagents, substrates, catalysts or solvents, or by converting one enantiomer into the other by asymmetric transformation.

When a compound of the invention contains more than one chiral center, it may exist in diastereoisomeric forms. The diastereoisomeric compounds may be separated by methods known to those skilled in the art, for example chromatography or crystallization and the individual enantiomers may be separated as described above. The present invention includes each diastereoisomer of compounds of the invention and mixtures thereof.

Certain compounds of the invention may exist in different tautomeric forms or as different geometric isomers, and the present invention includes each tautomer and/or geometric isomer of compounds of the invention and mixtures thereof.

Certain compounds of the invention may exist in different stable conformational forms which may be separable. Torsional asymmetry due to restricted rotation about an asymmetric single bond, for example because of steric hindrance or ring strain, may permit separation of different conformers. The present invention includes each conformational isomer of compounds of the invention and mixtures thereof.

Certain compounds of the invention may exist in zwitterionic form and the present invention includes each zwitterionic form of compounds of the invention and mixtures thereof.

The present invention also includes pro-drugs. As used herein the term "pro-drug" refers to an agent which is converted into the parent drug in vivo by some physiological chemical process (e.g., a prodrug on being brought to the physiological pH is converted to the desired drug form).

Pro-drugs are often useful because, in some situations, they may be easier to administer than the parent drug. They may, for instance, be bioavailable by oral administration whereas the parent drug is not. The prodrug may also have improved solubility in pharmacological compositions over the parent drug. An example, without limitation, of a pro-drug would be a compound of the present invention wherein it is administered as an ester (the "pro-drug") to facilitate transmittal across a cell membrane where water solubility is not beneficial, but then it is metabolically hydrolyzed to the carboxylic acid once inside the cell where water solubility is beneficial. Pro-drugs have many useful properties. For example, a pro-drug may be more water soluble than the ultimate drug, thereby facilitating intravenous administration of the drug. A pro-drug may also have a higher level of oral bioavailability than the ultimate drug. After administration, the prodrug is enzymatically or chemically cleaved to deliver the ultimate drug in the blood or tissue.

Exemplary pro-drugs upon cleavage release the corresponding free acid, and such hydrolyzable ester-forming residues of the compounds of this invention include but are not limited to carboxylic acid substituents (e.g., $—C(O)_2H$ or a moiety that contains a carboxylic acid) wherein the free hydrogen is replaced by $(C_1-C_4)$alkyl, $(C_2-C_{12})$alkanoyloxymethyl, $(C_4-C_9)$1-(alkanoyloxy)ethyl, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino) ethyl having from 4 to 10 carbon atoms, 3-phthalidyl, 4-crotonolactonyl, gamma-butyrolacton-4-yl, di-N,N—$(C_1$-$C_2)$alkylamino$(C_2-C_3)$alkyl (such as β-dimethylaminoethyl), carbamoyl-$(C_1-C_2)$alkyl, N,N-di$(C_1-C_2)$-alkylcarbamoyl-$(C_1-C_2)$alkyl and piperidino-, pyrrolidino- or morpholino$(C_2-C_3)$alkyl.

Other exemplary pro-drugs release an alcohol or amine of a compound of the invention wherein the free hydrogen of a hydroxyl or amine substituent is replaced by $(C_1-C_6)$ alkanoyloxymethyl, 1-(($C_1-C_6$)alkanoyloxy)ethyl, 1-methyl-1-(($C_1-C_6$)alkanoyloxy)ethyl, $(C_1-C_6)$alkoxycarbonyl-oxymethyl, N—$(C_1-C_6)$alkoxycarbonylaminomethyl, succinoyl, $(C_1-C_6)$alkanoyl, α-amino$(C_1-C_4)$alkanoyl, arylactyl and α-aminoacyl, or α-aminoacyl-α-aminoacyl wherein said α-aminoacyl moieties are independently any of the naturally occurring L-amino acids found in proteins, —P(O)(OH)$_2$, —P(O)(O($C_1-C_6$)alkyl)$_2$ or glycosyl (the radical resulting from detachment of the hydroxyl of the hemiacetal of a carbohydrate).

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P.G.M. *Protective Groups in Organic Synthesis*, 2nd ed.; Wiley: New York, 1991). Protected forms of the inventive compounds are included within the scope of this invention.

The term "chemically protected form," as used herein, pertains to a compound in which one or more reactive functional groups are protected from undesirable chemical reactions, that is, are in the form of a protected or protecting group (also known as a masked or masking group). It may be convenient or desirable to prepare, purify, and/or handle the active compound in a chemically protected form.

By protecting a reactive functional group, reactions involving other unprotected reactive functional groups can be performed, without affecting the protected group; the protecting group may be removed, usually in a subsequent step, without substantially affecting the remainder of the molecule. See, for example, Protective Groups in Organic Synthesis (T. Green and P. Wuts, Wiley, 1991), and Protective Groups in Organic Synthesis (T. Green and P. Wuts; 3rd Edition; John Wiley and Sons, 1999). For example, a hydroxy group may be protected as an ether (—OR) or an ester (—OC(=O)R), for example, as: a t-butyl ether; a benzyl, benzhydryl(diphenylmethyl), or trityl(triphenylmethyl)ether; a trimethylsilyl or t-butyldimethylsilyl ether; or an acetyl ester (—OC(=O)CH$_3$, —OAc).

For example, an aldehyde or ketone group may be protected as an acetal or ketal, respectively, in which the carbonyl group (C(=O)) is converted to a diether (C(OR)$_2$), by reaction with, for example, a primary alcohol. The aldehyde or ketone group is readily regenerated by hydrolysis using a large excess of water in the presence of acid.

For example, an amine group may be protected, for example, as an amide (—NRC(=O)R) or a urethane (—NRC(=O)OR), for example, as: a methyl amide (—NHC(=O)CH$_3$); a benzyloxy amide (—NHC(=O)OCH$_2$C$_6$H$_5$NHCbz); as a t-butoxy amide (—NHC(=O)OC (CH$_3$)$_3$, —NHBoc); a 2-biphenyl-2-propoxy amide (—NHC (=O)OC(CH$_3$)$_2$C$_6$H$_4$C$_6$H$_5$NHBoc), as a 9-fluorenylmethoxy amide (—NHFmoc), as a 6-nitroveratryloxy amide (—NHNvoc), as a 2-trimethylsilylethyloxy amide (—NHTeoc), as a 2,2,2-trichloroethyloxy amide (—NHTroc), as an allyloxy amide (—NHAlloc), as a 2-(phenylsulfonyl)ethyloxy amide (—NHPsec); or, in suitable cases (e.g., cyclic amines), as a nitroxide radical.

For example, a carboxylic acid group may be protected as an ester or an amide, for example, as: a benzyl ester; a t-butyl ester; a methyl ester; or a methyl amide.

For example, a thiol group may be protected as a thioether (—SR), for example, as: a benzyl thioether; or an acetamidomethyl ether (—SCH$_2$NHC(=O)CH$_3$).

Pharmaceutical Compositions

Described herein are pharmaceutical compositions that contain a necrostatin compound described herein. In some embodiments, the pharmaceutically compositions contain a therapeutically-effective amount of one or more of the necrostatins described above, formulated together with one or more pharmaceutically acceptable carriers. In another aspect, the necrostatins of the invention can be administered as such, or administered in mixtures with pharmaceutically acceptable carriers and can also be administered in conjunction with other anti-inflammatory agents. Conjunctive therapy thus includes sequential, simultaneous and separate, or co-administration of one or more compound of the invention, wherein the therapeutic effects of the first administered has not entirely disappeared when the subsequent compound is administered.

As described in detail below, in some embodiments, the pharmaceutical compositions may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; or (8) nasally.

As set out above, in certain embodiments, agents of the invention may be compounds containing a basic functional group, such as amino or alkylamino, and are, thus, capable of forming pharmaceutically-acceptable salts with pharmaceutically-acceptable acids. These salts can be prepared in situ in the administration vehicle or the dosage form manufacturing process, or through a separate reaction of a purified compound of the invention in its free base form with a suitable organic or inorganic acid, and isolating the salt thus formed during subsequent purification. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, and laurylsulphonate salts and the like (see, for example, Berge et al. (1977) "Pharmaceutical Salts", *J. Pharm. Sci.* 66:1-19).

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isothionic, and the like.

In other cases, the subject compounds may be compounds containing one or more acidic functional groups and, thus, are capable of forming pharmaceutically-acceptable salts with pharmaceutically-acceptable bases. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like (see, for example, Berge et al., supra).

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

The formulations of the necrostatins described herein may be presented in unit dosage form and may be prepared by any methods well known in the art of pharmacy. The amount of active ingredient which can be combined with a carrier material to produce a single dosage form will vary depending upon the host being treated and the particular mode of administration. The amount of active ingredient which can be combined with a carrier material to produce a single dosage form will generally be that amount of the agent which produces a therapeutic effect.

In certain embodiments, a formulation includes an excipient, including, but not limited to, cyclodextrins, liposomes, micelle forming agents, e.g., bile acids, and polymeric carriers, e.g., polyesters and polyanhydrides; and an agent of the present invention. In certain embodiments, an aforementioned formulation renders orally bioavailable a agent of the present invention.

Methods of preparing these formulations or compositions may include the step of bringing into association a necrostatin described herein with the carrier and, optionally, one or more accessory ingredients.

Liquid dosage forms for oral administration of the necrostatins described herein include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A composition described herein may also be administered as a bolus, electuary or paste. In solid dosage forms for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol, glycerol monostearate, and non-ionic surfactants; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. Compositions of the invention may also be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Dosage forms for the topical or transdermal administration of a necrostatin described herein include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Pharmaceutical compositions suitable for parenteral administration comprise one or more necrostatins in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

The preparations described herein may be given orally, parenterally, topically, or rectally. They are of course given in forms suitable for each administration route. For example, they are administered in tablets or capsule form, by injection, inhalation, eye lotion, ointment, suppository, administration by injection, infusion or inhalation; topical by lotion or ointment; and rectal by suppositories. Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Compounds or Compositions for Particular Uses

In certain embodiments, the invention relates to any one of the aforementioned compounds or compositions for use in the treatment of an inflammatory disease or other disease for inhibition of CD40 mediated TNFα production.

In certain embodiments, the invention relates to a compound selected from the group consisting of:

53
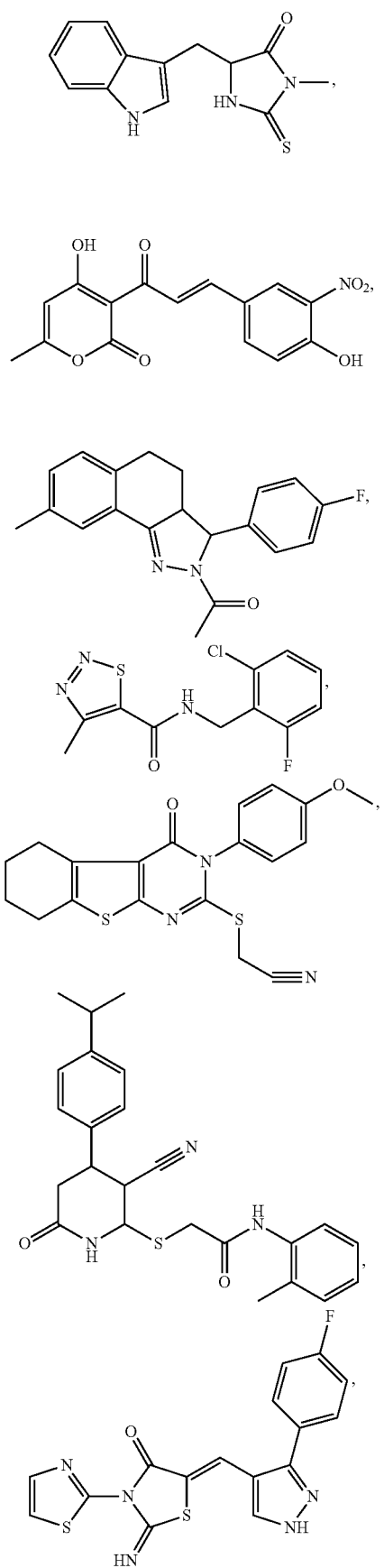
54
-continued
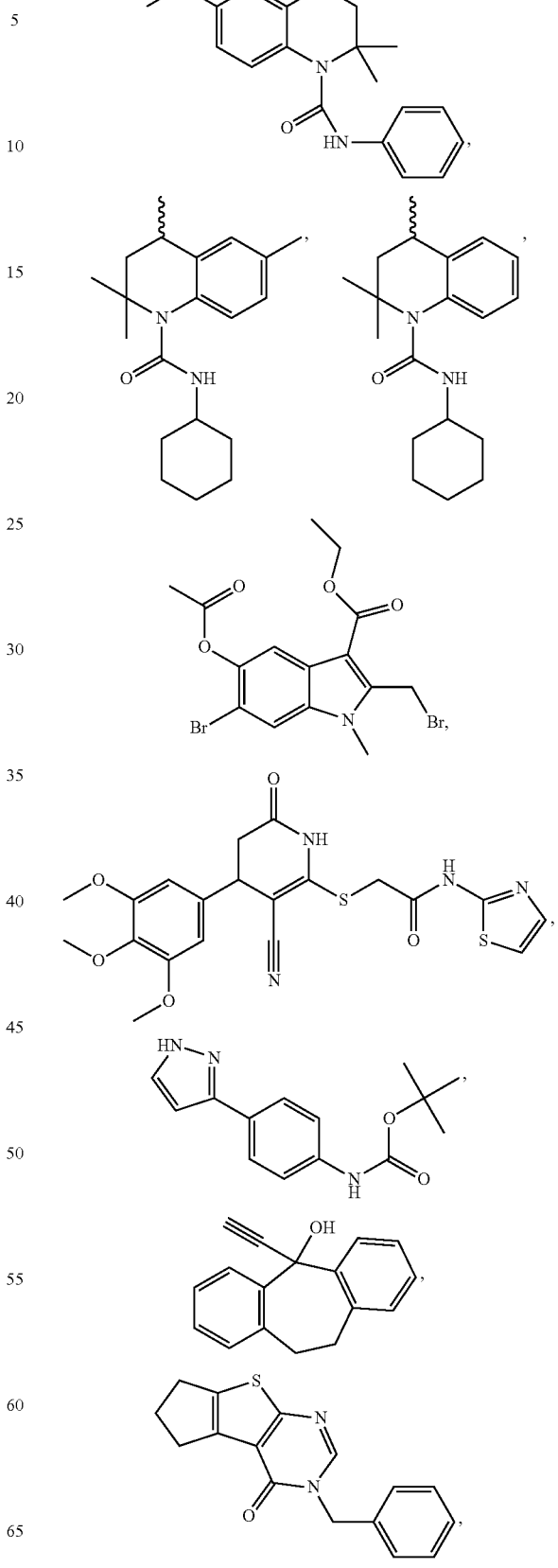

-continued

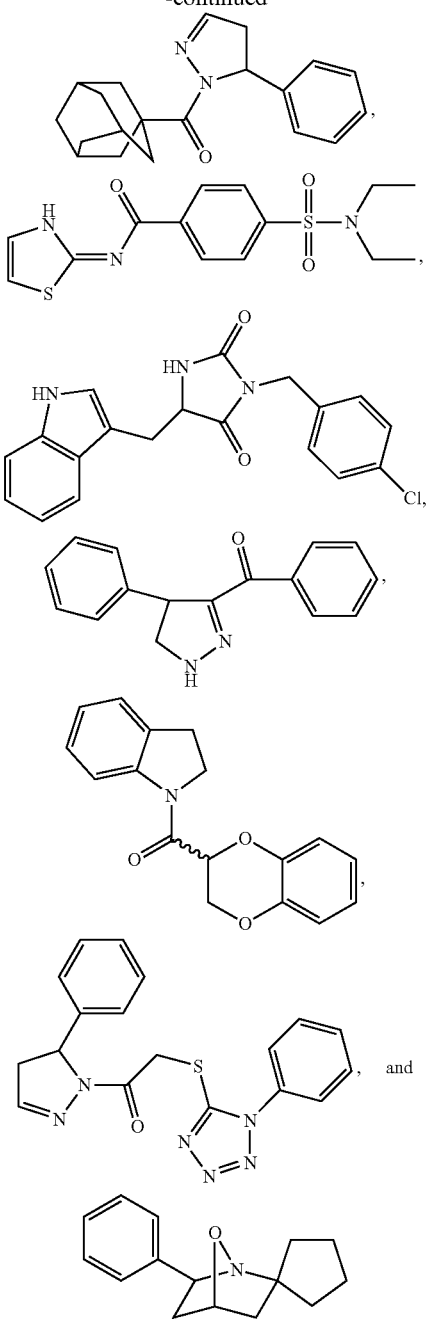

for use in the treatment of an inflammatory disease or other disease for inhibition of CD40 mediated TNFα production.

In ceratin embodiments, the invention relates to a compound selected from the group consisting of:

-continued

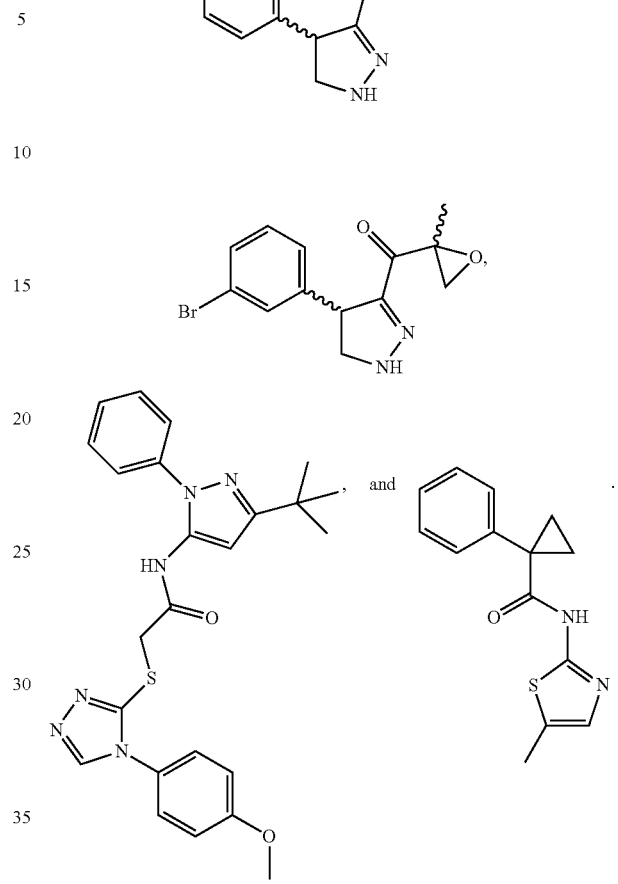

for use in the treatment of an inflammatory disease or other disease for inhibition of CD40 mediated TNFα production.

Pharmaceutical Methods

The present invention further provides novel therapeutic methods of treating inflammatory disease and other diseases for inhibition of CD40 mediated TNFα production, comprising administering to a subject, (e.g., a subject in need thereof), an effective amount of a compound of any one of formulas I-XIV.

The present invention further provides novel therapeutic methods of treating inflammatory disease and other diseases for inhibition of CD40 mediated TNFα production, comprising administering to a subject, (e.g., a subject in need thereof), an effective amount of a compound selected from the group consisting of

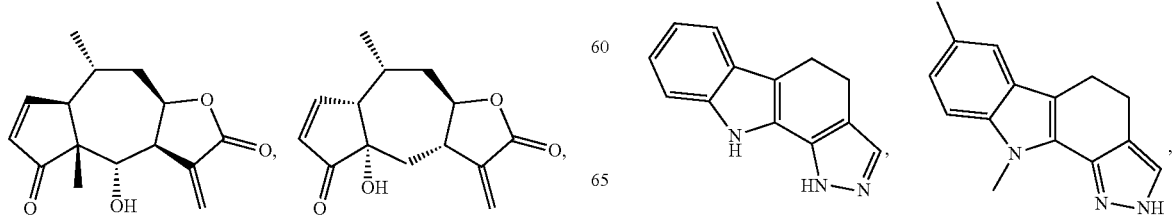

57
-continued
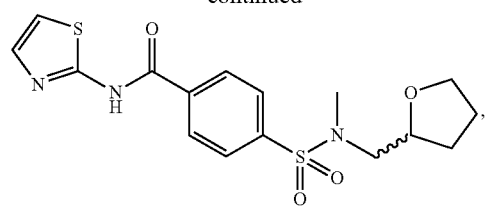
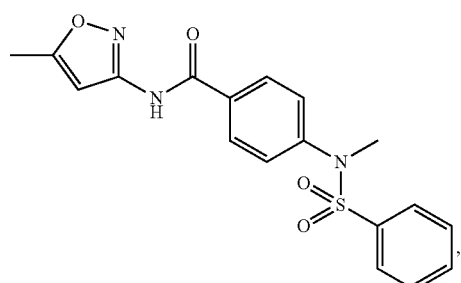
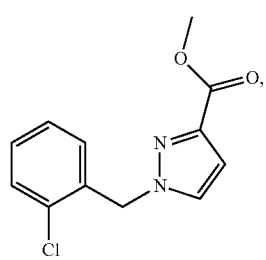
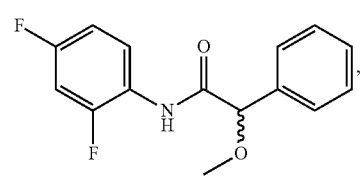
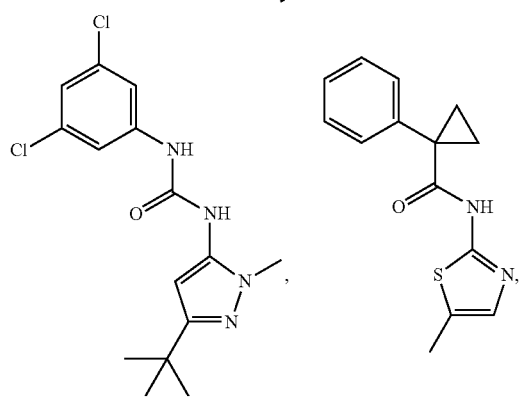
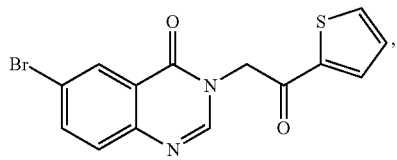
58
-continued
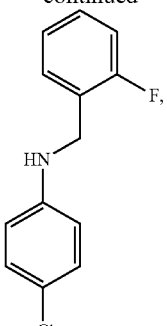
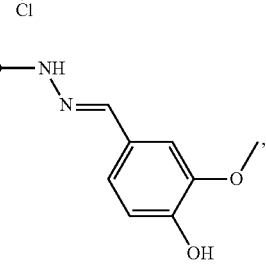
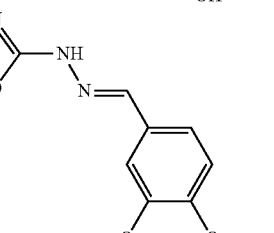
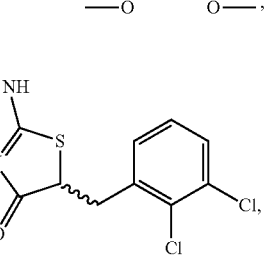
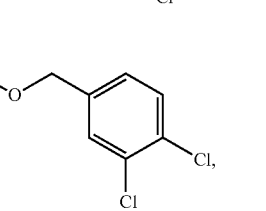
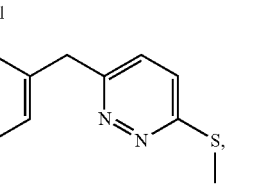
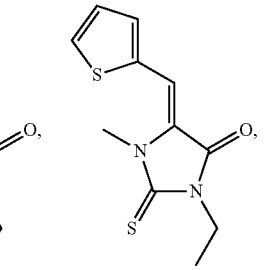 and -continued
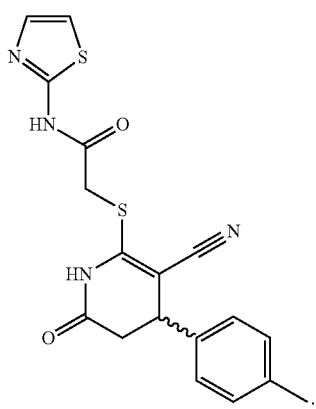
The present invention further provides novel therapeutic methods of treating inflammatory disease and other diseases for inhibition of CD40 mediated TNFα production, comprising administering to a subject, (e.g., a subject in need thereof), an effective amount of a compound selected from the group consisting of:
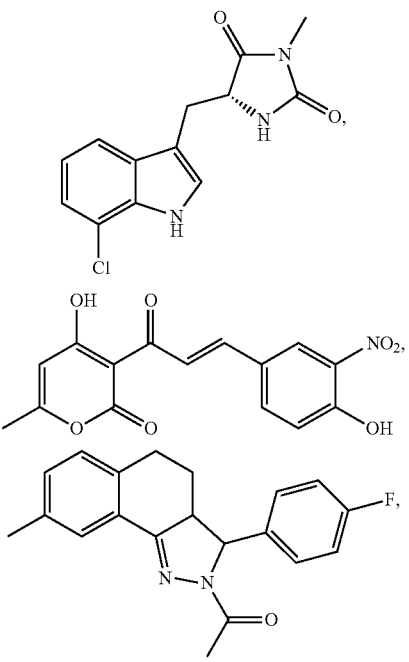
-continued
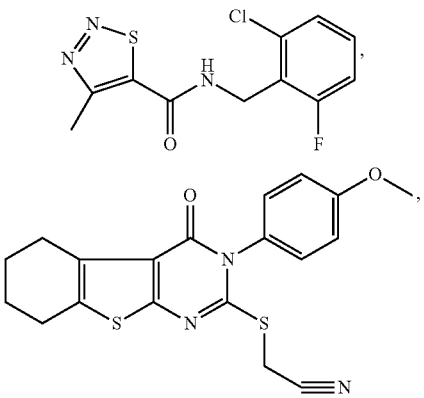
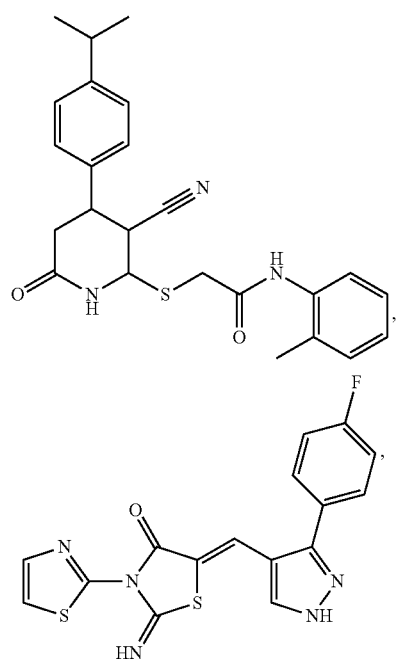

61
-continued
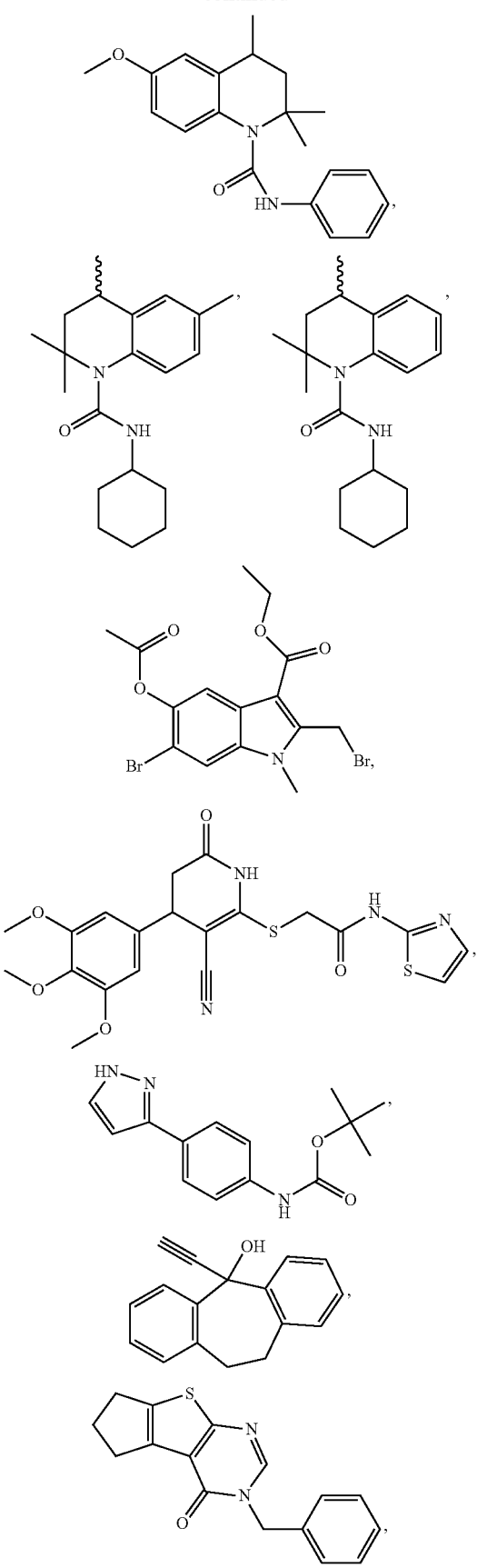
62
-continued
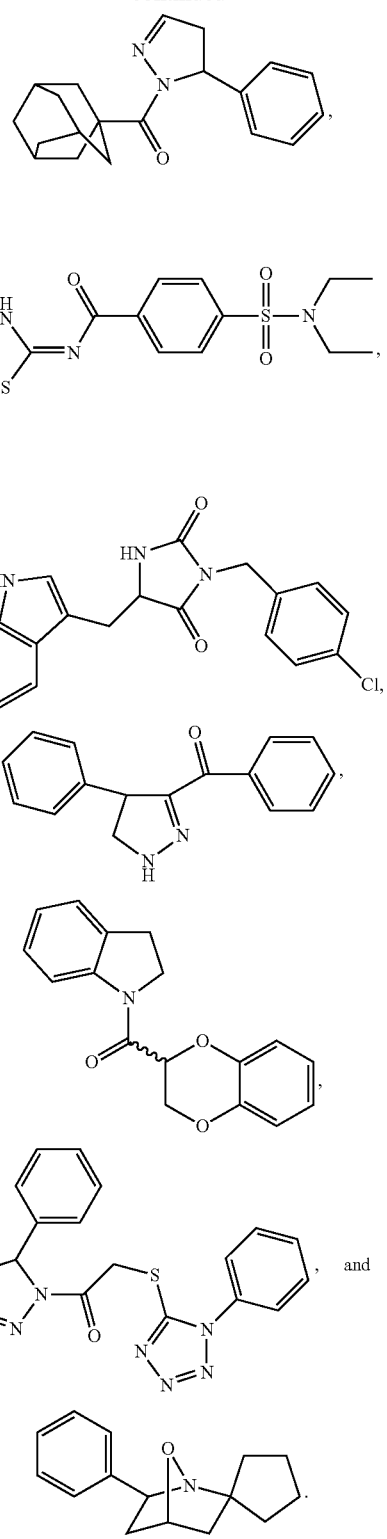
The present invention further provides novel therapeutic methods of treating inflammatory disease and other diseases for inhibition of CD40 mediated TNFα production, comprising administering to a subject, (e.g., a subject in need thereof), an effective amount of a compound selected from the group consisting of:

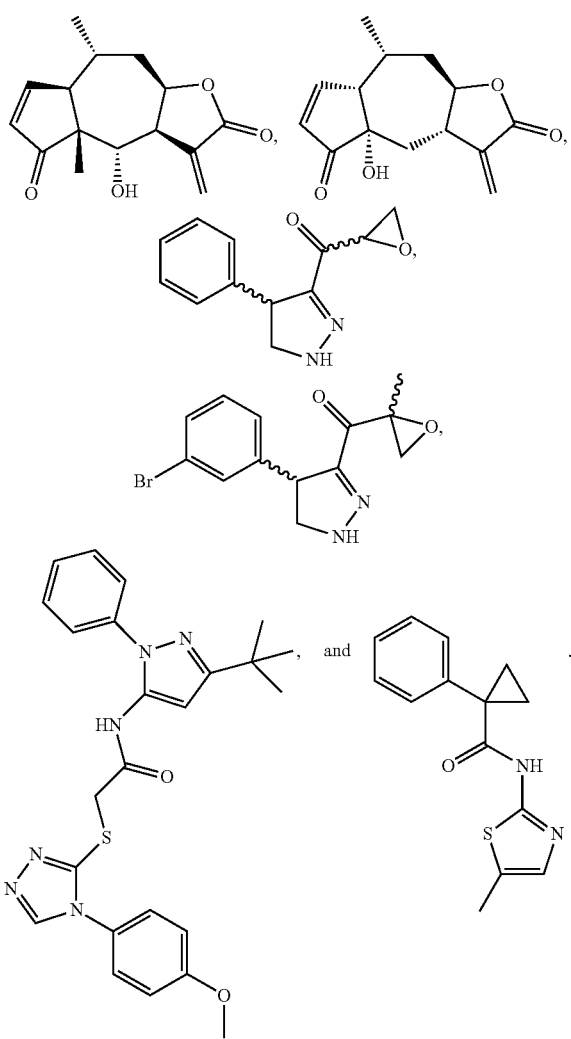

A subject in need thereof may include, for example, a subject who has been diagnosed with an inflammatory disease or a subject who is at high risk for an inflammatory disease.

The methods of the present invention may be used to treat any inflammatory disease. Examples of such inflammatory diseases include, but are not limited to, inflammatory bowel disease (e.g. Crohn's disease, ulcerative colitis), rheumatoid arthritis, psoriatic arthritis, psoriasis, diabetes mellitus, Alzheimer's disease, refractory asthma, multiple sclerosis, atherosclerosis, and vasculitis.

Inflammatory bowel diseases include, for example, certain art-recognized forms of a group of related conditions. Several major forms of inflammatory bowel diseases are known, with Crohn's disease (regional bowel disease, e.g., inactive and active forms) and ulcerative colitis (e.g., inactive and active forms) are the most common of these disorders. In addition, the IBD encompasses irritable bowel syndrome, microscopic colitis, lymphocytic-plasmocytic enteritis, coeliac disease, collagenous colitis, lymphocytic colitis and eosinophilic enterocolitis. Other less common forms of IBD include indeterminate colitis, infectious colitis (viral, bacterial or protozoan, e.g. amoebic colitis) (e.g., clostridium dificile colitis), pseudomembranous colitis (necrotizing colitis), ischemic inflammatory bowel disease, Behcet's disease, sarcoidosis, scleroderma, IBD-associated dysplasia, dysplasia associated masses or lesions, and primary sclerosing cholangitis.

In some embodiments, the methods of the present invention may be used to treat diseases or disorders related to a deleterious immune response, such as asthma, inflammatory disease, skin or organ transplantation, graft-versus-host disease (GVHD), or autoimmune diseases. Examples of autoimmune diseases include, for example, glomerular nephritis, arthritis, dilated cardiomyopathy-like disease, ulceous colitis, Sjogren syndrome, Crohn disease, systemic erythematodes, chronic rheumatoid arthritis, multiple sclerosis, psoriasis, allergic contact dermatitis, polymyosiis, pachyderma, periarteritis nodosa, rheumatic fever, vitiligo vulgaris, insulin dependent diabetes mellitus, Behcet disease, Hashimoto disease, Addison disease, dermatomyositis, myasthenia gravis, Reiter syndrome, Graves' disease, anaemia perniciosa, Goodpasture syndrome, sterility disease, chronic active hepatitis, pemphigus, autoimmune thrombopenic purpura, and autoimmune hemolytic anemia, active chronic hepatitis, Addison's disease, anti-phospholipid syndrome, atopic allergy, autoimmune atrophic gastritis, achlorhydra autoimmune, celiac disease, Cushing's syndrome, dermatomyositis, discoid lupus, erythematosis, Goodpasture's syndrome, Hashimoto's thyroiditis, idiopathic adrenal atrophy, idiopathic thrombocytopenia, insulin-dependent diabetes, Lambert-Eaton syndrome, lupoid hepatitis, some cases of lymphopenia, mixed connective tissue disease, pemphigoid, pemphigus vulgaris, pernicious anema, phacogenic uveitis, polyarteritis nodosa, polyglandular autosyndromes, primary biliary cirrhosis, primary sclerosing cholangitis, Raynaud's syndrome, relapsing polychondritis, Schmidt's syndrome, limited scleroderma (or crest syndrome), sympathetic ophthalmia, systemic lupus erythematosis, Takayasu's arteritis, temporal arteritis, thyrotoxicosis, type b insulin resistance, ulcerative colitis and Wegener's granulomatosis.

In some embodiments, the subject pharmaceutical compositions will incorporate a necrostatin described herein in an amount sufficient to deliver to a patient a therapeutically effective amount as part of a prophylactic or therapeutic treatment. The desired concentration of the necrostatin will depend on absorption, inactivation, and excretion rates of the drug as well as the delivery rate of the compound. It is to be noted that dosage values may also vary with the severity of the condition to be alleviated.

Actual dosage levels of the necrostatins in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular necrostatin employed, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could prescribe and/or administer doses of the agents of the invention employed in the pharmaceutical composition at levels lower than that required in order to achieve the desired therapeutic effect and gradually increase the dosage until the desired effect is achieved.

In general, a suitable daily dose of an agent of the invention will be that amount of the agent which is the lowest dose effective to produce a therapeutic effect. Such an effective dose will generally depend upon the factors described above.

One aspect of the invention relates to a method of inhibiting the TNFα expression by antigen presenting cells comprising contacting the antigen presenting cell with any of the aforementioned necrostatins, or a pharmaceutically acceptable salt, solvate, hydrate, prodrug, chemically-protected form, enantiomer or stereoisomer thereof.

Another aspect of the invention relates to a method of inhibiting inflammation in a subject comprising administering to the subject any of the aforementioned necrostatins, or a pharmaceutically acceptable salt, solvate, hydrate, prodrug, chemically-protected form, enantiomer or stereoisomer thereof.

Another aspect of the invention relates to a method of treating or preventing an inflammatory disease in a subject comprising administering to the subject any of the aforementioned necrostatins, or a pharmaceutically acceptable salt, solvate, hydrate, prodrug, chemically-protected form, enantiomer or stereoisomer thereof.

In certain embodiments, the present invention relates to any of the aforementioned methods, wherein the inflammatory disease is selected from the group consisting of inflammatory bowel disease (e.g. Crohn's disease, ulcerative colitis), rheumatoid arthritis, psoriatic arthritis, psoriasis, diabetes mellitus, Alzheimer's disease, refractory asthma and vasculitis.

In certain embodiments, the present invention relates to any of the aforementioned methods, wherein said subject is human.

EXEMPLIFICATION

The invention now being generally described, it will be more readily understood by reference to the following examples, which are included merely for purposes of illustration of certain aspects and embodiments of the present invention, and are not intended to limit the invention.

Example 1

RIP1 Kinase Mediates the Production of TNFα in Cells Stimulated by zVAD.fmk

The role of RIP1 kinase in the regulation of TNFα induction was investigated. zVAD.fmk is a caspase inhibitor that induces TNFα expression in various cell types. Murine macrophage J774 cells were treated with 20 μM zVAD.fmk and 10 μM of necrostatin and RIP1 inhibitor Nec-1 for the various periods of time. Cell lysates were extracted and analyzed by TNFα specific ELISA. As depicted in FIG. 1, treatment with zVAD.fmk induces an upregulation in TNFα protein levels as measured by ELISA in the cell lysate. Co-treatment with the RIP1 kinase inhibitor, Nec-1, almost completely inhibits the production of TNFα. An increase in TNFα is detectable in both the cell lysate (FIG. 1A) and cell supernatant (FIG. 1B), indicating that TNFα is synthesized and released from the cell in response to zVAD.fmk treatment.

Example 2

Figure 2:
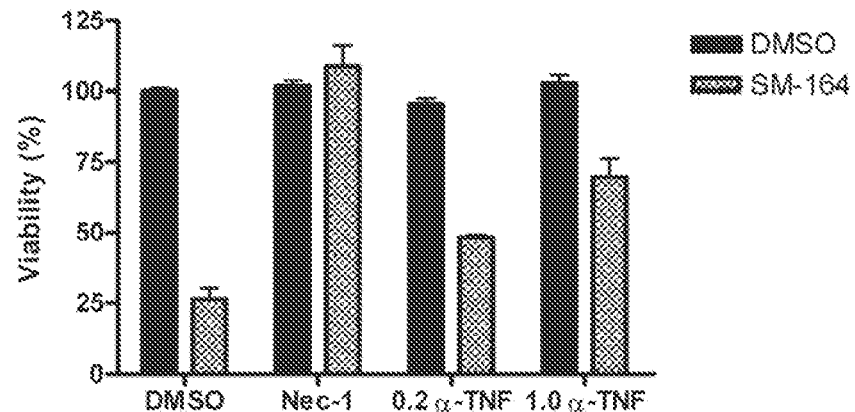
FIG. 2 shows the results of a cell viability assay (A) or a TNFα ELISA assay (B) performed using L929 cells treated with 100 nM SM-164 and 10 μM Nec-1, 0.2 μg/ml or 1.0n/ml anti-TNFα antibody.
Figure 2:
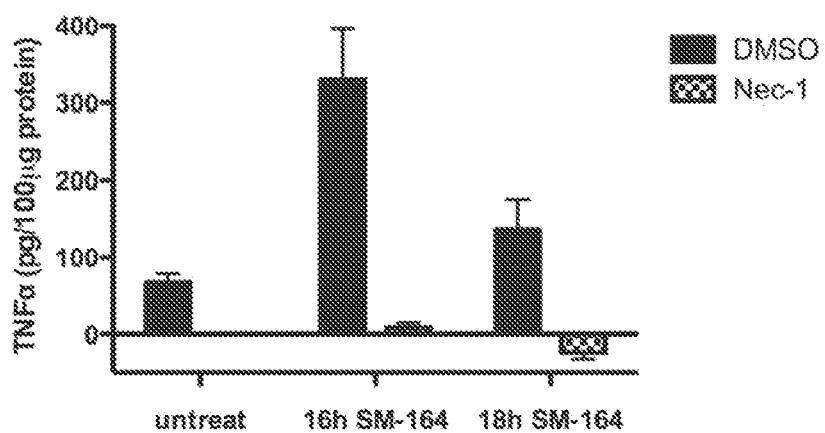

RIP1 Kinase Mediates the Production of TNFα in Cells Stimulated by IAP Antagonists Smac mimetic compounds are IAP antagonists that induce the production of TNFα. Smac mimetic compounds induce the autoubiquitination and degradation of cIAP1. L929 cells express TNFα and undergo cell death when treated with 100 nM of the Smac mimetic compound SM-164, as measured by an ATP assay. This cell death was inhibited by treatment with 10 μM Nec-1, or with 0.2 μg/ml or 1.0 μg/ml of TNFα neutralizing antibody (FIG. 2A). Furthermore, SM-164 treatment induced an increase in TNFα production by L929 cells, as measured by TNFα ELISA on cell lysates. As depicted in FIG. 2B, TNFα production was completely inhibited by Nec-1 co-treatment.

Figure 3:
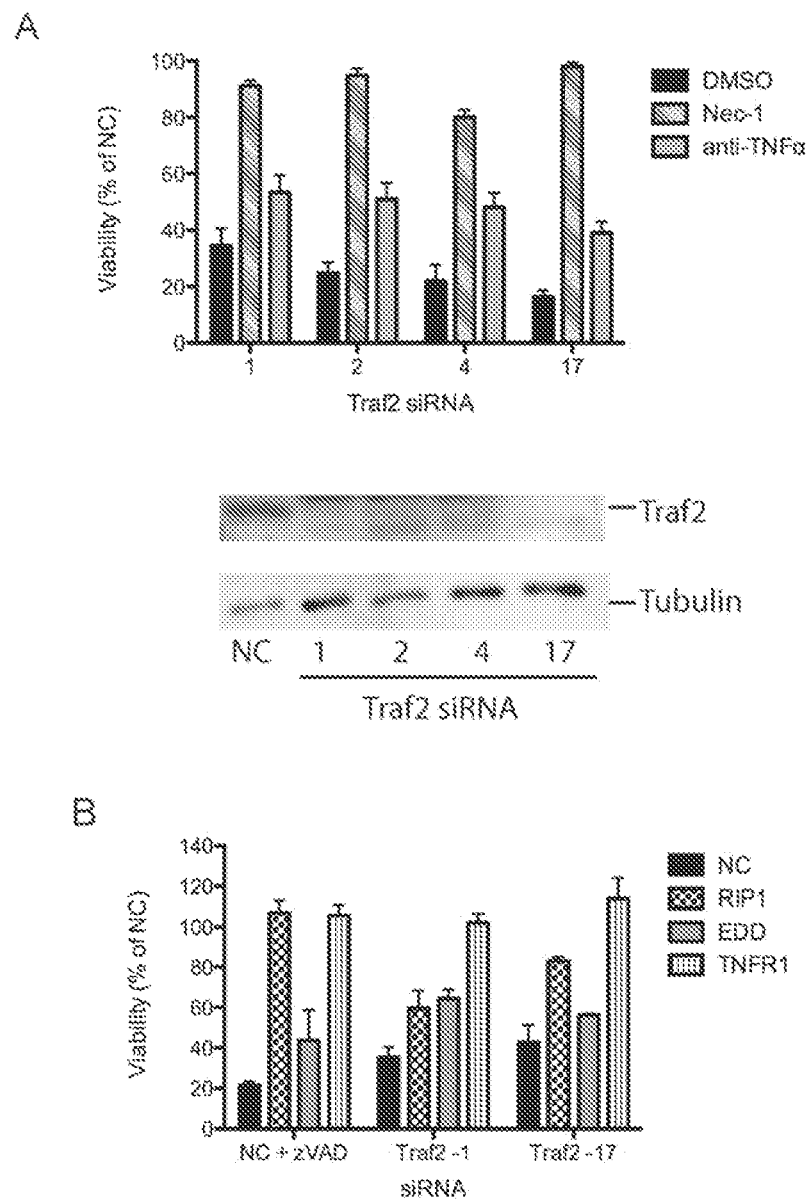
FIG. 3 shows the results of cell viability assays performed (A) using L929 cells transfected with the indicated amount of Traf2 siRNA and treated with 10 μM Nec-1 or 1.0 μg/ml anti-TNFα antibody for 48, or (B) using L929 cells transfected with the indicated siRNAs.
Figure 4:
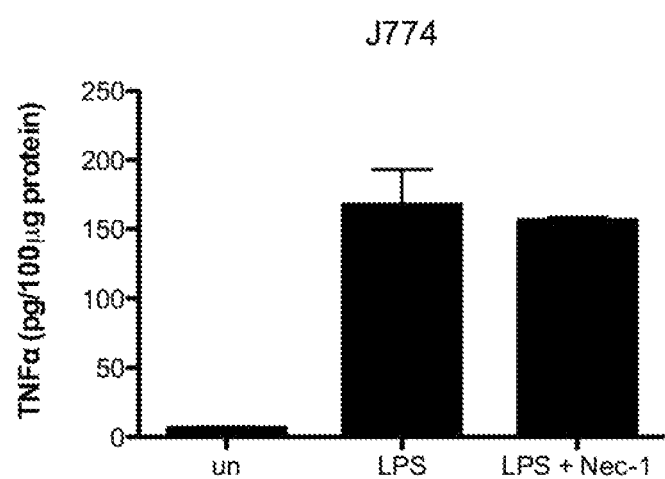
FIG. 4 shows the results of TNFα ELISA assays performed using J774 cells treated with 1 μg/ml LPS with or without 10 μM Nec-1 for 1 h.

In the TNFα signaling pathway, cIAP1, the target of Smac mimetic compounds, interacts closely with another protein, Traf2. L929 cells were transfected with Traf2 siRNA, treated with 10 μM Nec-1 or 1.0 μg/ml anti-TNFα antibody for 48 hours and cell viability measured by ATP assay. As depicted in FIG. 3A, knockdown of Traf2 using Traf2 specific siRNA cells induced cell death. This death was also dependent on TNFα production, as it was inhibited by treatment with a TNFα neutralizing antibody or with knockdown of TNFR1 (FIGS. 3A and 3B). Nec-1 was able to completely inhibit cell induced by the loss of Traf2, likely through the inhibition of TNFα production (FIG. 3A). A number of other stimuli have also induced TNFα production. One such treatment is lipopolysaccharide (LPS), a component of the bacterial outer membrane. Treatment of murine macrophage J774 cells with 1 1 μg/ml LPS resulted in a strong induction of TNFα in the cell lysate, as determined by ELISA. However, treatment of such cells with 10 μM Nec-1 has no effect on TNFα production in this case (FIG. 4). This data suggests that Nec-1 is not a general inhibitor of TNFα production.

Example 3

Necrostatin Compounds Inhibit Production of TNFα in Antigen Presenting Cells Stimulated by CD154

Macrophages are antigen presenting cells that are a major producer of TNFα under inflammatory conditions. Monocytes and macrophages are activated via cell contact with activated T cells. The interaction of CD40 on monocytes and macrophages with CD154
(CD40 ligand) on activated helper CD4$^+$ T cells is essential for T cell-mediated macrophage activation as marked by the production of TNFα and generation of nitric oxide. Thus, activated T cells have the potential to activate resting monocytes and macrophages via CD40 ligation in a contact-dependent, antigen-independent manner at sites of inflammation. The consequence of this interaction is the maintenance and augmentation of inflammatory process that includes the activation of macrophages, increased production of inflammatory cytokines and enhanced monocyte viability.

Figure 5:
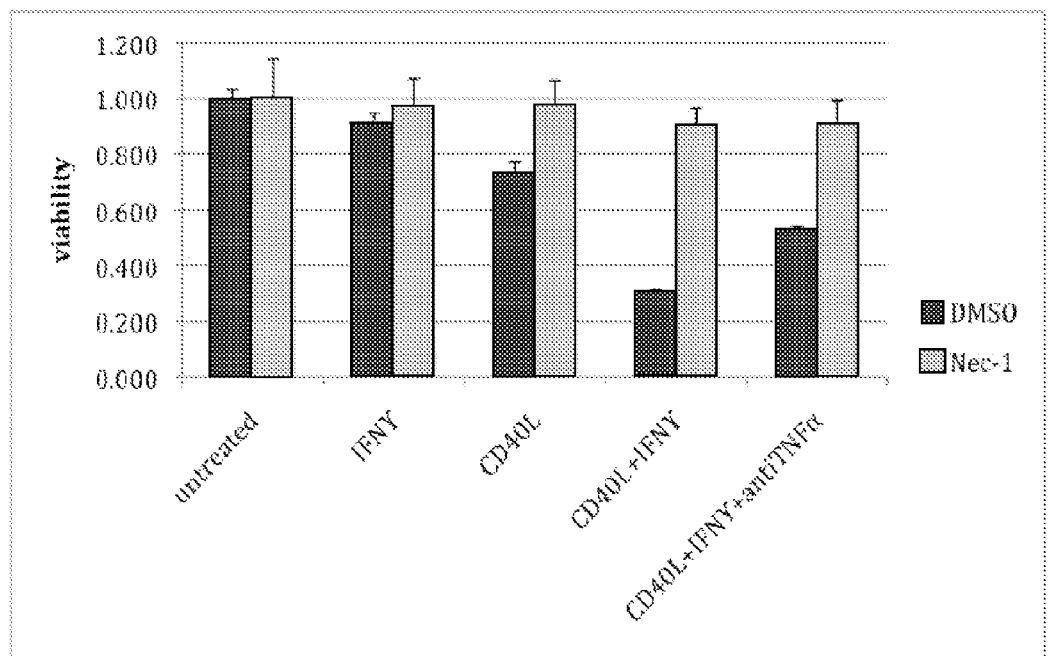
FIG. 5 shows the results of cell viability assays performed using L929 cells that were treated with CD154 (0.1 μg/ml), IFNγ (100 U/ml) and/or TNFα neutralizing antibody (1 μg/ml) alone or in combination with Nec-1 (10 μM) for 32 hrs.
Figure 6:
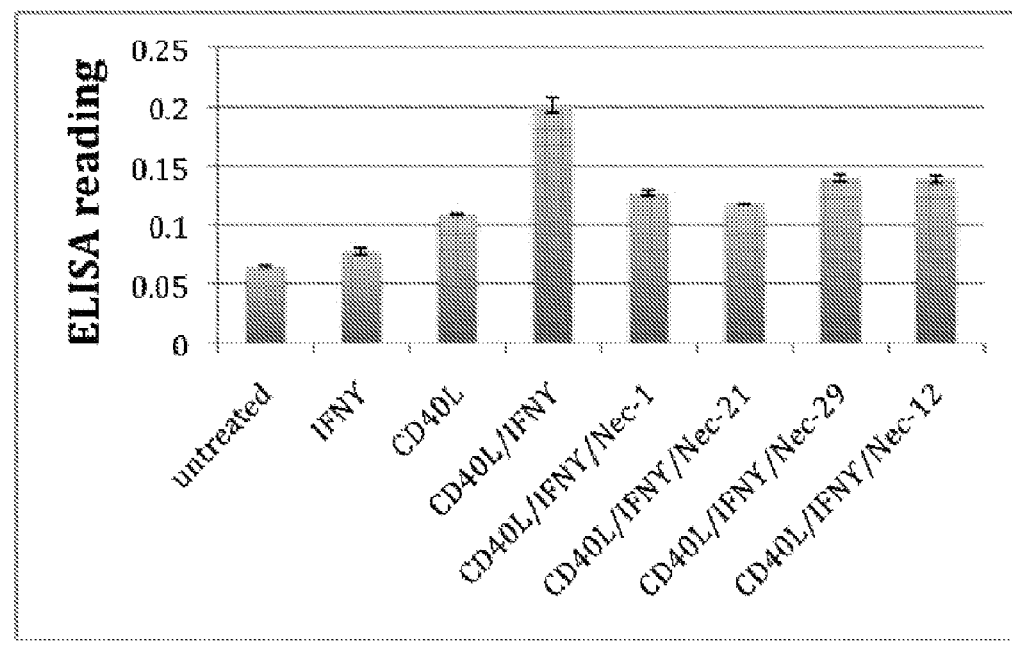
FIG. 6 shows the results of TNFα ELISA assays performed using spenic macrophages treated with 10 μM Nec-1, 10 μM Nec-21, 10 μM Nec-29, or 1 μM Nec-12 (11c), then treated with 1 μg/ml recombinant CD40 ligand and/or 100 U/ml IFNγ, as indicated.
Figure 7:
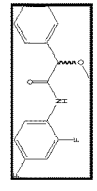
FIG. 7 depicts tabulated results from various assays of inventive compounds (Nec 21-34), including IC$_{50}$ and cell viability assays at 10 μM by ATP, performed using L929 cells treated with zVAD (20 μM), or Jurkat FADD-/- cells treated with TNFα (10 ng/mL), or MDA-MB-231 cells treated with SMAC mimetic SM-164 (100 nM), or NIH3T3 cells treated with TNFα (10 ng/mL)+CHX (1 μg/mL) overnight, as labelled.
Figure 7:
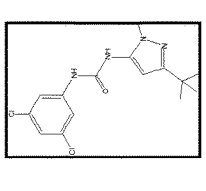
Figure 7:
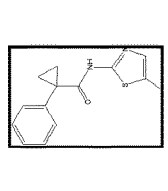
Figure 7:
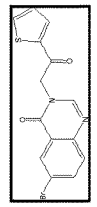
Figure 7:
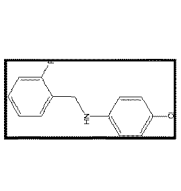
Figure 7:
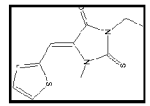
Figure 7:
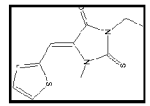
Figure 8:
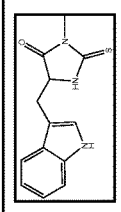
FIG. 8 depicts tabulated results from various assays of compounds (Nec 1-20, Helenalin, 3N, 3P, 14P, and 19P), including IC$_{50}$ and cell viability assays at 10 μM by ATP, performed using L929 cells treated with zVAD (20 μM), or Jurkat FADD-/- cells treated with TNFα (10 ng/mL), or MDA-MB-231 cells treated with SMAC mimetic SM-164 (100 nM), or NIH3T3 cells treated with TNFα (10 ng/mL)+ CHX (1 μg/mL) overnight, as labelled.
Figure 8:
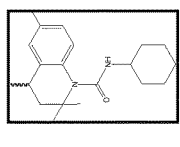
Figure 8:
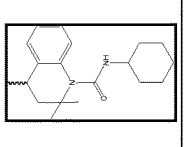
Figure 8:
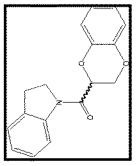
Figure 8:
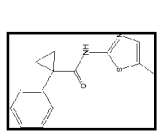
Figure 8:
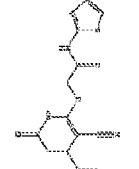
Figure 8:
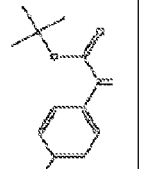
Figure 8:
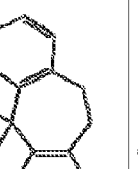
Figure 8:
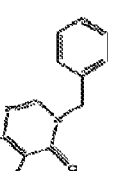
Figure 8:
Figure 8:
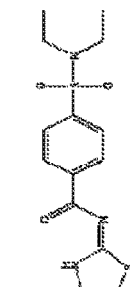
Figure 8:
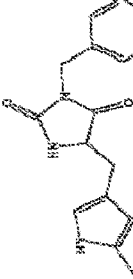
Figure 8:
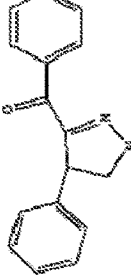
Figure 8:
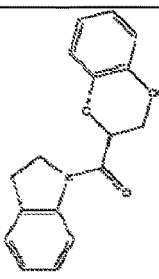
Figure 8:
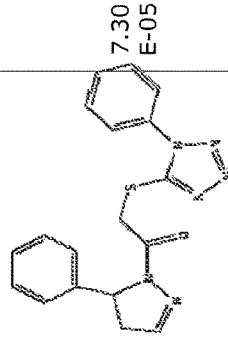
Figure 8:
Figure 9:
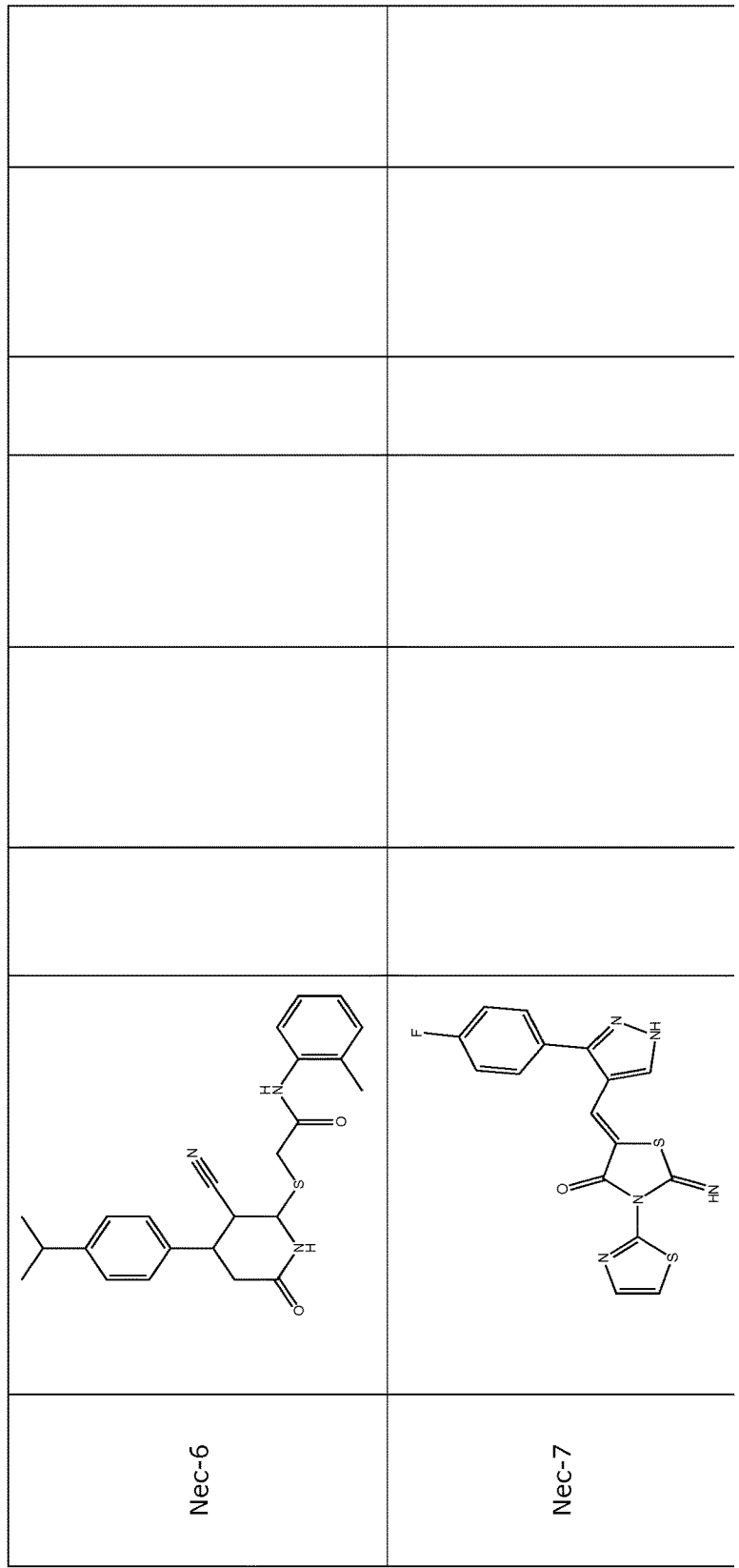
FIG. 9 depicts tabulated results from various assays of compounds (Nec 1-20), including $EC_{50}$ and $LD_{50}$ assays at 10 μM by ATP, performed using L929 cells, or Jurkat FADD−/− cells, as labelled.
Figure 9:
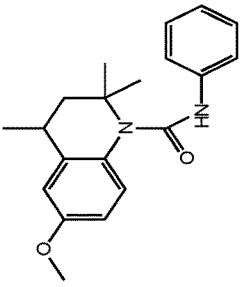
Figure 9:
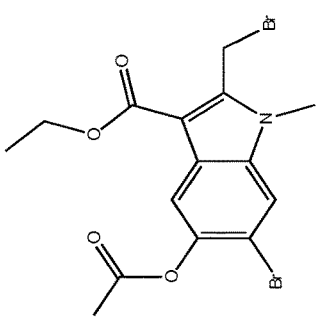
Figure 9:
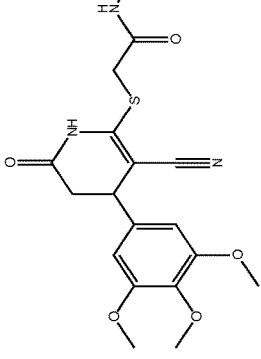
Figure 9:
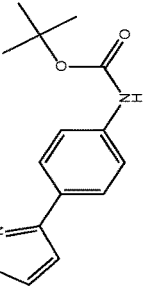
Figure 9:
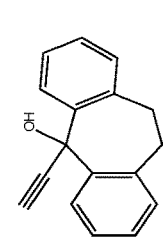
Figure 9:
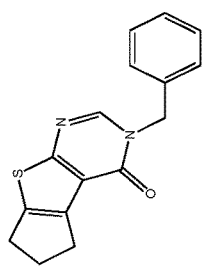
Figure 9:
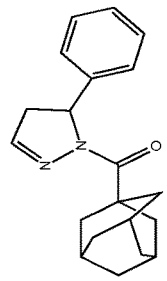
Figure 9:
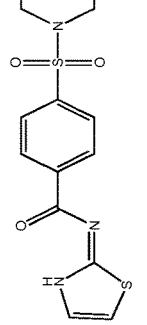
Figure 9:
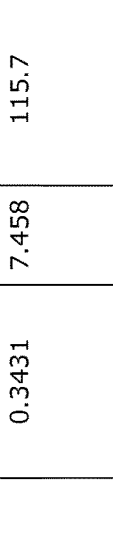
Figure 9:
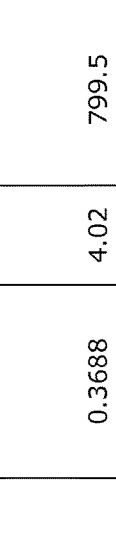
Figure 9:
Figure 9:
Figure 9:
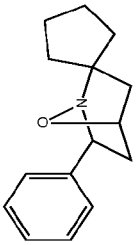

To test the involvement of CD40 in necroptosis, L929 cells were treated with CD154 (0.1 μg/ml), IFNγ (100 U/ml) and/or TNFα neutralizing antibody (1 μg/ml) alone or in combination and with or without Nec-1 (10 μM) for 32 hrs. Following treatment, cell survival was determined by Cell-Titer-Glo (Promega). As depicted in FIG. 5, the death of L929 cells induced by either the presence of either CD154 alone or by the presence of both CD154 and IFNγ was inhibited by Nec-1. Thus, RIP1 kinase selectively mediates intracellular signaling downstream of CD40 stimulation To further explore the role of RIP1 kinase in mediating CD40 signaling, the effect of necrostatins on the production of TNFα by primary macrophages stimulated by CD154 was tested. Splenocytes isolated from a C57BL/6 mouse were cultured for 10 days in RPMI media with 10% FBS and 50 µM 2-mercaptoethanol. The attached cells were harvested as splenic macrophages. The macrophages were pretreated for 1 hour with 10 µL1M Nec-1, 10 µM Nec-21, 10 µM Nec-29, or 1 µM Nec-12, then treated for 24 hours with 1 µg/ml recombinant CD154 (CD40L, R&D Systems) and/or 100 U/ml IFNγ as. TNFα secretion in the cell culture supernatant was analyzed by ELISA assay. As depicted in FIG. 6, the production of TNFα in splenic macrophages stimulated by CD154 in the presence of IFNγ was inhibited by Nec-1 as well as by the three other necrostatins tested, Nec-12, Nec-21 and Nec-29. These experiments indicate that RIP1 is involved in mediating TNFα production downstream of CD40 activation.

Example 4

The Role of RIP1 in Amyloid-β-Induced TNFα Production

Formation of plaques containing amyloid-β protein in the brain is closely associated with the onset and progression of Alzheimer's disease. Such amyloid-β plaques are believed to initiate a series of inflammatory events, including TNFα production by microglial cells, that contribute to disease progression.

Figure 10:
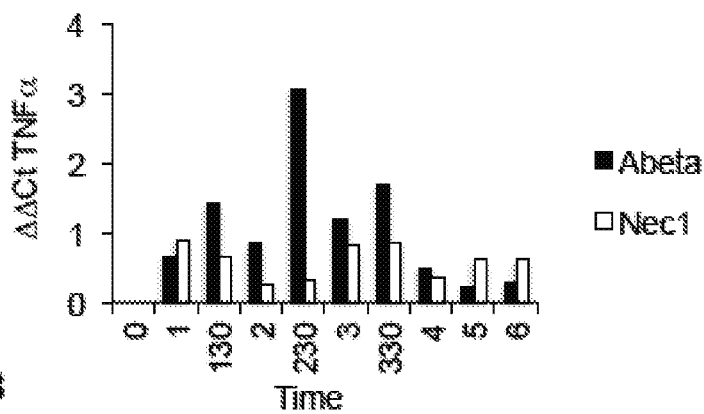
FIG. 10 shows Nec-1 blocks the production of TNFα mediated by amyloid-(3. A) BV2 cells were incubated for 30 minutes with 10 μM Nec-1 prior to being treated with Aβ42 (200 nM) for indicated times. The levels of TNFα mRNA were measured by quantitative PCR. B) Microglia primary cultures were incubated for 30 minutes with or without 10 μM Nec-1 prior to being treated with Aβ42 (200 nM). TNFα secretion was measured by ELISA. The data correspond to the mean±SD (N=3). C) Cell survival of microglia primary cultures treated with Aβ42 (200 nM) for indicated times with and without Nec1 was measured by CellTiter-Glo® assay. Error bars represent the mean of two different experiments.
Figure 10:
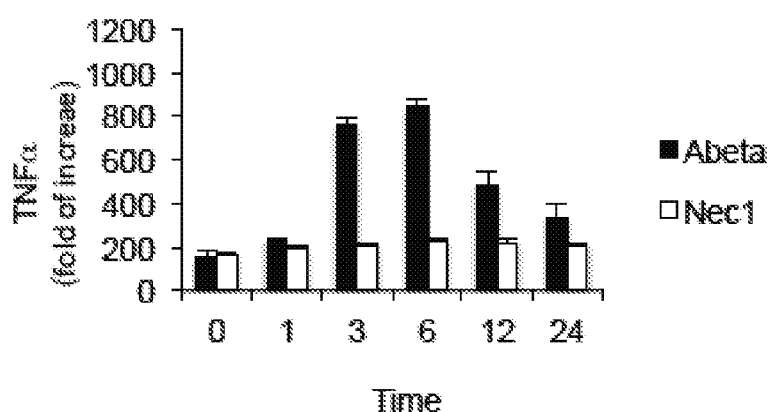
Figure 10:
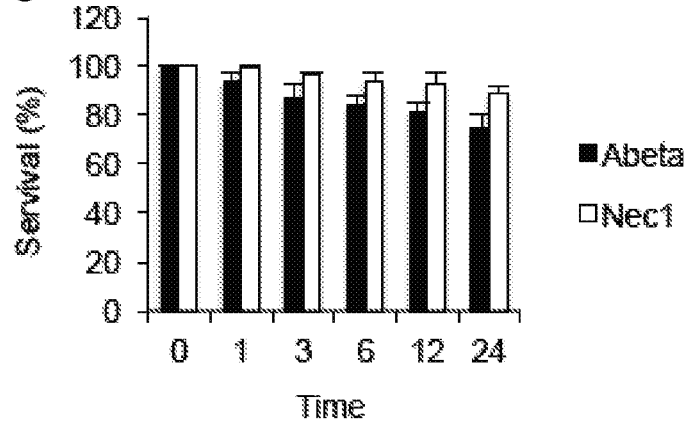

The role played by RIP1 in the induction of TNFα production by amyloid-β in microglial cells was investigated. As seen in FIGS. 10A and 10B, microglial cell line (BV2) or primary microglia cultures that were exposed to Aβ42 and treated with the RIP1 inhibitor Nec-1 produced reduced levels of TNFα compared to cells that were not treated with Nec-1. However, the treatment of Aβ only had a minor protective effect on the survival of microglia primary cells (FIG. 10C).

Figure 11:
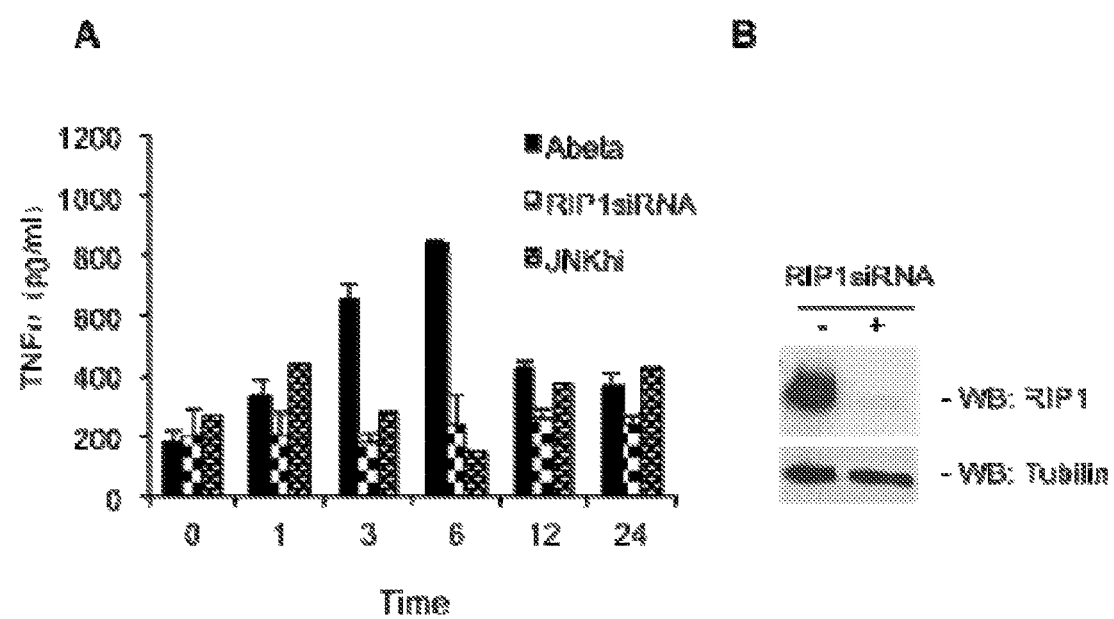
FIG. 11 shows inhibition of amyloid-β-induced TNFα secretion by RIP1 knockdown and JNK inhibition. BV2 cells were transfected with 20 nM RIP1 siRNA or incubated for 30 min with an JNK inhibitor (SP600125) 10 μM prior to being treated with Aβ42 (200 nM) for the indicated times. TNF-α secretion was measured by ELISA (A). The data correspond to the mean±SD (N=3). RIP1 knockdown was confirmed by western blotting (B). Protein lysates were analyzed by western blotting for RIP1 and α-Tubulin as a loading control.

Next, siRNA was used to inhibit RIP1 in BV2 cells that were exposed to Aβ42. As seen in FIG. 11, cells treated with RIP1 siRNA and Aβ42 produced less TNFα than cells treated with Aβ42 alone. The TNFα production inhibitory effect seen with the RIP1 siRNA treatment was similar to the inhibitory effect of treatment with JNK inhibitor SP600125. These results confirm the involvement of RIP1 in amyloid-β induced TNFα production by microglial cells.

Figure 12:
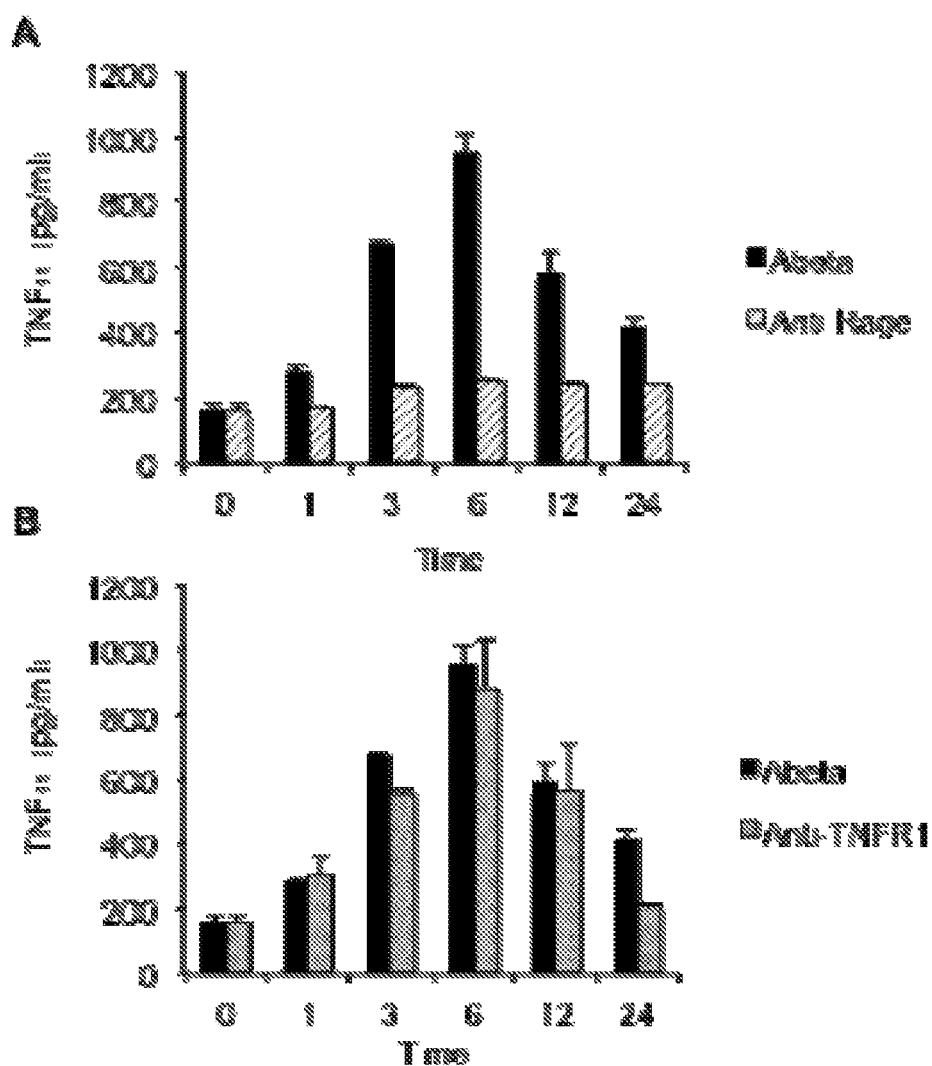
FIG. 12 shows amyloid-β-induced TNFα secretion is regulated by RAGE. BV2 cells were incubated for 30 minutes with 5μg/ml of A) anti-RAGE neutralizing antibody or B) anti-TNFR1 neutralizing antibody (as a control) prior to being treated with Aβ42 (200 nM) for the indicated times. TNFα secretion was measured by ELISA. The data correspond to the mean±SD (N=3).

To determine what receptors are involved in amyloid-β induced TNFα production, antibodies were used to block candidate receptors RAGE, TNFR1 and Fcγ in BV2 cells that were exposed to Aβ42. As seen in FIG. 12, blocking the RAGE receptor led to a reduction in TNFα production. Blocking the TNFR1 or the Fcγ receptor, on the other hand, had no effect on TNFα production (FIG. 12B and data not shown, respectively). These data indicate that the RAGE receptor plays a role in amyloid-β induced TNFα production by microglial cells.

Example 5

The role of RIP1 in CD40L induced TNFα Production

Figure 13:
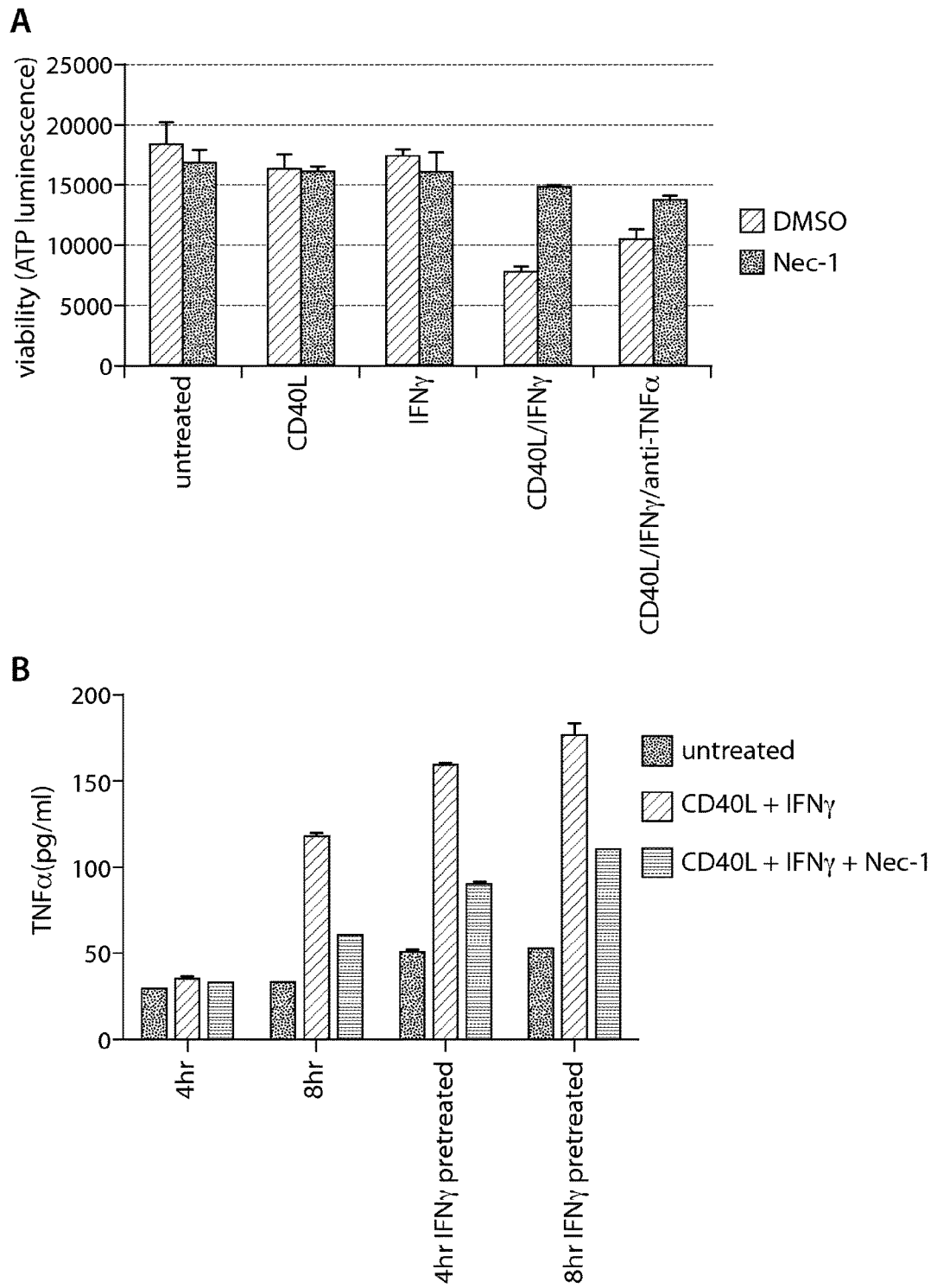
FIG. 13 shows that necrostatins block CD40L induced TNFα secretion. A, L929 cells were treated with 0.2 μg/ml CD40L, 100 U/ml IFNγ, and/or 1 μg/ml TNFα neutralizing antibody and then treated with 10 μM Nec-1 (right bar) or a DMSO control (left bar) for 24 hours. Viability was measure by ATP luminescence assay. B, BV-2 cells were pretreated with 100 U/ml IFNγ for 20 hours, and treated with 0.1 μg/ml CD40L for 4 or 8 hours. TNFα secretion was measured by ELISA.

The role of RIP1 in CD40L induced TNFα production was investigated. As seen in FIG. 13A, culturing L929 cells in both IFNγ and CD40L leads to a reduction in cell viability. Viability of cells cultured in IFNγ and CD40L is largely restored when the cells are also treated with either Nec-1 or anti-TNFα antibody. Treatment of cells with both Nec-1 and anti-TNFα results in a minimal viability improvement compared to cells treated with TNFα alone. These results indicate that Nec-1 increases the survival of CD40L treated cells by inhibiting the TNFα pathway.

To confirm the role of RIP1 in CD40L-induced TNFα production, BV-2 cells were pretreated with IFNγ and CD40L to induce TNFα production and then exposed to Nec-1. As seen in FIG. 13B, treatment of cells with Nec-1 significantly inhibited CD40L-induced TNFα production.

INCORPORATION BY REFERENCE

All publications, including all U.S. patents and U.S. published patent applications, cited herein are hereby incorporated by reference.

EQUIVALENTS

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

I claim:
1. A compound having formula I:

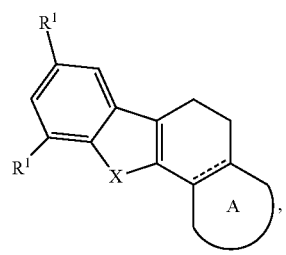

or a pharmaceutically acceptable salt thereof, wherein, independently for each occurrence,
Ⓐ represents a substituted or unsubstituted furan, isothiazole, oxazole, thiazole, thiadiazole, or triazole;
⟿ represents a double bond or a single bond;
$R^1$ is —H or alkyl; and
X represents —O—, —$NR^1$—, or —S—.

2. A method of treating an inflammatory disease or other disease associated with RIP1 kinase-mediated TNFα production, comprising administering to a subject a therapeutically effective amount of a compound having formula I:

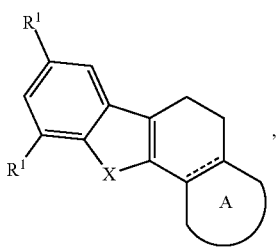

or a pharmaceutically acceptable salt thereof,
wherein, independently for each occurrence,
Ⓐ represents a substituted or unsubstituted 5-membered heteroaryl;
⟿ represents a double bond or a single bond;
$R^1$ is —H or alkyl; and
X represents —O—, —$NR^1$—, or —S—.

3. The method of claim 2, wherein the compound is selected from the group consisting of

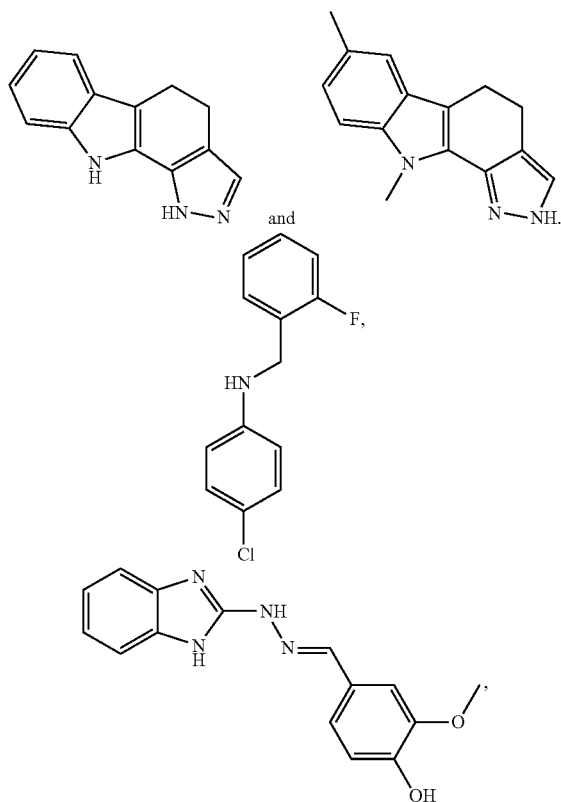

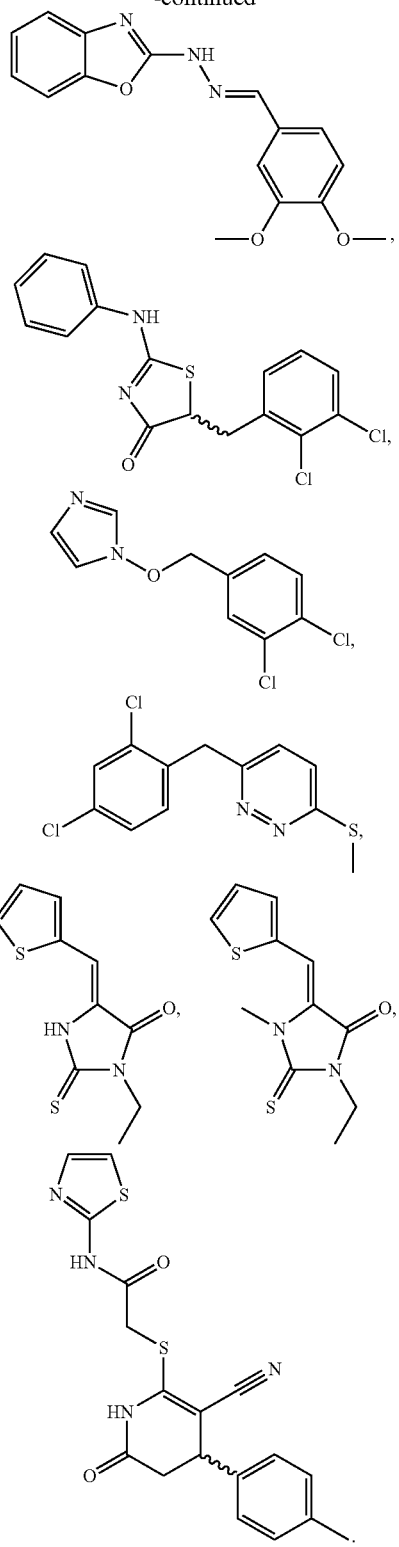

4. The method of claim 2, wherein the subject is a subject in need thereof; and the subject in need thereof is a subject who has been diagnosed with an inflammatory disease or a subject who is at high risk for an inflammatory disease.

5. The method of claim 2, wherein the method is a method of treating an inflammatory disease; and the inflammatory diseases is inflammatory bowel disease, rheumatoid arthritis, psoriatic arthritis, psoriasis, diabetes mellitus, Alzheimer's disease, refractory asthma, multiple sclerosis, atherosclerosis, or vasculitis.

6. The compound of claim 1, wherein Ⓐ is unsubstituted.

7. The compound of claim 1, wherein Ⓐ represents substituted or unsubstituted isothiazole.

8. The compound of claim 1, wherein $R^1$ is —H.

9. The compound of claim 1, wherein at least one instance of $R^1$ is alkyl.

10. The compound of claim 1, wherein at least one instance of $R^1$ is methyl, ethyl, n-propyl, or isopropyl.

11. The compound of claim 1, wherein at least one instance of $R^1$ is methyl.

12. The compound of claim 1, wherein at least one instance of $R^1$ is ethyl.

13. The compound of claim 1, wherein one instance of $R^1$ is methyl, ethyl, n-propyl, or isopropyl.

14. The compound of claim 1, wherein one instance of $R^1$ is methyl.

15. The compound of claim 1, wherein one instance of $R^1$ is ethyl.

16. The compound of claim 1, wherein X represents —$NR^1$—.

17. The compound of claim 1, wherein X represents —NH—.

18. The compound of claim 1, wherein X represents —$N(CH_3)$—.

19. The method of claim 2, wherein Ⓐ represents an unsubstituted 5-membered heteroaryl.

20. The method of claim 2, wherein Ⓐ represents substituted or unsubstituted furan, imidazole, isoxazole, isothiazole, oxadiazole, oxazole, pyrazole, pyrrole, thiazole, thiadiazole, thiophene, or triazole.

21. The method of claim 2, wherein Ⓐ represents

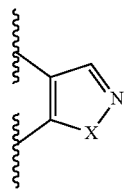 or 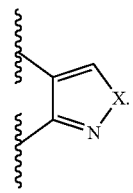

22. The method of claim 2, wherein Ⓐ represents

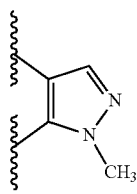 or 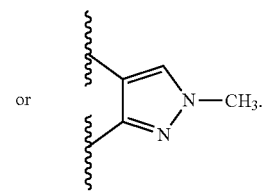

23. The method of claim 2, wherein Ⓐ represents

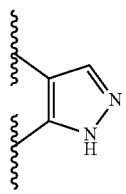 or 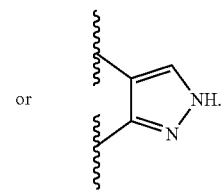

24. The method of claim 2, wherein $R^1$ is —H.

25. The method of claim 2, wherein at least one instance of $R^1$ is alkyl.

26. The method of claim 2, wherein at least one instance of $R^1$ is methyl, ethyl, n-propyl, or isopropyl.

27. The method of claim 2, wherein at least one instance of $R^1$ is methyl.

28. The method of claim 2, wherein at least one instance of $R^1$ is ethyl.

29. The method of claim 2, wherein one instance of $R^1$ is methyl, ethyl, n-propyl, or isopropyl.

30. The method of claim 2, wherein one instance of $R^1$ is methyl.

31. The method of claim 2, wherein one instance of $R^1$ is ethyl.

32. The method of claim 2, wherein X represents —$NR^1$—.

33. The method of claim 2, wherein X represents —NH—.

34. The method of claim 2, wherein X represents —$N(CH_3)$—.

35. The method of claim 5, wherein the disease is Alzheimer's disease.

* * * * *

UNITED STATES PATENT AND TRADEMARK OFFICE
CERTIFICATE OF CORRECTION

PATENT NO. : 9,643,977 B2  
APPLICATION NO. : 14/004474  
DATED : May 9, 2017  
INVENTOR(S) : Junying Yuan Page 1 of 1

It is certified that error appears in the above-identified patent and that said Letters Patent is hereby corrected as shown below:

In the Specification

Column 1, Lines 18-21, please replace the text:
"The invention as made with support provided by the National Institutes of Health (Grant Nos. DPI OD000580 and ROI CA13896); therefore, the government has certain rights in this invention."

With:
--This invention was made with government support under OD000580 and CA138961 awarded by National Institutes of Health (NIH). The government has certain rights in this invention.--

Signed and Sealed this  
Eighth Day of November, 2022

Katherine Kelly Vidal  
*Director of the United States Patent and Trademark Office*